(12) United States Patent
Maharbiz et al.

(10) Patent No.: US 10,765,865 B2
(45) Date of Patent: Sep. 8, 2020

(54) IMPLANTS USING ULTRASONIC WAVES FOR STIMULATING TISSUE

(71) Applicant: The Regents of the University of California, Oakland, CA (US)

(72) Inventors: Michel M. Maharbiz, El Cerrito, CA (US); Dongjin Seo, Albany, CA (US); Konlin Shen, Oakland, CA (US); Jose M. Carmena, Berkeley, CA (US); Ryan Neely, El Cerrito, CA (US); Elad Alon, Oakland, CA (US); Jan Rabaey, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/401,060

(22) Filed: May 1, 2019

(65) Prior Publication Data

US 2020/0230441 A1    Jul. 23, 2020

Related U.S. Application Data

(63) Continuation of application No. 16/313,865, filed as application No. PCT/US2017/041264 on Jul. 7, 2017.
(Continued)

(51) Int. Cl.
*A61N 1/36* (2006.01)
*A61B 5/00* (2006.01)
(Continued)

(52) U.S. Cl.
CPC .......... *A61N 1/3605* (2013.01); *A61B 5/0031* (2013.01); *A61B 5/076* (2013.01);
(Continued)

(58) Field of Classification Search
CPC ...... A61N 7/02; A61N 1/3605; A61N 1/3787; A61N 1/37205; A61N 1/0534;
(Continued)

(56) References Cited

U.S. PATENT DOCUMENTS

| 2,830,274 A | 4/1958 | Rosen et al. |
| 5,749,909 A | 5/1998 | Schroeppel et al. |

(Continued)

FOREIGN PATENT DOCUMENTS

| EP | 2515996 A2 | 10/2012 |
| EP | 2355893 B1 | 12/2013 |

(Continued)

OTHER PUBLICATIONS

U.S. Office Action dated Jan. 10, 2018 issued in U.S. Appl. No. 15/702,301.

(Continued)

*Primary Examiner* — Elmer M Chao
(74) *Attorney, Agent, or Firm* — Tom Hunter; Weaver Austin Villeneuve & Sampson LLP

(57) ABSTRACT

Described herein are implantable devices configured to emit an electrical pulse. An exemplary implantable device includes an ultrasonic transducer configured to receive ultrasonic waves that power the implantable device and encode a trigger signal; a first electrode and a second electrode configured to be in electrical communication with a tissue and emit an electrical pulse to the tissue in response to the trigger signal; and an integrated circuit comprising an energy storage circuit. Also described are systems that include one or more implantable device and an interrogator configured to operate the one or more implantable devices. Further described is a closed loop system that includes a first device configured to detect a signal, an interrogator configured to emit a trigger signal in response to the detected
(Continued)

signal, and an implantable device configured to emit an electrical pulse in response to receiving the trigger signal. Further described are computer systems useful for operating one or more implantable devices, as well as methods of electrically stimulating a tissue.

16 Claims, 31 Drawing Sheets

Related U.S. Application Data

(60) Provisional application No. 62/359,672, filed on Jul. 7, 2016.

(51) Int. Cl.
| | | |
|---|---|---|
| *A61N 1/372* | (2006.01) | |
| *G01N 27/327* | (2006.01) | |
| *A61B 5/07* | (2006.01) | |
| *A61N 1/378* | (2006.01) | |
| *B06B 1/06* | (2006.01) | |
| *A61B 8/08* | (2006.01) | |
| *A61N 7/02* | (2006.01) | |
| *A61N 5/10* | (2006.01) | |
| *A61N 1/05* | (2006.01) | |
| *A61B 6/00* | (2006.01) | |
| *A61N 7/00* | (2006.01) | |
| *H02J 7/02* | (2016.01) | |
| *H02J 50/15* | (2016.01) | |

(52) U.S. Cl.
CPC ............ *A61B 5/686* (2013.01); *A61B 8/0808* (2013.01); *A61N 1/3787* (2013.01); *A61N 1/37205* (2013.01); *B06B 1/06* (2013.01); *G01N 27/327* (2013.01); *A61B 5/4836* (2013.01); *A61B 6/4258* (2013.01); *A61B 8/085* (2013.01); *A61B 8/0875* (2013.01); *A61B 8/48* (2013.01); *A61B 2560/0219* (2013.01); *A61B 2562/12* (2013.01); *A61M 2205/04* (2013.01); *A61M 2205/825* (2013.01); *A61N 1/0534* (2013.01); *A61N 1/372* (2013.01); *A61N 5/1071* (2013.01); *A61N 7/02* (2013.01); *A61N 2005/1087* (2013.01); *A61N 2007/0021* (2013.01); *H02J 7/025* (2013.01); *H02J 50/15* (2016.02)

(58) Field of Classification Search
CPC .... A61N 2007/0021; A61N 2005/1087; A61N 5/1071; A61B 5/686; A61B 5/076; A61B 5/0031; A61B 5/4836; A61B 5/1071; A61B 8/0808; A61B 8/48; A61B 8/0875; A61B 8/085; A61B 2505/05; A61B 2560/0219; A61B 2562/12; A61B 2562/028; A61N 6/4258; G01N 27/327; B06B 1/06; A61M 39/0208; A61M 2205/04; A61M 2205/825; H02J 50/15; H02J 50/90
See application file for complete search history.

(56) References Cited

U.S. PATENT DOCUMENTS

| | | |
|---|---|---|
| 6,170,488 B1 | 1/2001 | Spillman, Jr. et al. |
| 6,200,265 B1 | 3/2001 | Walsh et al. |
| 6,628,989 B1 | 9/2003 | Penner et al. |
| 6,654,638 B1 | 11/2003 | Sweeney |
| 7,024,248 B2 | 4/2006 | Penner et al. |
| 7,418,292 B2 | 8/2008 | Shafer |
| 7,479,112 B2 | 1/2009 | Sweeney et al. |
| 7,616,990 B2 | 11/2009 | Chavan et al. |
| 7,634,318 B2 | 12/2009 | Tran et al. |
| 7,757,565 B2 | 7/2010 | Chakrabartty |
| 7,769,442 B2 | 8/2010 | Shafer |
| 7,848,815 B2 | 12/2010 | Brisken et al. |
| 7,890,173 B2 | 2/2011 | Brisken et al. |
| 7,899,542 B2 | 3/2011 | Cowan et al. |
| 7,953,493 B2 | 5/2011 | Fowler et al. |
| 8,078,283 B2 | 12/2011 | Cowan et al. |
| 8,082,041 B1 | 12/2011 | Radziemski |
| 8,412,338 B2 | 4/2013 | Faltys |
| 8,480,585 B2 | 7/2013 | Slayton et al. |
| 8,494,637 B2 | 7/2013 | Cowan et al. |
| 8,494,639 B2 | 7/2013 | Cowan et al. |
| 8,494,642 B2 | 7/2013 | Cowan et al. |
| 8,494,643 B2 | 7/2013 | Cowan et al. |
| 8,494,644 B2 | 7/2013 | Cowan et al. |
| 8,612,002 B2 | 12/2013 | Faltys et al. |
| 8,634,908 B2 | 1/2014 | Cowan |
| 8,718,773 B2 | 5/2014 | Willis et al. |
| 8,788,034 B2 | 7/2014 | Levine et al. |
| 8,849,412 B2 | 9/2014 | Perryman et al. |
| 8,855,767 B2 | 10/2014 | Faltys et al. |
| 8,874,233 B2 | 10/2014 | McLaughlin et al. |
| 8,886,339 B2 | 11/2014 | Faltys et al. |
| 8,934,972 B2 | 1/2015 | Penner |
| 8,996,116 B2 | 3/2015 | Faltys et al. |
| 9,162,064 B2 | 10/2015 | Faltys et al. |
| 9,174,041 B2 | 11/2015 | Faltys et al. |
| 9,199,089 B2 | 12/2015 | Perryman et al. |
| 9,211,410 B2 | 12/2015 | Levine et al. |
| 9,220,897 B2 | 12/2015 | Perryman et al. |
| 9,242,103 B2 | 1/2016 | Perryman et al. |
| 9,364,362 B2 | 6/2016 | Berkcan et al. |
| 9,409,030 B2 | 8/2016 | Perryman et al. |
| 9,452,286 B2 | 9/2016 | Cowan et al. |
| 9,544,068 B2 | 1/2017 | Arbabian et al. |
| 9,566,449 B2 | 2/2017 | Perryman et al. |
| 9,623,253 B2 | 4/2017 | Perryman et al. |
| 9,700,716 B2 | 7/2017 | Faltys et al. |
| 9,717,921 B2 | 8/2017 | Perryman et al. |
| 9,757,571 B2 | 9/2017 | Perryman et al. |
| 9,789,314 B2 | 10/2017 | Perryman et al. |
| 9,802,055 B2 | 10/2017 | Reinke et al. |
| 9,833,621 B2 | 12/2017 | Levine |
| 9,849,286 B2 | 12/2017 | Levine et al. |
| 9,925,384 B2 | 3/2018 | Perryman et al. |
| 9,974,593 B2 | 5/2018 | Barman |
| 9,974,965 B2 | 5/2018 | Perryman et al. |
| 9,993,651 B2 | 6/2018 | Faltys et al. |
| 10,118,054 B2 | 11/2018 | Maharbiz et al. |
| 10,201,706 B2 | 2/2019 | Schwab et al. |
| 10,220,203 B2 | 3/2019 | Faltys et al. |
| 10,300,309 B2 | 5/2019 | Maharbiz et al. |
| 10,300,310 B2 | 5/2019 | Maharbiz et al. |
| 10,576,305 B2 | 3/2020 | Maharbiz et al. |
| 2005/0049492 A1 | 3/2005 | Sweeney et al. |
| 2005/0075702 A1 | 4/2005 | Shafer |
| 2005/0152946 A1 | 7/2005 | Hunter et al. |
| 2007/0293912 A1 | 12/2007 | Cowan et al. |
| 2009/0018403 A1 | 1/2009 | Black et al. |
| 2009/0275997 A1 | 11/2009 | Faltys et al. |
| 2010/0268078 A1 | 10/2010 | Scarantino et al. |
| 2011/0054569 A1 | 3/2011 | Zitnik et al. |
| 2013/0062527 A1 | 3/2013 | Hyde et al. |
| 2013/0178915 A1 | 7/2013 | Radziemski et al. |
| 2013/0226259 A1 | 8/2013 | Penner |
| 2014/0253435 A1 | 9/2014 | Boser et al. |
| 2014/0336474 A1 | 11/2014 | Arbabian et al. |
| 2014/0336727 A1 | 11/2014 | Perryman et al. |
| 2015/0100110 A1 | 4/2015 | Towe et al. |
| 2015/0112233 A1 | 4/2015 | Towe et al. |
| 2015/0241447 A1 | 8/2015 | Zitnik et al. |
| 2015/0297900 A1 | 10/2015 | Perryman et al. |
| 2016/0000590 A1 | 1/2016 | Boyden et al. |
| 2016/0007893 A1 | 1/2016 | Roberts |
| 2016/0023003 A1 | 1/2016 | Perryman et al. |
| 2016/0038741 A1 | 2/2016 | Perryman et al. |

(56) References Cited

U.S. PATENT DOCUMENTS

| | | |
|---|---|---|
| 2016/0038769 A1 | 2/2016 | Sullivan et al. |
| 2016/0067497 A1 | 3/2016 | Levine et al. |
| 2016/0114165 A1 | 4/2016 | Levine et al. |
| 2016/0331952 A1 | 11/2016 | Faltys et al. |
| 2016/0331962 A1 | 11/2016 | Schwab et al. |
| 2017/0100588 A1 | 4/2017 | Schwab et al. |
| 2017/0100589 A1 | 4/2017 | Schwab et al. |
| 2017/0100604 A1 | 4/2017 | Schwab et al. |
| 2017/0100605 A1 | 4/2017 | Schwab et al. |
| 2017/0117753 A1 | 4/2017 | Charthad et al. |
| 2017/0125892 A1 | 5/2017 | Arbabian et al. |
| 2017/0197082 A1 | 7/2017 | Pang et al. |
| 2018/0008828 A1 | 1/2018 | Perryman et al. |
| 2018/0085605 A1 | 3/2018 | Maharbiz et al. |
| 2018/0117319 A1 | 5/2018 | Chew et al. |
| 2018/0117320 A1 | 5/2018 | Levine et al. |
| 2018/0169423 A1 | 6/2018 | Perryman et al. |
| 2018/0236248 A1 | 8/2018 | Perryman et al. |
| 2018/0264277 A1 | 9/2018 | Perryman et al. |
| 2018/0289970 A1 | 10/2018 | Faltys et al. |
| 2019/0022427 A1 | 1/2019 | Maharbiz et al. |
| 2019/0022428 A1 | 1/2019 | Maharbiz et al. |
| 2019/0150881 A1 | 5/2019 | Maharbiz et al. |
| 2019/0150882 A1 | 5/2019 | Maharbiz et al. |
| 2019/0150883 A1 | 5/2019 | Maharbiz et al. |
| 2019/0150884 A1 | 5/2019 | Maharbiz et al. |
| 2019/0321640 A1 | 10/2019 | Carmena et al. |
| 2019/0321644 A1 | 10/2019 | Maharbiz et al. |
| 2020/0023208 A1 | 1/2020 | Maharbiz et al. |
| 2020/0023209 A1 | 1/2020 | Maharbiz et al. |

FOREIGN PATENT DOCUMENTS

| | | |
|---|---|---|
| EP | 2667942 A2 | 12/2013 |
| EP | 2694154 A1 | 2/2014 |
| EP | 2741810 A1 | 6/2014 |
| EP | 2162185 B1 | 7/2015 |
| EP | 2928557 A2 | 10/2015 |
| EP | 2707094 B1 | 2/2016 |
| EP | 2755718 B1 | 12/2017 |
| EP | 2736592 B1 | 1/2018 |
| EP | 3285856 A | 2/2018 |
| EP | 3294376 A | 3/2018 |
| EP | 3338855 A1 | 6/2018 |
| EP | 2440284 B1 | 9/2018 |
| EP | 3403690 A1 | 11/2018 |
| WO | WO/2005/032653 A1 | 4/2005 |
| WO | WO/2007/050657 A1 | 5/2007 |
| WO | WO/2007/090159 A1 | 8/2007 |
| WO | WO/2010/059617 A2 | 5/2010 |
| WO | WO/2010/144578 A2 | 12/2010 |
| WO | WO/2011/028763 A2 | 3/2011 |
| WO | WO/2011/079309 A2 | 6/2011 |
| WO | WO/2012/057868 A1 | 5/2012 |
| WO | WO/2012/103519 A2 | 8/2012 |
| WO | WO/2012/138782 A1 | 10/2012 |
| WO | WO/2012/154865 A2 | 11/2012 |
| WO | WO/2013/019757 A2 | 2/2013 |
| WO | WO/2013/025632 A1 | 2/2013 |
| WO | WO/2013/040549 A1 | 3/2013 |
| WO | WO/2013/044207 A1 | 3/2013 |
| WO | WO/2013/134479 A1 | 9/2013 |
| WO | WO/2014/089299 A2 | 6/2014 |
| WO | WO/2014/153218 A1 | 9/2014 |
| WO | WO/2014/153221 A1 | 9/2014 |
| WO | WO/2014/153223 A1 | 9/2014 |
| WO | WO/2014/153228 A1 | 9/2014 |
| WO | WO/2014/169145 A1 | 10/2014 |
| WO | WO/2015/127476 A1 | 8/2015 |
| WO | WO/2015/142842 A2 | 9/2015 |
| WO | WO/2016/170510 A1 | 10/2016 |
| WO | WO/2016/183353 A1 | 11/2016 |
| WO | WO/2016/187114 A1 | 11/2016 |
| WO | WO/2018/009905 A2 | 1/2018 |
| WO | WO/2018/009908 A1 | 1/2018 |
| WO | WO/2018/009910 A1 | 1/2018 |
| WO | WO/2018/009911 A1 | 1/2018 |
| WO | WO/2018/009912 A1 | 1/2018 |
| WO | WO/2018/081763 A1 | 5/2018 |
| WO | WO/2018/081826 A1 | 5/2018 |
| WO | WO/2018/087193 A1 | 5/2018 |
| WO | WO/2018/089895 A2 | 5/2018 |
| WO | WO/2018/118857 A1 | 6/2018 |
| WO | WO/2018/118860 A1 | 6/2018 |
| WO | WO/2018/118861 A1 | 6/2018 |
| WO | WO/2018/118864 A1 | 6/2018 |
| WO | WO/2018/118866 A1 | 6/2018 |

OTHER PUBLICATIONS

U.S. Final Office Action dated Jul. 27, 2018 issued in U.S. Appl. No. 15/702,301.

U.S. Notice of Allowance dated Aug. 24, 2018 issued in U.S. Appl. No. 15/702,301.

U.S. Notice of Allowance dated Jan. 11, 2019 issued in U.S. Appl. No. 16/141,902.

U.S. Notice of Allowance dated Jan. 9, 2019 issued in U.S. Appl. No. 16/141,930.

PCT International Search Report and Written Opinion dated Jan. 2, 2018 issued in PCT/US2017/041257.

PCT International Preliminary Report on Patentability and Written Opinion dated Jan. 17, 2019 issued in PCT/US2017/041257.

PCT International Search Report and Written Opinion dated Nov. 15, 2017 issued in PCT/US2017/041260.

PCT International Preliminary Report on Patentability and Written Opinion dated Jan. 17, 2019 issued in PCT/US2017/041260.

PCT International Search Report and Written Opinion dated Nov. 13, 2017 issued in PCT/US2017/041263.

PCT International Preliminary Report on Patentability and Written Opinion dated Jan. 17, 2019 issued in PCT/US2017/041263.

PCT International Search Report and Written Opinion dated Sep. 20, 2017 issued in PCT/US2017/041262.

PCT International Preliminary Report on Patentability and Written Opinion dated Jan. 17, 2019 issued in PCT/US2017/041262.

PCT International Search Report and Written Opinion dated Nov. 2, 2017 issued in PCT/US2017/041264.

PCT International Preliminary Report on Patentability and Written Opinion dated Jan. 17, 2019 issued in PCT/US2017/041264.

Afroz et al., "Implantable Sic Based RF Antenna Biosensor for Continuous Glucose Monitoring", IEEE, 2013, 4 pages.

Ahmadi et al., "A Wireless-Implantable Microsystem for Continuous Blood Glucose Monitoring", IEEE Transactions on Biomedical Circuits and Systems, vol. 3 No. 3, Jun. 2009, pp. 169-180.

Alivisatos et al., "Nanotools for Neuroscience and Brain Activity Mapping", ACS Nano, vol. 7, No. 3, 2013, pp. 1850-1866.

Bai et al., "Single-Unit neural Recording with Active Microelectrode Arrays", IEEE Transactions on Biomedical Engineering, vol. 48, No. 8, Aug. 2001, pp. 911-920.

Bartlett et al., "Strategies for the Development of Amperometric Enzyme Electrodes", Biosensors, vol. 3, 1987, pp. 359-379.

Bertrand et al., "Beamforming Approaches for Untethered, Ultrasonic Neural Dust Motes for Cortical Recording: A Simulation Study", 36th Annual International Conference of the IEEE Engineering in Medicine and Biology Society, 2014, pp. 2625-2628.

Beuter et al., "Closed-Loop Cortical Neuromodulation in Parkinson's Disease: An Alternative to Deep Brain Stimulation?", Clinical Neurophysiology, vol. 125, 2014, pp. 874-885.

Beyer et al., "An Implantable MOSFET Dosimeter for the Measurement of Radiation Dose in Tissue During Cancer Therapy", IEEE Sensors Journal, vol. 8, No. 1, 2008, pp. 38-51.

Bhadra et al., "High-Frequency Electrical Conduction Block of Mammalian Peripheral Motor Nerve", Muscle Nerve, vol. 32, No. 6, Dec. 2005, pp. 782-790.

Biederman et al., "A 4.78 mm 2 Fully-Integrated Neuromodulation SoC Combining 64 Acquisition Channels with Digital Compression and Simultaneous Dual Stimulation", IEEE Journal of Solid-State Circuits, vol. 50, No. 4, 2015, pp. 1038-1047.

(56) References Cited

OTHER PUBLICATIONS

Biederman et al., "A Fully-Integrated, Miniaturized (0.125 mm²) 10.5 μW Wireless Neural Sensor", IEEE Journal of Solid-State Circuits, vol. 48, No. 4, 2013, pp. 960-970.
Birmingham et al., "Bioelectronic Medicines: A Research Roadmap", Nature Reviews Drug Discovery, vol. 13, No. 6, 2014, pp. 399-400.
Boretius et al., "A Transverse Intrafascicular Multichannel Electrode (Time) to Interface with the Peripheral Nerve", Biosensors and Bioelectronics, vol. 26, No. 1, Sep. 2010, pp. 62-69.
Cardin et al., "Targeted Optogenetic Stimulation and Recording of Neurons in Vivo Using Cell-Type-Specific Expression of Channelrhodopsin-2", Nature Protocols, vol. 5, 2010, pp. 247-254.
Carmena et al., "Learning to Control a Brain—Machine Interface for Reaching and Grasping by Primates", PLoS Biology, vol. 1, No. 2, 2003, pp. 193-208.
Carvalho-De-Souza et al., "Photosensitivity of Neurons Enabled by Cell-Targeted Gold Nanoparticles", Neuron, vol. 86, No. 1, Apr. 8, 2015, pp. 207-217.
Celinskis, Dmitrijs et al., "Wireless impedance measurements for monitoring peripheral vascular disease", 36th Annual International Conference of the IEEE Engineering in Medicine and Biology Society, IEEE, 2014, pp. 6937-6940.
Chapin et al., "Real-Time Control of a Robot Arm Using Simultaneously Recorded Neurons in the Motor Cortex", Nature Neuroscience, vol. 2, 1999, pp. 664-670.
Charthad et al., "A mm-Sized Implantable Medical Device (IMD) with Ultrasonic Power Transfer and a Hybrid Bi-Directional Data Link", IEEE Journal of Solid-State Circuits, vol. 50, No. 8, 2015, pp. 1741-1753.
Chestek et al., "Long-Term Stability of Neural Prosthetic Control Signals From Silicon Cortical Arrays in Rhesus Macaque Motor Cortex", Journal of Neural Engineering, vol. 8, 2011, pp. 1-11.
Cogan et al., "Plasma-Enhanced Chemical Vapor Deposited Silicon Carbide as an Implantable Dielectric Coating", Journal of Biomedical Research: Part A, vol. 67A, No. 3, Oct. 20, 2003, pp. 856-867.
Creasey et al., "An Implantable Neuroprosthesis for Restoring Bladder and Bowel Control to Patients with Spinal Cord Injuries: A Multicenter Trial", Archives of Physical Medicine and Rehabilitation, vol. 82, No. 11,, Nov. 2001, pp. 1512-1519.
Dadarlat et al., "A Learning-Based Approach to Artificial Sensory Feedback Leads to Optimal Integration", Nature Neuroscience, vol. 18, No. 1, Jan. 2015, pp. 138-144.
Delivopoulos et al., "Concurrent Recordings of Bladder Afferents from Multiple Nerves Using a Microfabricated PDMS Microchannel Electrode Array", Lab on a Chip, vol. 12, No. 14, Jul. 2012, pp. 2540-2551.
Dellis, Jean-Luc, "Zfit", version 1.2, MathWorks, Updated on 2010, 6 pages.
Denison et al., "A 2 μW, 100 nV/rtHz, Chopper-Stabilized Instrumentation Amplifier for Chronic Measurement of Neural Field Potentials", IEEE Journal of Solid-State Circuits, vol. 42 No. 12, 2007, pp. 2934-2945.
Dingli et al., "Successful Therapy Must Eradicate Cancer Stem Cells", Stem Cells, vol. 24, 2006, pp. 2603-2610.
Du et al., "Multiplexed, High Density Electrophysiology with Nanofabricated Neural Probes", PLOS One, vol. 6, No. 10, Oct. 2011, pp. e26204.1-11.
Epoxy Technology, "EPO-TEK H20E", Rev. XIII, Jul. 2015, 2 pages.
Famm et al., "Drug Discovery: A Jump-Start for Electroceuticals", Nature, vol. 496, Apr. 2013, pp. 159-161.
Fan et al., "A Wireless Multi-Channel Recording System for Freely Behaving Mice and Rats", PLoS One, vol. 6, No. 7, Jul. 2011, pp. e22033.1-9.
Food and Drug Administration, "Information for Manufacturers Seeking Marketing Clearance of Diagnostic Ultrasound Systems and Transducers", Guidance for Industry and FDA Staff, Sep. 9, 2008, 68 pages.
Foster et al., "A Freely-Moving Monkey Treadmill Model", Journal of Neural Engineering, vol. 11, 2014, pp. 1-14.
Frewin et al., "Silicon Carbide Materials for Biomedical Applications", Carbon for Sensing Devices, Oct. 8, 2014, pp. 153-207.
Ganguly et al., "Emergence of a Stable Cortical Map for Neuroprosthetic Control", PLoS Biology, vol. 7, No. 7, Jul. 2009, pp. e1000153.1-13.
Girman et al., "Rat Experimental Transplantation Surgery: A Pactical Guide", Springer, eBook, 2015, 257 pages.
Gold et al., "Using Extracellular Action Potential Recordings to Constrain Compartmental Models", Journal of Computational Neuroscience, vol. 23, 2007, pp. 39-58.
Grahn et al., "A Neurochemical Closed-Loop Controller for Deep Brain-Stimulation: Toward Individualized Smart Neuromodulation Therapies", Frontiers in Neuroscience, vol. 8, Article 169, Jun. 2014, pp. 1-11.
Gruner et al., "Nonlinear Muscle Recruitment During Intramuscular and Nerve Stimulation", Journal of Rehabilitation Research and Development, vol. 26, No. 2, 1989, pp. 1-16.
Halperin et al., "Perez and Brady's Principles and Practice of Radiation Oncology", Lippincott Williams & Wilkins, 6th Edition, 2013, 2 pages.
Harman-Boehm et al., "Noninvasive Glucose Monitoring: A Novel Approach", Journal of Diabetes Science and Technology, vol. 3, No. 2, Mar. 2009, pp. 253-260.
Harrison et al., "A Low-Power Integrated Circuit for a Wireless 100-Electrode Neural Recording System", IEEE Journal of Solid-State Circuits, vol. 42, No. 1, 2007, pp. 123-133.
Harrison, Reid R., "Designing Efficient Inductive Power Links for Implantable Devices", IEEE International Symposium on Circuits and Systems, 2007, pp. 2080-2083.
He et al., "Nanoscale Neuro-Integrative Coatings for Neural Implants", Biomaterials, vol. 26, 2005, pp. 2983-2990.
Hess et al., "PECVD Silicon Carbide as a Thin Film Packaging Material for Microfabricated Neural Electrodes", Materials Research Society Symposium Proceedings, vol. 1009, 2007, pp. 8-13.
Hochberg et al., "Reach and Grasp by People with Tetraplegia Using a Neurally Controlled Robotic Arm", Nature, vol. 485, May 2012, pp. 372-375.
Holland, Richard, "Resonant Properties of Piezoelectric Ceramic Rectangular Parallelepipeds", The Journal of the Acoustical Society of America, vol. 43, No. 5, 1968, pp. 988-997.
Holmes-Siedle et al., "RADFET: A Review of the Use of Metal-Oxide-Silicon Devices as Dosimeters", International Journal of Radiation Applications and Instrumentation, Part C, Radiation Physics and Chemistry, vol. 28, No. 2, 1986, pp. 235-244.
Holmes-Siedle et al., "The Physics of Failure of MIS Devices Under Radiation", IEEE Transactions on Reliability, vol. R-17, No. 1, 1968, pp. 34-44.
Hoskins et al., "Diagnostic Ultrasound: Physics and Equipment", 2003, 276 pages.
Hynynen et al., "Demonstration of Potential Noninvasive Ultrasound Brain Therapy through an Intact Skull", Ultrasound in Medicine and Biology, vol. 24, No. 2, Feb. 1998, pp. 275-283.
IEEE, "IEEE Standard for Safety Levels with Respect to Human Emposure to Radio Frequency Electromagnetic Fileds, 3khz to 300 Ghz", IEEE Standards Coordinating Committee 28 on Non-Ionizing Radiation Hazards, 1991, 72 pages.
IEEE, "IEEE Standard for Safety Levels with Respect to Human Exposure to Radio Frequency Electromagnetic Fields, 3 kHz to 300 GHz", IEEE International Committee on Electromagnetic Safety (SCC39), Apr. 2006, 250 pages.
Ishida et al., "Insole Pedometer With Piezoelectric Energy Harvester and 2 V Organic Circuits", IEEE Journal of Solid-State Circuits, vol. 48, No. 1, 2013, pp. 255-264.
Jow et al., "Design and Optimization of Printed Spiral Coils for Efficient Transcutaneous Inductive Power Transmission", IEEE Transactions on Biomedical Circuits and Systems, vol. 1, No. 3, 2007, pp. 193-202.
Kay, Joshua, "Rodent Wearable Ultrasound Interrogation System for Wireless Neural Recording", Berkeley EECS, Technical Report No. UCS/EECS-2017-27, May 4, 2017, 50 pages.
Kim et al., "Injectable, Cellular-Scale Optoelectronics with Applications for Wireless Optogenetics", Science, vol. 340, Apr. 12, 2013, pp. 211-216.

(56) References Cited

OTHER PUBLICATIONS

Kiourti et al., "A Wireless Fully Passive Neural Recording Device for Unobtrusive Neuropotential Monitoring", IEEE Transactions on Biomedical Engineering, vol. 63, No. 1, 2016, pp. 131-137.

Klueh et al., "Metabolic Biofouling of Glucose Sensors in Vivo: Role of Tissue Microhemorrhages", Journal of Diabetes Science and Technology, vol. 5, No. 3, May 2011, pp. 583-595.

Koralek et al., "Corticostriatal Plasticity is Necessary for Learning Intentional Neuroprosthetic Skills", Nature, vol. 483, Mar. 15, 2012, pp. 331-335.

Kozai et al., "Ultrasmall Implantable Composite Microelectrodes with Bioactive Surfaces for Chronic Neural Interfaces", Nature Materials, vol. 11, 2012, pp. 1065-1073.

Krimholtz et al., "New Equivalent Circuits for Elementary Piezoelectric Transducers", Electronics Letters, vol. 6, No. 13, 1970, pp. 398-399.

Krook-Magnuson, "Neuroelectronics and Biooptics: CLoed Loop Technologies in Neurological Disorders", JAMA Neurology, vol. 72, No. 7, Jul. 2015, pp. 823-829.

Kuo et al., "Associations Between Periodontal Diseases and Systematic Disease: A Review of the Inter-relationships and Interactions with Diabetes, Respiratory Diseases, Cardiovascular Diseases and Osteoporosis", Public Health, vol. 122, No. 4, Apr. 2008, pp. 417-433.

Lapatki et al., "A Thin, Flexible Multielectrode Grid for High-Density Surface EMG", Journal of Applied Physiology, vol. 96, No. 1, Jan. 2004, pp. 327-336.

Larson et al., "Miniature Ultrasonically Powered Wireless Nerve Cuff Stimulator", Proceedings of the 5th International IEEE/EMBS Conference on Neural Engineering, 2011, pp. 265-268.

Ledochowitsch et al., "Fabrication and Testing of a Large Area, High Density, Parylene MEMS µECOG Array", IEEE 24th International Conference on Micro Electro Mechanical Systems, 2011, pp. 1031-1034.

Lee et al., "A Wideband Dual-Antenna Receiver for Wireless Recording from Animals Behaving in Large Arenas", IEEE Transactions on Biomedical Engineering, vol. 60, No. 7, 2013, pp. 1993-2004.

Lee et al., "An Inductively Powered Scalable 32-Channel Wireless Neural Recording System-on-a-Chip for Neuroscience Applications", IEEE Transactions on Biomedical Circuits and Systems, vol. 4, No. 6, 2010, pp. 360-371.

Lefurge et al., "Chronically Implanted Intrafascicular Recording Electrodes", Annals of Biomedical Engineering, vol. 19, No. 2, 1991, pp. 197-207.

Leighton, Timothy G., "What is Ultrasound", Progress in Biophysics and Molecular Biology, vol. 93, 2007, pp. 3-83.

Lin et al., "Low Phase Noise Array-Composite Micromechanical Wine-Glass Disk Oscillator", IEEE InternationalElectron Devices Meeting, IEDM Technical Digest, 2005, pp. 1-4.

Lind et al., "The Density Difference Between Tissue and Neural Probes is a Key Factor for Glial Scarring", Scientific Reports, vol. 3, 2013, pp. 2942.1-7.

Liu et al., "Monte Carlo Simulation Studies of EEG and MEG Localization Accuracy", Human Brain Mapping, vol. 16, 2002, pp. 47-62.

Lu et al., "Current Challenges to the Clinical Translation of Brain Machine Interface Technology", International Review of Neurobiology, vol. 107, 2012, pp. 137-160.

Maleki et al., "An Ultrasonically Powered Implantable Micro-Oxygen Generator (IMOG)", IEEE Transactions on Biomedical Engineering, 2011, pp. 3104-3111.

Malmivuo et al., "Effect of Skull Resistivity on the Spatial Resolutions of EEG and MEG", IEEE Transactions on Biomedical Engineering, vol. 51 No. 7, Jul. 7, 2004, pp. 1276-1280.

Marblestone et al., "Physical Principles for Scalable Neural Recording", Frontiers in Computational Neuroscience, vol. 7, Article 137, Oct. 2013, pp. 1-34.

Martinez-Valdes et al., "High-Density Surface Electromyography Provides Reliable Estimates of Motor Unit Behaviour", Clinical Neurophysiology, vol. 127, No. 6, 2016, pp. 2534-2541.

Maynard et al., "The Utah Intracortical Electrode Array: A Recording Structure for Potential Brain-Computer Interfaces", Electroencephalography and Clinical Neurophysiology, vol. 102, 1997, pp. 228-239.

Mazzilli et al., "In-Vitro Platform to study Ultrasound as Source for Wireless Energy Transfer and Communication for Implanted Medical Devices", 32nd Annual International Conference of the IEEE EMBS, 2010, pp. 3751-3754.

Meacham et al., "A Lithographically-Patterned, Elastic Multi-Electrode Array for Surface Stimulation of the Spinal Cord", Biomedical Microdevices, vol. 10, 2008, pp. 259-269.

Meng et al., "An Electroacoustic Recording Device for Wireless Sensing of Neural Signals", 35th Annual International Conference of the IEEE Engineering in Medicine and Biology Society (EMBC), 2013, pp. 3086-3088.

Mezzarane et al., "Experimental and Simulated EMG Responses in the Study of the Human Spinal Cord", Chapter 4, Electrodiagnosis in New Frontiers of Clinical Research, 2013, pp. 57-87.

Miranda et al., "HermesD: A High-Rate Long-Range Wireless Transmission System for Simultaneous Multichannel Neural Recording Applications", IEEE Transactions on Biomedical Circuits and Systems, vol. 4, No. 3, Jun. 2010, pp. 181-191.

Mohan et al., "Simple Accurate Expressions for Planar Spiral Inductances", IEEE Journal of Solid-State Circuits, vol. 34, No. 10, Oct. 1999, pp. 1419-1424.

Mohseni et al., "Guest Editorial Closing the Loop Via Advanced Neurotechnologies", IEEE Transactions on Neural Systems and Rehabilitation Engineering, vol. 20, No. 4, Jul. 2012, pp. 407-409.

Muller et al., "A 0.013 mm2, 5 µW, DC-Coupled Neural Signal Acquisition IC With 0.5 V Supply", IEEE Journal of Solid-State Circuits, vol. 47, No. 1, Jan. 2012, pp. 232-243.

Muller et al., "A Minimally Invasive 64-Channel Wireless µECoG Implant", IEEE Journal of Solid-State Circuits, vol. 50, No. 1,, Jan. 2015, pp. 1-16.

Nicolelis et al., "Chronic, Multisite, Multielectrode Recordings in Macaque Monkeys", PNAS, vol. 100, No. 19, Sep. 16, 2003, pp. 11041-11046.

Nicolelis, Miguel A. L., "Brain—Machine Interfaces to Restore Motor Function and Probe Neural Circuits", Nature Reviews Neuroscience, vol. 4, May 2003, pp. 417-422.

O'Doherty et al., "Active Tactile Exploration Using a Brain—Machine—Brain Interface", Nature, vol. 479, Nov. 10, 2011, pp. 228-231.

Ozeri et al., "Ultrasonic Transcutaneous Energy Transfer for Powering Implanted Devices", Ultrasonics, vol. 50, 2010, pp. 556-566.

Pavlov et al., "The Vagus Nerve and the Inflammatory Reflex-Linking Immunity and Metabolism", Nat Rev Endocrinol., vol. 8, No. 12, Dec. 2012, pp. 743-754.

Peisino, Michela, "Deeply implanted medical device based on a novel ultrasonic telemetry technology", Ecole Polytechnique Federale De Lausanne, 2013, pp. 147. Retrieved from the Internet: URL:https://infoscience.epfl.ch/record/186391/files/EPFL_TH5730.pdf [retrieved on Mar. 23, 2015].

Polikov et al., "Response of Brain Tissue to Chronically Implanted Neural Electrodes", Journal of Neuroscience Methods, vol. 148, 2005, pp. 1-18.

Polikov, et al., "In Vitro Model of Glial Scarring Around Neuroelectrodes Chronically Implanted in the CNS", Biomaterials, vol. 27, 2006, pp. 5368-5376.

Potter et al., "Stab Injury and Device Implantation within the Brain Results in Inversely Multiphasic Neuroinflammatory and Neurodegenerative Responses", Journal of Neural Engineering, vol. 9, No. 4, 2012, pp. 046020.

Rabaey et al., "Powering and Communicating with mm-Size Implants", IEEE, Design, Automation & Test in Europe, 2011, pp. 1-6.

Ramachnadran et al., "A Study of Parylene C Polymer Deposition Inside Microscale Gaps", IEEE Transactions on Advanced Packaging, vol. 30, 2007, pp. 712-724.

Randals, J.E.B, "Kinetics of Rapid Electrode Reactions", Discussions of the Faraday Society, vol. 1, 1947, pp. 11-19.

(56) References Cited

OTHER PUBLICATIONS

Rebrin et al., "Subcutaneous Glucose Monitoring by Means of Electrochemical Sensors: Fiction or Reality?", Journal of Biomedical Engineering, vol. 14, Jan. 1992, pp. 33-40.

Richards et al., "Efficiency of Energy Conversion for Devices Containing a Piezoelectric Component", Journal of Micromechanics and Microengineering, vol. 14, 2004, pp. 717-721.

Roa-Prada et al., "An Ultrasonic Through—Wall Communication (UTWC) System Model", Journal of Vibration and Acoustics, vol. 135, No. 1, 2013, pp. 1-12.

Robinson et al., "Nanowire Electrodes for High-Density Stimulation and Measurement of Neural Circuits", Frontiers in Neural Circuits, vol. 7, Article 38, Mar. 2013, pp. 1-5.

Rogers et al., "Materials and Mechanics for Stretchable Electronics", Science, vol. 327, Mar. 26, 2010, pp. 1603-1607.

Rosas-Ballina et al., "Acetylcholine-Synthesizing T Cells Relay Neural Signals in a Vagus Nerve Circuit", Science, vol. 334, No. 6052, Oct. 7, 2011, pp. 98-101.

Saddow et al., "Advances in Silicon Carbide Processing and Applications", Artech House, Inc., 2004, 223 pages.

Sadek et al., "Wiring Nanoscale Biosensors with Piezoelectric Nanomechanical Resonators", Nano Letters, vol. 10, 2010, pp. 1769-1773.

Schwarz et al., "Chronic, Wireless Recordings of Large Scale Brain Activity in Freely Moving Rhesus Monkeys", Nat Methods, vol. 11, No. 6, 2014, pp. 670-676.

Schwerdt et al., "A Fully Passive Wireless Microsystem for Recording of Neuropotentials Using RF Backscattering Methods", Journal of Microelectromechanical Systems, vol. 20, No. 5, 2011, pp. 1119-1130.

Seo et al., "Model Validation of Untethered, Ultrasonic Neural Dust Motes for Cortical Recording", Journal of Neuroscience Methods, vol. 244, 2015, pp. 114-122.

Seo et al., "Neural Dust: An Ultrasonic, Low Power Solution for Chronic Brain-Machine Interfaces", Neurons and Cognition, Jul. 2013, pp. 1-11.

Seo et al., "Ultrasonic Beamforming System for Interrogating Multiple Implantable Sensors", Conf Proc IEEE Eng Med Biol Soc., 2015, pp. 2673-2676.

Seo et al., "Wireless Recording in the Peripheral Nervous System with Ultrasonic Neural Dust", Neuron, vol. 91, Aug. 3, 2016, pp. 529-539.

Seo, Dongjin, "Design of Ultrasonic Power Link for Neural Dust", Technical Report No. UCB/EECS-2016-21, Electrical Engineering and Computer Sciences University of California at Berkeley, May 1, 2016, 71 pages.

Serruya et al., "Instant Neural Control of a Movement Signal", Nature, vol. 416, Mar. 14, 2002, pp. 141-142.

Seymour et al., "Neural Probe Design for Reduced Tissue Encapsulation in CNS", Biomaterials, vol. 28, 2007, pp. 3594-3607.

Shapiro et al., "Infrared Light Excites Cells by Changing their Electrical Capacitance", Nature Communications, vol. 3, Article 736, 2012, 10 pages.

Shen, Konlin, "Assembly of a Wireless Ultrasonic Backscatter System", Spring 2016, 61 pages.

Shenoy et al., "Neural Prosthetic Control Signals from Plan Activity", NeuroReport, vol. 14, No. 4, Mar. 24, 2003, pp. 591-596.

Sodagar et al., "Capacitive Coupling for Power and Data Telemetry to Implantable Biomedical Microsystems", Proceedings of the 4th International IEEE EMBS Conference on Neural Engineering, Apr. 29-May 2, 2009, pp. 411-414.

Srinivasan, Ramesh, "Methods to Improve the Spatial Resolution of EEG", International Journal of Bioelectromagnetism, vol. 1, No. 1, 1999, pp. 102-111.

Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, vol. 20, No. 4, Jul. 2012, pp. 410-421.

Stark, Nancy, "Literature Review: Biological Safety of Parylene C", Medical Device and Diagnostic Industry, Mar. 1996, 7 pages.

Stevenson et al., "How Advances in Neural Recording Affect Data Analysis", Nature Neuroscience, vol. 14, No. 2, Feb. 2011, pp. 139-142.

Steyaert et al., "A Micropower Low-Noise Monolithic Instrumentation Amplifier for Medical Purposes", IEEE Journal of Solid-State Circuits, vol. Section-22, No. 6, Dec. 1987, pp. 1163-1168.

Strollo et al., "Upper-Airway Stimulation for Obstructive Sleep Apnea", New England Journal of Medicine, vol. 370, Jan. 9, 2014, pp. 139-149.

Stypulkowski et al., "Brain Stimulation for Epilepsy—Local and Remote Modulation of Network Excitability", Brain Stimulation, vol. 7, No. 3, 2014, pp. 350-358.

Sudhakar, Akulapalli, "History of Cancer, Ancient and Modern Treatment Methods", Journal of Cancer Science and Therapy, vol. 1, No. 2, 2009, 4 pages.

Suner et al., "Reliability of Signals from a Chronically Implanted, Silicon-Based Electrode Array in Non-Human Primate Primary Motor Cortex", IEEE Transactions on Neural Systems and Rehabilitation Engineering, vol. 13, No. 4, Dec. 2005, pp. 524-541.

Swett et al., "Motoneurons of the Rat Sciatic Nerve", Experimental Neurology, vol. 93, 1986, pp. 227-252.

Swisher et al., "Impedance Sensing Device Enables Early Detection of Pressure Ulcers in Vivo", Nature Communications, vol. 6, 2015, 17 pages.

Szuts et al., "A wireless Multi-Channel Neural Amplifier for Freely Moving Animals", Nature Neuroscience, vol. 14, 2011, pp. 263-269.

Tang et al., "Integrated Ultrasonic System for Measuring Body-Fat Composition", IEEE International Solid-State Circuits Conference, 2015, 3 pages.

Tang et al., "Miniaturizing Ultrasonic System for Portable Health Care and Fitness", IEEE Transactions on Biomedical Circuits and Systems, vol. 9, No. 6, Dec. 2015, pp. 767-776.

Trolier-McKinstry et al., "Thin Film Piezoelectrics for MEMS", Journal of Electroceramics, vol. 12, 2004, pp. 7-17.

Turner et al., "Cerebral Astrocyte Response to Micromachined Silicon Implants", Experimental Neurology, vol. 156, 1999, pp. 33-49.

Updike et al., "Enzymatic Glucose Sensors: Improved Long Term Performance in Vitro and in Vivo", ASAIO Journal, vol. 40, 1994, pp. 157-163.

Venkatraman et al., "Active Sensing of Target Location Encoded by Cortical Microstimulation", IEEE Transactions on Neural Systems and Rehabilitation Engineering, vol. 19, No. 3, Jun. 2011, pp. 317-324.

Watanabe et al., "Reconstruction of Movement-Related Intracortical Activity From Micro-Electrcorticogram Array Signals in Monkey Motor Cortex", Journal of Neural Engineering, vol. 9, 2012, 58 pages.

Weissleder et al., "Molecular imaging", Radiology, vol. 219, 2001, 316-333.

Wells et al., "Optical Stimulation of Neural Tissue in Vivo", Optics Letters, vol. 30, No. 5, 2005, pp. 504-506.

Wilkins et al., "Glucose Monitoring: State of the Art and Future Possibilities", Medical Engineering and Physics, vol. 18, No. 4, 1996, pp. 273-288.

Williamson et al., "Localized Electrical Nerve Blocking", IEEE Transactions on Biomedical Engineering, vol. 52, No. 3, Mar. 2005, pp. 362-370.

Wilson et al., "Better Speech Recognition with Cochlear Implants", Letters to Nature, vol. 352, Jul. 18, 1991, pp. 236-238.

Wolgemuth, Lonny, "Assessing the Performance and Suitability of Parylene Coating", Medical Device and Diagnostic Industry, Aug. 2000, 6 pages.

Wong et al., "Advantages of Capacitive Micromachined Ultrasonics Transducers (CMUTs) for High Intensity Focused Ultrasound (HIFU)", IEEE Ultrasonics Symposium, 2007, pp. 1313-1316.

Xu et al., "Stretchable Batteries with Self-Similar Serpentine Interconnects and Integrated Wireless Recharging Systems", Nature Communications, 2013, 36 pages.

(56) References Cited

OTHER PUBLICATIONS

Yakolev et al., "Implantable Biomedical Devices: Wireless Powering and Communication", IEEE Communications Magazine, Apr. 2012, pp. 152-159.
Yin et al., "Wireless Neurosensor for Full-Spectrum Electrophysiology Recordings During Free Behavior", NeuroResource, Neuron, vol. 84, Dec. 17, 2014, p. 1170-1182.
Zenner et al., "Human Studies of a Piezoelectric Transducer and a Microphone for a Totally Implantable Electronic Hearing Device", The American Journal of Otology, vol. 21, No. 2, Mar. 2000, pp. 196-204 [Abstract Only].
Zorman, CH., "Silicon Carbide as a material for Biomedical Microsystems", EDA Publishing Association, 2009, 8 pages.
U.S. Appl. No. 16/380,944, filed Apr. 10, 2019, Maharbiz et al.
U.S. Appl. No. 16/398,086, filed Apr. 29, 2019, Maharbiz et al.
U.S. Appl. No. 16/401,028, filed May 1, 2019, Maharbiz et al.
U.S. Appl. No. 16/401,041, filed May 1, 2019, Maharbiz et al.
U.S. Office Action dated Oct. 24, 2019 issued in U.S. Appl. No. 16/398,086.
U.S. Office Action dated Nov. 15, 2019 issued in U.S. Appl. No. 16/401,028.
U.S. Office Action dated Sep. 18, 2019 issued in U.S. Appl. No. 16/380,944.
U.S. Notice of Allowance dated Dec. 17, 2019 issued in U.S. Appl. No. 16/380,944.
U.S. Notice of Allowance dated Feb. 11, 2020 issued in U.S. Appl. No. 16/398,086.
U.S. Appl. No. 16/739,084, filed Jan. 9, 2020, Maharbiz et al.
U.S. Notice of Allowance dated Jan. 10, 2020 issued in U.S. Appl. No. 16/401,028.
U.S. Office Action dated Jan. 9, 2020 issued in U.S. Appl. No. 16/401,041.

Interrogator Transducer

FIG. 5A
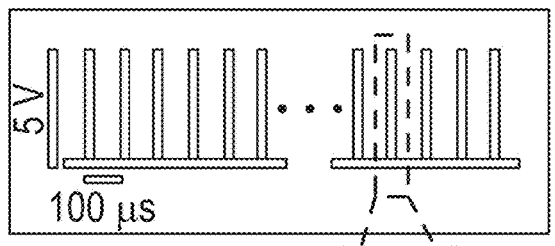
FIG. 5C
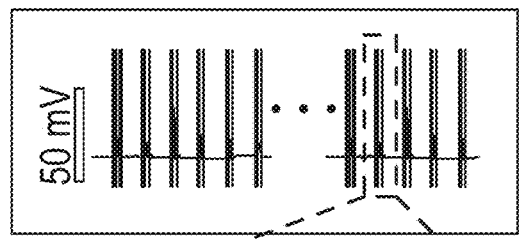
FIG. 5B
FIG. 5E
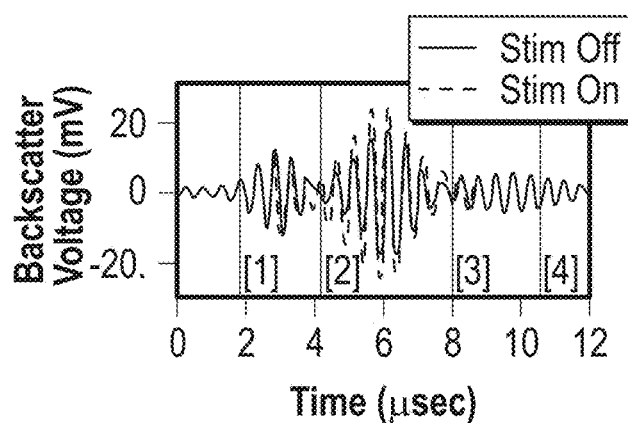
FIG. 5D
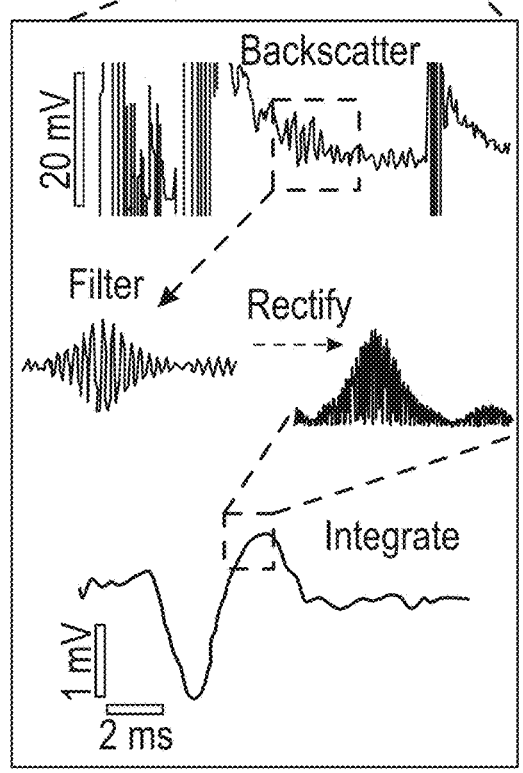
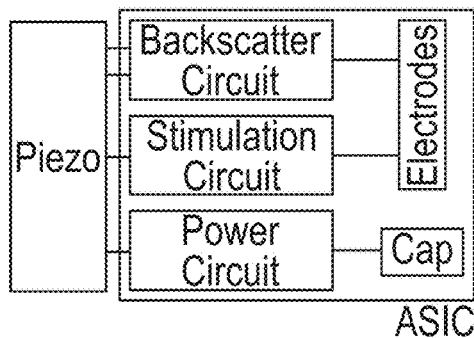
FIG. 6

1. Start w/SCS

2. Spin PI Layer

3. PECVD a-SIC

4. RIE Openings for Electrodes

5. Evaporate Ruthenium and Plate Gold onto Electrode Sites

6. Die/Piezo Attach and Wirebond

7. PECVD a-SIC Encapsulation

8. RIE Emboss Topside, Remove Film from Backside

9. Dissolve Wafer (TMAH)

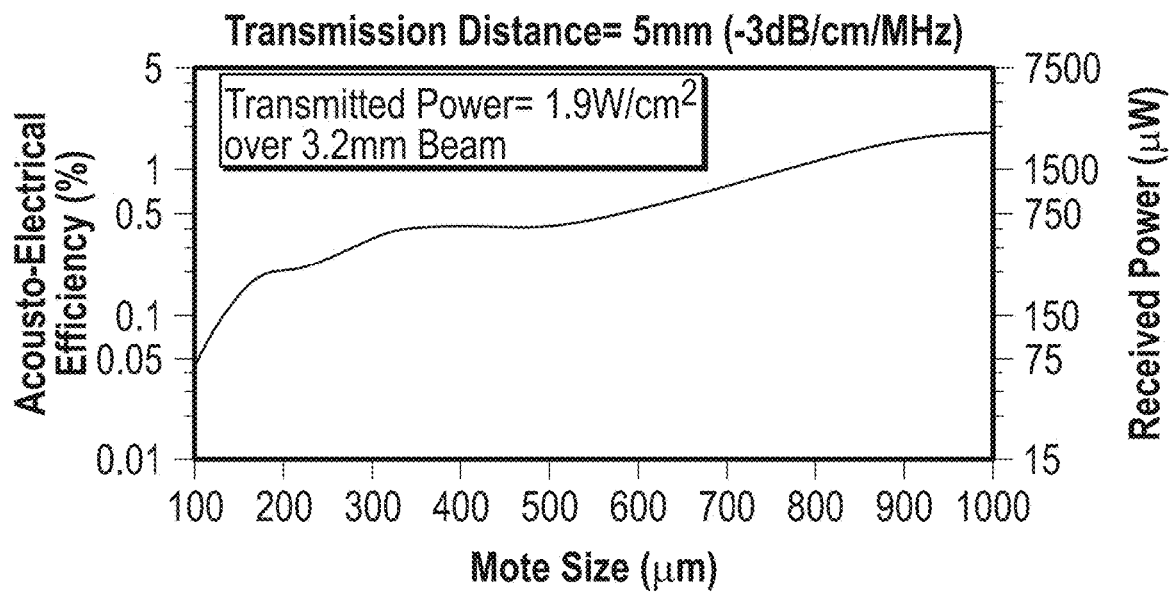
FIG. 28
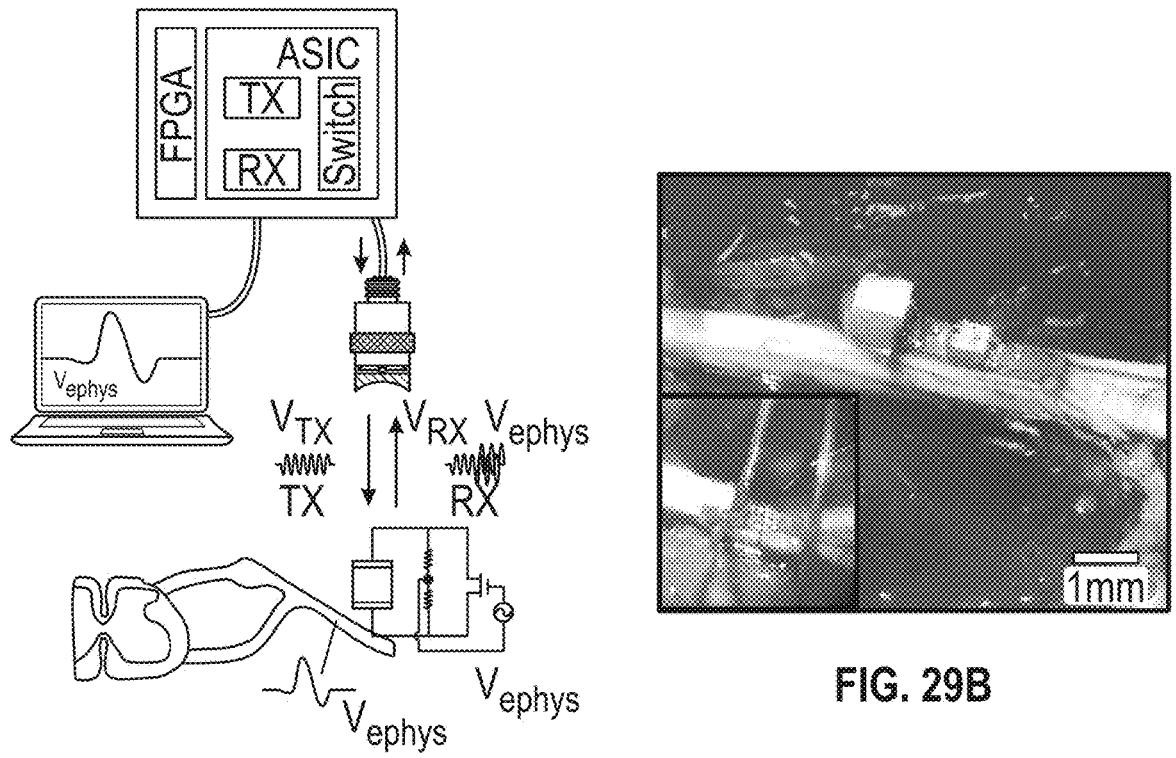
FIG. 29A
FIG. 29B

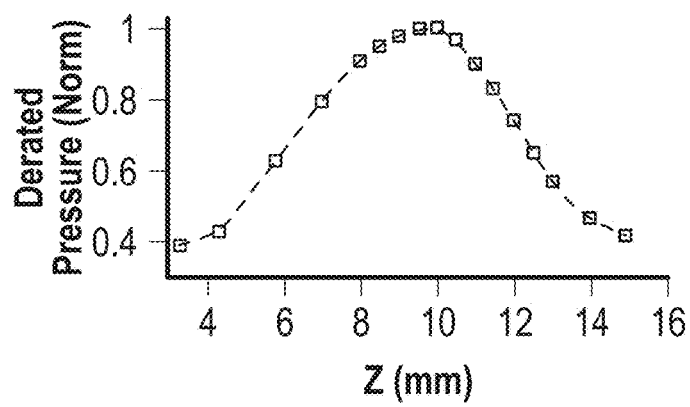
FIG. 31A
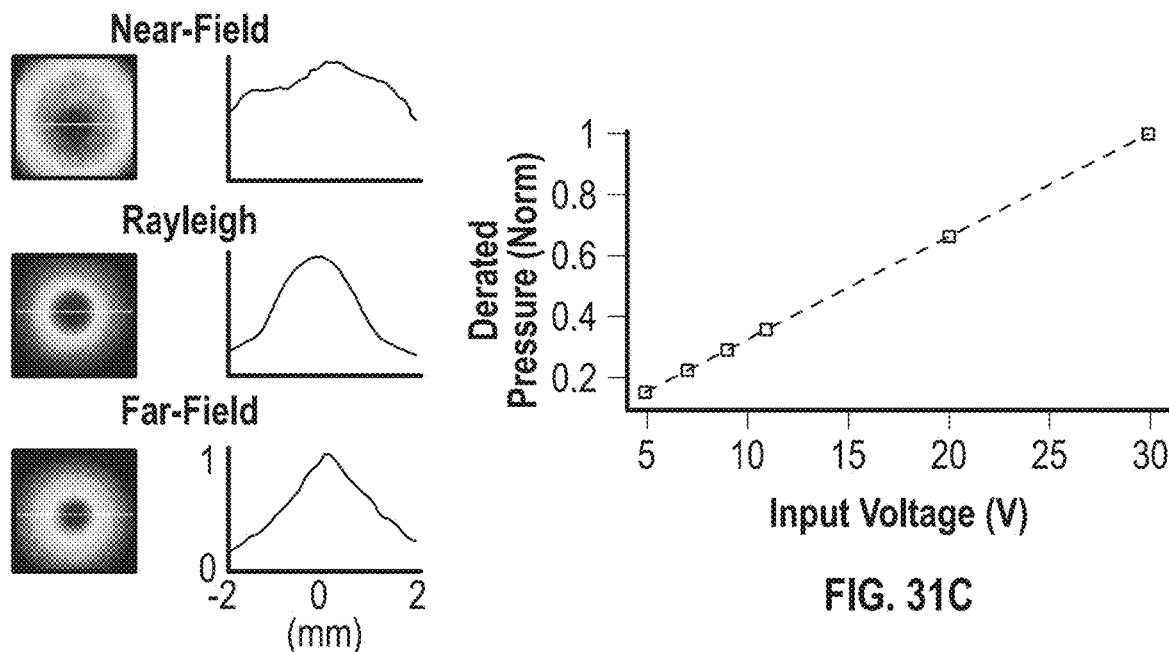
FIG. 31B
FIG. 31C
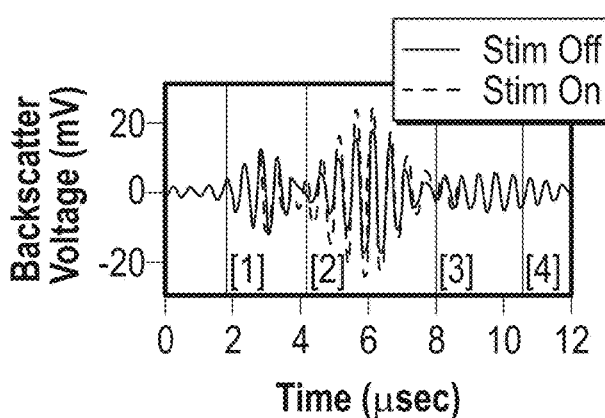
FIG. 31D
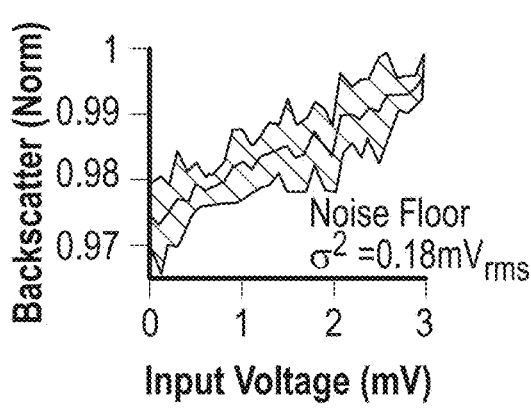
FIG. 31E

IMPLANTS USING ULTRASONIC WAVES FOR STIMULATING TISSUE

CROSS-REFERENCE TO RELATED APPLICATION

This application is a continuation of U.S. Non-Provisional application Ser. No. 16/313,865, filed on Dec. 27, 2018, which is a U.S. National Phase Application of International Application No. PCT/US2017/041264, filed Jul. 7, 2017, which claims priority to U.S. Provisional Application No. 62/359,672, filed on Jul. 7, 2016, entitled "NEURAL DUST AND ULTRASONIC BACKSCATER IMPLANTS AND SYSTEMS, AND APPLICATIONS FOR SUCH SYSTEMS," the disclosure of each of which is incorporated herein by reference in its entirety and for all purposes.

STATEMENT AS TO FEDERALLY SPONSORED RESEARCH

This invention was made with government support under HR0011-15-2-0006 awarded by the Defense Advanced Research Projects Agency. The government has certain rights in the invention.

TECHNICAL FIELD

The present invention relates to implantable devices operated using ultrasonic waves for emitting an electrical pulse or stimulating tissue.

BACKGROUND

The emerging field of bioelectronic medicine seeks methods for deciphering and modulating electrophysiological activity in the body to attain therapeutic effects at target organs. Current approaches to interfacing with peripheral nerves, the central nervous system and/or muscles rely heavily on wires, creating problems for chronic use, while emerging wireless approaches lack the size scalability necessary to interrogate small-diameter nerves. Furthermore, conventional electrode-based technologies lack the capability to record from nerves with high spatial resolution or to record independently from many discrete sites within a nerve bundle.

Recent technological advances and fundamental discoveries have renewed interest in implantable systems for interfacing with the peripheral nervous system. Early clinical successes with peripheral neurostimulation devices, such as those used to treat sleep apnea or control bladder function in paraplegics have led clinicians and researchers to propose new disease targets ranging from diabetes to rheumatoid arthritis. However, currently known neurostimulation devices are generally fully external devices and unable to stimulate deep tissue, not fully implantable, or are unable to accurately stimulate a nerve without risking off-target stimulation.

SUMMARY OF THE INVENTION

Provided herein are implantable devices configured to emit an electrical pulse to a tissue, systems comprising an implantable device and an interrogator to operate the implantable device, and closed-loop systems comprising a first device configured to detect a physiological system and an implantable device configured to emit an electrical pulse to a tissue in response to an interrogator receiving the physiological signal. Further provided are computer systems configured to operate one or more implantable devices. Also provided are methods of stimulating a tissue.

In some embodiments, there is provided an implantable device, comprising an ultrasonic transducer configured to receive ultrasonic waves that power the implantable device and encode a trigger signal; a first electrode and a second electrode configured to be in electrical communication with a tissue and emit an electrical pulse to the tissue in response to the trigger signal; and an integrated circuit comprising an energy storage circuit. In some embodiments, the electrical pulse is a current pulse. In some embodiments, the electrical pulse is a voltage pulse.

In some embodiments, the first electrode and the second electrode are within the tissue or in contact with the tissue. In some embodiments, the tissue is muscle tissue, organ, or nervous tissue. In some embodiments, the tissue is part of the peripheral nervous system or the central nervous system. In some embodiments, the tissue is a skeletal muscle, smooth muscle, or cardiac muscle.

In some embodiments, the integrated circuit comprises a digital circuit. In some embodiments, the integrated circuit comprises a mixed-signal integrated circuit configured to operate the first electrode and the second electrode. In some embodiments, the integrated circuit comprises a power circuit comprising the energy storage circuit.

In some embodiments, the implantable device comprises a body that comprises the ultrasonic transducer and the integrated circuit, wherein the body is about 5 mm or less in length in the longest dimension. In some embodiments, the body has a volume of about 5 $mm^3$ or less. In some embodiments, the implantable device comprises a non-responsive reflector.

In some embodiments, the implantable device comprises three or more electrodes.

In some embodiments, the integrated circuit comprises an analog-to-digital converter (ADC).

In some embodiments, the implantable device comprises a modulation circuit configured to modulate a current flowing through the ultrasonic transducer. In some embodiments, the modulated current encodes information, and the ultrasonic transducer is configured to emit ultrasonic waves encoding the information. In some embodiments, the information comprises a signal verifying that an electrical pulse was emitted by the implantable device, a signal indicating an amount of energy stored in the energy storage circuit, or a detected impedance. In some embodiments, the implantable device comprises a digital circuit configured to operate the modulation circuit. In some embodiments, the digital circuit is configured to transmit a digitized signal to the modulation circuit. In some embodiments, the digitized signal comprises a unique implantable device identifier.

In some embodiments, the ultrasonic transducer is configured to receive ultrasonic waves from an interrogator comprising one or more ultrasonic transducers. In some embodiments, the ultrasonic transducer is a bulk piezoelectric transducer, a piezoelectric micro-machined ultrasonic transducer (PMUT), or a capacitive micro-machined ultrasonic transducer (CMUT).

In some embodiments, the implantable device is implanted in a subject. In some embodiments, the subject is a human.

In some embodiments, the implantable device is at least partially encapsulated by a biocompatible material. In some embodiments, at least a portion of the first electrode and the second electrode are not encapsulated by the biocompatible material.

Also provided herein is a system comprising one or more implantable devices and an interrogator comprising one or more ultrasonic transducers configured to transit ultrasonic waves to the one or more implantable devices, wherein the ultrasonic waves power the one or more implantable devices. In some embodiments, the ultrasonic waves encode a trigger signal. In some embodiments, the system comprises a plurality of implantable devices. In some embodiments, the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator is configured to transit ultrasonic waves to the plurality of implantable devices or receive ultrasonic backscatter from the plurality of implantable devices using time division multiplexing, spatial multiplexing, or frequency multiplexing. In some embodiments, the interrogator is configured to be wearable by a subject.

Also provided herein is a closed-loop system, comprising (a) a first device configured to detect a signal; (b) an interrogator comprising one or more ultrasonic transducers configured to receive the ultrasonic backscatter encoding the electrophysiological signal and emit ultrasonic waves encoding a trigger signal; and (c) a second device configured to emit an electrical pulse in response to the trigger signal, wherein the second device is implantable, comprising an ultrasonic transducer configured to receive ultrasonic waves that power the second device and encode a trigger signal; a first electrode and a second electrode configured to be in electrical communication with a tissue and emit an electrical pulse to the tissue in response to the trigger signal; and an integrated circuit comprising an energy storage circuit. In some embodiments, the signal is an electrophysiological pulse, a temperature, a molecule, an ion, pH, pressure, strain, or bioimpedance.

In some embodiments of the closed-loop system, the first device is implantable. In some embodiments, the first device comprises a sensor configured to detect the signal; an integrated circuit comprising a modulation circuit configured to modulate a current based on the detected signal, and a first ultrasonic transducer configured to emit an ultrasonic backscatter encoding the detected signal from the tissue based on the modulated current. In some embodiments, the sensor comprises a first electrode and a second electrode configured to be in electrical communication with a second tissue. In some embodiments, the first tissue and the second tissue are the same tissue. In some embodiments, the first tissue and the second tissue are different tissues.

In some embodiments of the closed-loop system, the first electrode and the second electrode of the second device are within the tissue or contact the tissue. In some embodiments, the integrated circuit of the second device comprises a digital circuit. In some embodiments, the integrated circuit of the second device comprises a mixed-signal integrated circuit configured to operate the first electrode and the second electrode. In some embodiments, the integrated circuit comprises a power circuit comprising the energy storage circuit.

In some embodiments of the closed-loop system, the tissue is muscle tissue, an organ, or nervous tissue. In some embodiments, the first device and the second device are implanted in a subject. In some embodiments, the subject is a human.

Further provided herein is a computer system, comprising an interrogator comprising one or more ultrasonic transducers; one or more processors; non-transitory computer-readable storage medium storing one or more programs configured to be executed by the one or more processors, the one or more programs comprising instructions for operating the interrogator to emit ultrasonic waves encoding a trigger signal that signals an implantable device to emit an electrical pulse to a tissue. In some embodiments, the interrogator is operated to emit ultrasonic waves encoding the trigger signal in response to a detected physiological signal. In some embodiments, the physiological signal comprises an electrophysiological pulse, a temperature, a molecule, an ion, pH, pressure, strain, or bioimpedance. In some embodiments, the one or more programs comprise instructions for detecting the physiological signal based on ultrasonic backscatter encoding the physiological signal emitted from a second implantable device. In some embodiments, the one or more programs comprise instructions for determining a location or movement of the first implantable device or the second implantable device relative to the one or more ultrasonic transducers of the interrogator.

Also provided herein is a method of electrically stimulating a tissue, comprising receiving ultrasonic waves at one or more implantable devices; converting energy from the ultrasonic waves into an electrical current that charges an energy storage circuit; receiving a trigger signal encoded in the ultrasonic waves at the one or more implantable devices; and emitting an electrical pulse that stimulates the tissue in response to the trigger signal. In some embodiments, the trigger signal is transmitted in response to a detected physiological signal.

Further provided is a method of electrically stimulating a tissue, comprising emitting ultrasonic waves encoding a trigger signal from an interrogator comprising one or more ultrasonic transducers to one or more implantable devices configured to emit an electrical pulse to the tissue in response to receiving the trigger signal. In some embodiments, the trigger signal is transmitted in response to a detected physiological signal.

Also provided herein is a method of stimulating a tissue, comprising receiving ultrasonic waves at one or more implantable devices configured to detect a physiological signal; converting energy from the ultrasonic waves into an electrical current that flows through a modulation circuit; detecting the physiological signal; modulating the electrical current based on the detected physiological signal; transducing the modulated electrical current into an ultrasonic backscatter that encodes information related to the detected physiological signal; and emitting the ultrasonic backscatter to an interrogator comprising one or more transducer configured to receive the ultrasonic backscatter; emitting ultrasonic waves from the interrogator to one or more implantable devices configured to emit an electrical pulse to the tissue; converting energy from the ultrasonic waves emitted from the interrogator to the one or more implantable devices configured to emit the electrical pulse into an electrical current that charges an energy storage circuit; emitting ultrasonic waves encoding a trigger signal from the interrogator; receiving the trigger signal at the one or more implantable devices configured to emit the electrical pulse; and emitting an electrical pulse that stimulates the tissue in response to the trigger signal.

In some embodiments of the method of stimulating a tissue, the physiological signal comprises an electrophysiological pulse, a temperature, a molecule, an ion, pH, pressure, strain, or bioimpedance.

In some embodiments of the method of stimulating a tissue, the tissue is a muscle tissue, an organ, or a nervous tissue.

In some embodiments of the method of stimulating a tissue, the method comprises implanting the one or more implantable devices in a subject. In some embodiments, the subject is a human.

In some embodiments of the method of stimulating a tissue, the method comprises determining a location or movement of the one or more implantable devices.

BRIEF DESCRIPTION OF THE FIGURES

FIG. 5A shows a series of cycles of ultrasonic wave pulses emitted by an interrogator. Upon receiving a trigger from the interrogator (e.g., an FPGA), the transceiver board of the interrogator generates a series of transmit pulses. At the end of the transmit cycle, the switch on the ASIC disconnects the transmit module and connects the receive module. The cycles have a frequency of every 100 microseconds. FIG. 5B shows a zoomed-in view of the transmit pulse sequence (i.e., one cycle) shown in FIG. 5A, with the cycle having six pulses of ultrasonic waves at 1.85 MHz, the pulses recurring every 540 nanoseconds. FIG. 5C shows ultrasonic backscatter emitted by an implantable device. The ultrasonic backscatter reaches the transducer of the interrogator approximately $2t_{Rayleigh}$. FIG. 5D shows a zoomed-in view of the ultrasonic backscatter, which can be analyzed. Analysis of the ultrasonic backscatter can include filtering, rectifying and integrating the ultrasonic backscatter waves. FIG. 5E shows a zoomed in view of the filtered ultrasonic backscatter waves. The backscatter wave includes responsive regions, which are responsive to changes in impedance to the miniaturized ultrasonic transducer, and non-responsive regions that are not responsive to changes in impedance to the miniaturized ultrasonic transducer.

FIG. 6 illustrates one embodiment of an implantable device with a miniaturized ultrasonic transducer (identified as the "piezo") connected to an ASIC. The ASIC includes a power circuit, a stimulation circuit (which operates the implantable device to emit the stimulating electrical pulse), and a modulation circuit (or "backscatter circuit"). The power circuit includes an energy storage capacitor ("cap"). The electrodes can be implanted in tissue.

FIG. 28 shows a simulated scaling of miniaturized ultrasonic transducer link efficiency and received power at 5 mm in tissue.

FIGS. 29A-29D provide an overview of an exemplary system comprising an implantable device. FIG. 29A shows an external transducer powering and communicating an implantable device placed remotely in the body. Driven by a custom transceiver board, the transducer alternates between transmitting a series of pulses that power the device and listening for reflected pulses that are modulated by electrophysiological signals. FIG. 29B shows an implantable device anchored to the sciatic nerve in an anesthetized rat. The insert in FIG. 29B shows an implantable device with optional testing leads. FIG. 29C shows components of an exemplary implantable device. The implantable device was assembled on a flexible PCB and included a piezoelectric crystal, a single custom transistor, and a pair of recording electrodes. FIG. 29D shows a close up of an implantable device on a flexible PCG with calibration leads to measure electrophysiological signal (ground truth) and voltages harvested on the piezocrystal. During in-vivo experiments, the calibration leads were removed.

FIG. 31A shows de-rated, normalized peak pressure as a function of distance from the surface of an interrogator transducer showed a de-rated focus at ~8.9 mm at 1.85 MHz. FIG. 31B shows XY cross-sectional beampatterns and the corresponding 1-D voltage plot at y=0 at near-field, Rayleigh distance, and far-field showed beam focusing at the Rayleigh distance. FIG. 31C shows that the transducer's output pressure was a linear function of input voltage (up to 32 V peak-to-peak). FIG. 31D (reproduction of FIG. 5E) shows exemplary backscatter waveform showing different regions of backscatter. The backscatter waveform is found flanked (in time) by regions which correspond to reflections arising from non-responsive regions; these correspond to reflected pulses from other device components. The measurement from the nonresponsive regions, which do not encode biological data) can be used as a reference. As a result of taking this differential measurement, any movements of the entire structure relative to the external transducer during the experiment can be subtracted out. FIG. 31E shows a calibration curve obtained in the custom water tank setup showed the noise floor of 0.18 mVrms.

DETAILED DESCRIPTION OF THE INVENTION

Figure 1:
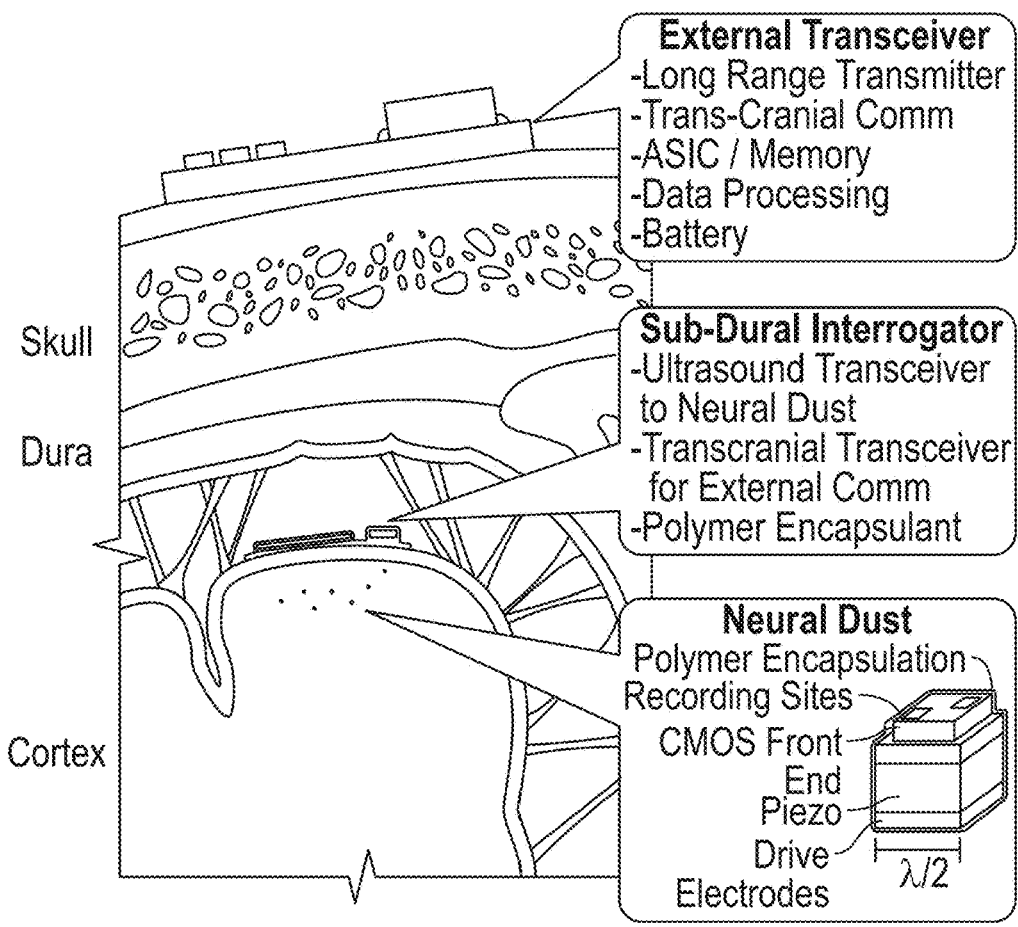
FIG. 1 is a schematic of a neural dust system, including an external transceiver, a sub-dural interrogator, and a neural dust mote, as described in Seo et al., *Neural dust: an ultrasonic, low power solution for chronic brain-machine interfaces*, arXiv: 1307.2196v1 (Jul. 8, 2013).

The implantable device described herein includes a miniaturized ultrasonic transducer (such as a miniaturized piezoelectric transducer) configured to receive ultrasonic waves that power the implantable device, a power circuit comprising an energy storage circuit, and two or more electrodes configured to emit an electrical pulse. The implantable device can also include a digital circuit or a mixed-signal integrated circuit configured to operate the electrodes. The implantable device can be implanted in a subject such that the electrodes engage a tissue, such as nervous tissue, muscle tissue, or an organ, and can emit an electrical pulse to stimulate the tissue. The miniaturized ultrasonic transducer receives ultrasonic energy from an interrogator (which may be external or implanted), which powers the implantable device. The interrogator includes a transmitter configured to transmit the ultrasonic waves to the implantable device. In some embodiments, the interrogator comprises a receiver, which may be integrated with the transmitter into a combined transceiver, and the receiver and the transmitter may be disposed on the same device or on different devices. Mechanical energy from the ultrasonic waves transmitted by the interrogator vibrates the miniaturized ultrasonic transducer on the implantable device, which generates an electrical current. Energy from the electrical current can be stored in the energy storage circuit, which can include one or more capacitors. The interrogator can encode a trigger signal in the ultrasonic waves that are transmitted to the implantable device, and, upon receipt of the trigger signal, the implantable device emits an electrical pulse (for example, by discharging all or a portion of the energy stored in the energy storage circuit). The trigger signal can be encoded, for example, at a predetermined signal or in response to some other signal (such as a detected electrophysiological signal in a closed-loop system). The implantable device can include a digital circuit, which is configured to decipher the encoded trigger signal, and operate the energy storage circuit and electrodes to discharge the electrical pulse.

The implantable device or electrodes form the implantable device engage the tissue to emit the stimulatory electrical pulse. In some embodiments, the tissue is a nervous tissue (such as tissue in the central nervous system or peripheral nervous system), muscle tissue (such as smooth muscle, skeletal muscle, or cardiac muscle), or an organ (such as a large or small intestine, stomach, kidney, a secretory gland (such as a salivary gland or mammary gland) or a bladder). In some embodiments, engagement of the tissue is such that the implantable device does not completely surround the tissue. In some embodiments, the implantable device is on, implanted in, or adjacent to the tissue. In some embodiments, the electrodes of the implantable device engage the tissue. For example, the electrodes can be on or implanted in the nervous tissue (for example, by penetrating the epineurium), muscle tissue, or an organ. In some embodiments, the one or more electrodes include a cuff electrode, which can partially surround the tissue. In some embodiments, the implantable device is located near the tissue, and electrodes can extend from the implantable device to reach the tissue.

The nervous tissue can be part of the central nervous system (such as the brain (e.g., cerebral cortex, basal ganglia, midbrain, medulla, pons, hypothalamus, thalamus, cerebellum, pallium, or hippocampus) or the spinal cord), or part of the peripheral nervous system (such as a nerve, which may be a somatic nerve or a nerve in the automatic nervous system). Exemplary nerves include the sciatic nerve, the vagus nerve, vagus nerve branches, the tibial nerve, the spenic nervie, the splanchnic nerve, the pudendal nerve, the sacral nerve, the supraorbital nerve, and the occipital nerve. The muscle tissue can be, for example, skeletal muscle, smooth muscle, or cardiac muscle. Exemplary muscles include the gastrocnemius muscle, pelvic floor muscles, gastric smooth muscle, and cardiac muscle.

The implantable devices described herein can be implanted in or used in a subject (i.e., an animal). In some embodiments, the subject is a mammal. Exemplary subjects include a rodent (such as a mouse, rat, or guinea pig), cat, dog, chicken, pig, cow, horse, sheep, rabbit, bird, bat, monkey etc. In some embodiments, the subject is a human.

The electrical pulse can be useful, for example, to control limbs (i.e., functional electrical stimulation), controlling bladder function, or for treating sleep apnea or rheumatoid arthritis. See, e.g., Tracey, *The inflammatory reflex*, Nature vol. 420, pp. 853-859 (2002).

Generally, in recent years, there has been growing interest in the use of neural recording and stimulation technologies to develop a new closed-loop neuromodulation therapy paradigm for disorders in the central and peripheral nervous systems. Because nerves carry both efferent and afferent signals to a variety of target organs, effective technologies will need high spatiotemporal resolution to record and stimulate from multiple sites. Additionally, in order for these technologies to become clinically viable, they will need to be tetherless to avoid potential infections and adverse biological responses due to externalized leads or micro-motion of the implant within the tissue. To address these issues, described herein is an ultrasonic backscatter system to wirelessly power and communicate with implantable devices. One of the strengths of the technology is that, unlike conventional radio frequency technology, ultrasound-based systems appear scalable down to millimeter size scales, or even smaller, and operate reliably at greater than several centimeters of implant depth, opening the door to a new technological path in implantable electronics.

In some embodiments, the can be used to record, stimulate, and/or block signals (e.g., electrophysiological signals) in the central or peripheral nervous system. Detected electrophysiological signals can be used to trigger and shape the parameters of therapeutic stimulation by providing detailed feedback about neural dynamics in real time, in the context of neurostimulation targets, such as treating sleep apnea or controlling bladder function to new disease targets ranging from diabetes to rheumatoid arthritis.

Further provided herein are methods to wirelessly power and communicate with implantable sensors, down to millimeter size scales or smaller, embedded up to several centimeters in tissue to enable continuous monitoring of body's important vital signs.

The implantable devices described herein can be powered and can communicate at depths that were not possible with earlier implantable systems. In some embodiments, an implantable device configured to detect an electrophysiological single includes a piezoelectric transducer, an application specific integrated circuit (ASIC), and a pair of recording electrodes. One embodiment of the implant utilizes a single bulk piezoelectric transducer, either recording or stimulation ASIC, and gold electrodes. Alternatively, the electrodes can be electroplated or electrochemically deposited with poly(3,4-ethylenectioxythiophene) (PEDOT), Pt, or Pt-black in order to improve the recording quality. Simultaneous multi-site recording or stimulation can be achieved by deploying a plurality of these motes at desired locations or placing multiple pairs of electrodes on the mote and using multiplexors on-chip. The data from different pairs of electrodes can be encoded in either amplitude, frequency, or phase modulated waveforms.

In some embodiments, an external unit can interrogate a single mote by employing a single transducer to transmit ultrasonic energy or interrogate multiple motes by employing beamforming arrays. The arrays can be based on an array of bulk piezoelectric transducers or capacitive or piezoelectric micro-machined ultrasonic transducers (CMUTs, PMUTs). Both PMUTs and CMUTs are micro-electro-mechanical systems (MEMS) devices manufactured using semiconductor batch fabrication, with each MUT capable of transmitting and receiving acoustic waves.

In some embodiments, during usage, the implantable device is placed either on, around, or in the target nerve with the electrode side in contact with the target nerve. Important connections can be routed out, either a straight or serpentine fashion, to 10 mil vias as test points. The length of the leads can be adjusted according to the application. Alternatively, components can be divided in half and assembled either on the top or the bottom side of the board, along with the electrodes, in order to minimize the overall size. Assembly of the double-sided platform can be more complex due to the necessary electrical and mechanical isolations between the ASIC and the piezoelectric transducer during wire-bonding or flip-chip bonding In some embodiments, the system is implemented as a closed-loop therapeutic medical system. Such a system can include an ultrasound transceiver configured to generate and receive ultrasound transmissions, and a body implantable device sized and configured to engage but not entirely surround a neural structure. The implantable device comprises a piezoelectric transducer and energy storage elements to harvest power necessary to operate stimulation ASIC. The implantable device comprises stimulation pulse generating circuitry and leads coupled to the pulse generating circuitry to produce stimulation pulses to electrically stimulate or block the neural structure. The implantable device further comprises an ultrasound backscatter communication system to communicate with external equipment via the ultrasound transceiver. In some embodiments, the system may include one or more of the following. The ultrasound transceiver may be additionally configured for body implantation. The system may further comprise external equipment communicatively coupled with the ultrasound transceiver. The external equipment may communicate wirelessly with the ultrasound transceiver. The body implantable device may further be configured to sense a biologic condition, and communicate data indicative of the sensed biologic condition to the external equipment. In such a case, the external equipment is configured to analyze sensed biologic condition data, and to initiate, where indicated by the analysis of the sensed biologic condition data, ultrasound communications to the implanted device to generate stimulation pulses to electrically stimulate or block the neural structure. In some embodiments, the external equipment directly detects the biological condition.

In some embodiments, the neural stimulation system may include multiple of the body implantable devices sized and configured to engage but not entirely surround a neural structure. The body implantable device may further be configured to communicate data indicative of device state to the external equipment. The body implantable device may be configured to communicate data indicative of device operation to the external equipment. In addition, the body implantable device may further be configured to record and report sensed biologic conditions to provide feedback to adjust stimulation parameters.

A significant advantage of the implantable device described herein is the ability to emit a stimulatory electrical pulse to nervous tissue or muscle tissue deep within a subject while being wirelessly powered. In some embodiments, the implantable device acts in a closed-loop system, and can emit a stimulatory electrical pulse in response to a detected electrophysiological pulse. Further, the implantable devices can remain in a subject for an extended period of time without needing to charge a battery or retrieve information stored on the device.

Electromagnetic (EM) power transfer is not a practical for powering small implantable devices due to power attenuation through tissue and the relatively large apertures (e.g. antennas or coils) required to capture such energy. See, for example, Seo et al., *Neural dust: an ultrasonic, low power solution for chronic brain-machine interfaces*, arXiv: 1307.2196v1 (Jul. 8, 2013). Use of EM to supply sufficient power to an implanted device would either require a shallow depth of the implant or would require excessive heating of the tissue to pass the EM waves through the tissue to reach the implantable device. In contrast to EM, ultrasonic power transfer provides low power attenuation in tissue due to the relatively low absorption of ultrasonic energy by tissue and the shorter wavelength of the ultrasonic waves (as compared to electromagnetic waves). Further, the shorter wavelengths provided by the ultrasonic waves provides high spatial resolution at lower frequencies compared to radio waves.

Ultrasonic transducers have found application in various disciplines including imaging, high intensity focused ultrasound (HIFU), nondestructive testing of materials, communication, and power delivery through steel walls, underwater communications, transcutaneous power delivery, and energy harvesting. See, e.g., Ishida et al., *Insole Pedometer with Piezoelectric Energy Harvester and 2 V Organic Circuits*, IEEE J. Solid-State Circuits, vol. 48, no. 1, pp. 255-264 (2013); Wong et al., *Advantages of Capacitive Micromachined Ultrasonics Transducers (CMUTs) for High Intensity Focused Ultrasound (HIFU)*, IEEE Ultrasonics Symposium, pp. 1313-1316 (2007); Ozeri et al., *Ultrasonic Transcutaneous Energy Transfer for Powering Implanted Devices*, Ultrasonics, vol. 50, no. 6, pp. 556-566 (2010); and Richards et al., *Efficiency of Energy Conversion for Devices Containing a Piezoelectric Component*, J. Micromech. Microeng., vol. 14, pp. 717-721 (2004). Unlike electromagnetics, using ultrasound as an energy transmission modality never entered into widespread consumer application and was often overlooked because the efficiency of electromagnetics for short distances and large apertures is superior. However, at the scale of the implantable devices discussed herein and in tissue, the low acoustic velocity allows operation at dramatically lower frequencies, and the acoustic loss in tissue is generally substantially smaller than the attenuation of electromagnetics in tissue.

The relatively low acoustic velocity of ultrasound results in substantially reduced wavelength compared to EM. Thus, for the same transmission distance, ultrasonic systems are much more likely to operate in the far-field, and hence obtain larger spatial coverage than an EM transmitter. Further, the acoustic loss in tissue is fundamentally smaller than the attenuation of electromagnetics in tissue because acoustic transmission relies on compression and rarefaction of the tissue rather than time-varying electric/magnetic fields that generate displacement currents on the surface of the tissue.

In addition to powering the implantable device, in some embodiments, the ultrasonic waves received by the implantable device can include a trigger signal. The trigger signal received by the miniaturized ultrasonic transducer on the implantable device, and is then encoded in the current generated by the transducer. The signal is then received by a digital signal, which can operate the energy storage circuit to release an electrical pulse transmitted by the electrode to the tissue. The trigger signal can be transmitted by the ultrasonic waves in response to an input signal, such as a user operated input signal, or can be responsive to a detected electrophysiological signal. For example, in some embodiments, the trigger signal is transmitted in response to an electrophysiological signal detected by an implantable device transmitted to the interrogator.

In some embodiments, a "neural dust" system comprises tiny body implantable devices referred to as neural dust or "motes", an implantable ultrasound transceiver that communicates with each of the motes using ultrasound transmissions and backscatter transmissions reflected from the motes, and an external transceiver that communicates wirelessly with the ultrasound transceiver. See Seo et al., *Neural dust: an ultrasonic, low power solution for chronic brain-machine interfaces*, arXiv: 1307.2196v1 (Jul. 8, 2013) ("Seo et al., 2013"); Seo et al., *Model validation of untethered, ultrasonic neural dust motes for cortical recording*, J. Neuroscience Methods, vol. 244, pp. 114-122 (2014) ("Seo et al., 2014"); and Bertrand et al., *Beamforming approaches for untethered, ultrasonic neural dust motes for cortical recording: a simulation study*, IEE EMBC, vol. 2014, pp. 2625-2628 (2014). The neural dust system described in these papers is used for cortical recording (i.e., the recording of brain electrical signals). In that application as shown in the papers, the motes are implanted in the brain tissue (cortex), the ultrasound transceiver is implanted below the dura, on the cortex, and the external transceiver is placed against the head of the patient proximate to where the sub-dural ultrasound transceiver is implanted, as shown in FIG. 1 from Seo et al., 2013.

Seo et al., 2013 and Seo et al., 2014 showed that, theoretically, the neural dust system could be used to develop small-scale implants (below the mm-scale) for wireless neural recording. Accurate detection of electrophysiological signals or stimulation of tissue using an electrical pulse is enhanced by accurate determination of the location or movement of the implantable device. This ensures accurate attribution of a detected signal to the tissue generating the signal, or accurate stimulation of targeted tissue, as well as filtering of signals that may be caused by movement. As described herein, location and movement of the implantable devices can be accurately determined by analyzing non-responsive ultrasonic backscatter. Further, it has been found that the implantable devices can transmit a digitized signal encoded in the ultrasonic backscatter. The digitized signal can allow for increased reliability of electrophysiological signal detection (for example, by filtering false positive signals), data compression (which can be particularly beneficial, for example, when the implantable device includes a plurality of electrodes), and can allow for the inclusion of unique identifier signals in the ultrasonic backscatter when utilizing a plurality of implantable devices or when the implantable devices include a plurality of electrodes.

Miniature, implantable systems that exist are either wired, which create problems for chronic, everyday use, or emerging wireless approaches based on electromagnetics struggle to power and communicate with implanted devices at sizes below the millimeter scale or embedded more than centimeters into the tissue while maintaining power levels within established safety limits. Compared to existing technologies, the proposed implant has the advantage of easy fabrication, integration, and scalability to dimensions and implant depth not achievable in the past.

In some embodiments, an implantable device useful in a close-loop system stimulates tissue (such as muscle tissue, nervous tissue, or an organ) in response to detected condition (such as an electrophysiological signal, a temperature, a concentration of an analyte (e.g., an ion, glucose, oxygen, etc) or other molecule (such as a neurotransmitter, a cytokine, a hormone, or other signaling molecule or protein), pH, pressure, strain, or bioimpedance) detected by the same or a different implantable device. The detected condition can be local or systemic. In some embodiments, the implantable device configured to detect an electrophysiological signal engages nervous tissue or muscle tissue, and can be used to report an electroneurogram or an electromyogram. In some embodiments, implantable devices can be configured to detect and report (via ultrasonic backscatter) information related to physiological conditions (such as temperature, pressure, pH, or analyte concentration; see International Patent Application titled "IMPLANTS USING ULTRASONIC BACKSCATTER FOR SENSING PHYSIOLGOICAL CONDITIONS," filed on Jul. 7, 2017, as PCT Application No. PCT/US2017/041257), radiation or radio-labeled cells and molecules (see International Patent Application titled "IMPLANTS USING ULTRASONIC BACKSCATTER FOR RADIATION DETECTION AND ONCOLOGY," filed on Jul. 7, 2017, as PCT Application No. PCT/US2017/041260), electrical impedance of tissue (see International Patent Application titled "IMPLANTS USING ULTRASONIC BACKSCATTER FOR SENSING ELECTRICAL IMPEDANCE OF TISSUE," filed on Jul. 7, 2017, as PCT Application No. PCT/US2017/041263), and an electrophysiological pulse (see International Patent Application titled "IMPLANTS USING UL MASONIC BACKSCATTER FOR DETECTING ELECTROPHYSIOLOGICAL SIGNALS," filed on Jul. 7, 2017, as PCT Application No. PCT/US2017/041262); each of these applications is incorporated herein by reference in their entirety for all purposes.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The term "miniaturized" refers to any material or component about 5 millimeters or less (such as about 4 mm or less, about 3 mm or less, about 2 mm or less, about 1 mm or less, or about 0.5 mm or less) in length in the longest dimension. In certain embodiments, a "miniaturized" material or component has a longest dimension of about 0.1 mm to about 5 mm (such as about 0.2 mm to about 5 mm, about 0.5 mm to about 5 mm, about 1 mm to about 5 mm, about 2 mm to about 5 mm, about 3 mm to about 5 mm, or about 4 mm to about 5 mm) in length. "Miniaturized" can also refer to any material or component with a volume of about 5 $mm^3$ or less (such as about 4 $mm^3$ or less, 3 $mm^3$ or less, 2 $mm^3$ or less, or 1 $mm^3$ or less). In certain embodiments, a "miniaturized" material or component has a volume of about 0.5 $mm^3$ to about 5 $mm^3$, about 1 $mm^3$ to about 5 $mm^3$, about 2 $mm^3$ to about 5 $mm^3$, about 3 $mm^3$ to about 5 $mm^3$, or about 4 $mm^3$ to about 5 $mm^3$.

A "piezoelectric transducer" is a type of ultrasonic transceiver comprising piezoelectric material. The piezoelectric material may be a crystal, a ceramic, a polymer, or any other natural or synthetic piezoelectric material.

A "non-responsive" ultrasonic wave is an ultrasonic wave with a reflectivity independent of a detected signal. A "non-responsive reflector" is a component of an implantable device that reflects ultrasonic waves such that the reflected waveform is independent of the detected signal.

The term "subject" refers to an animal.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features.

The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein. Further, sectional headings are provide for organizational purposes and are not to be considered limiting. Finally, the entire disclosure of the patents and publications referred in this application are hereby incorporated herein by reference for all purposes.

Interrogator

The interrogator can wirelessly communicate with one or more implantable devices using ultrasonic waves, which are used to power and/or operate the implantable device. The ultrasonic waves emitted by the interrogator can encode a trigger signal, which signals the implantable device to emit an electrical pulse. The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. In some embodiments, transducers in the array can have regular spacing, irregular spacing, or be sparsely placed. In some embodiments the array is flexible. In some embodiments the array is planar, and in some embodiments the array is non-planar. In some embodiments, the ultrasound transmitting function is separated from the ultrasound receiving function on separate devices. That is, optionally, the interrogator comprises a first device that transmits ultrasonic waves to the implantable device, and a second device that receives ultrasonic backscatter from the implantable device.

In some embodiments, the interrogator can receive ultrasonic backscatter from an implantable device, such an implantable device configured to detect an electrophysiological voltage and emit ultrasonic backscatter which encodes information indicative of the detected electrophysiological voltage signal. In some embodiments, the trigger signal encoded by the ultrasonic waves emitted from the interrogator and received by the implantable device configured to emit an electrical pulse is transmitted in response to a received ultrasonic backscatter encoding information regarding the detected electrophysiological signal.

Figure 2A:
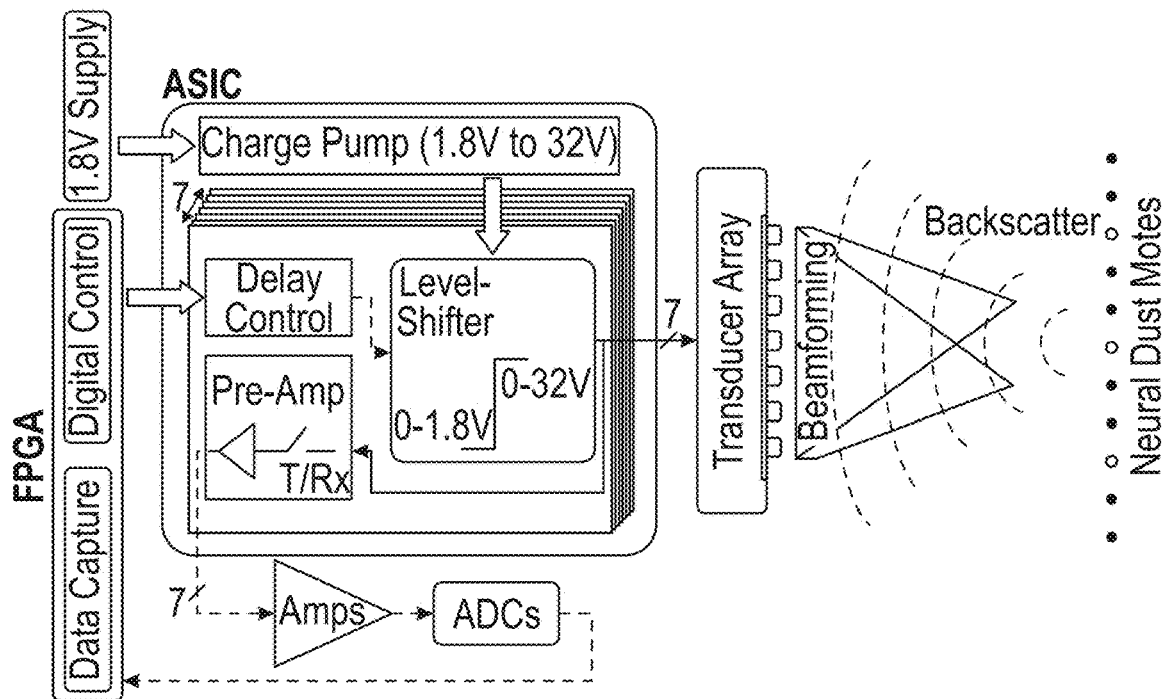
FIG. 2A is a block diagram of an exemplary interrogator for a system described herein. The illustrated interrogator includes an ultrasonic transducer array comprising a plurality of ultrasonic transducers. Each of the ultrasonic transducers in the array is operated by a channel, which includes a switch to alternatively configure the transducer to receive or transmit ultrasonic waves.

An exemplary interrogator is shown in FIG. 2A. The illustrated interrogator shows a transducer array with a plurality of ultrasonic transducers. In some embodiments, the transducer array includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more or more transducers. In some embodiments, the transducer array includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer transducers. The transducer array can be, for example a chip comprising 50 or more ultrasonic transducer pixels. The interrogator shown in FIG. 2A illustrates a single transducer array; however the interrogator can include 1 or more, 2 or more, or 3 or more separate arrays. In some embodiments, the interrogator includes 10 or fewer transducer arrays (such as 9, 8, 7, 6, 5, 4, 3, 2, or 1 transducer arrays). The separate arrays, for example, can be placed at different points of a subject, and can communicate to the same or different implantable devices. In some embodiments, the arrays are located on opposite sides of an implantable device. The interrogator can include an ASIC, which includes a channel for each transducer in the transducer array. In some embodiments, the channel includes a switch (indicated in FIG. 2A by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit. In some embodiments, the transducer connected to the channel is configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. In some embodiments, the data representing the wave shape and frequency for each channel can be stored in a 'wave table'. This allows the transmit waveform on each channel to be different. Then, delay control and level shifters can be used to 'stream' out this data to the actual transmit signals to the transducer array. In some embodiments, the transmit waveform for each channel can be produced directly by a high-speed serial output of a microcontroller or other digital system and sent to the transducer element through a level shifter or high-voltage amplifier. In some embodiments, the ASIC includes a charge pump (illustrated in FIG. 2A) to convert a first voltage supplied to the ASIC to a higher second voltage, which is applied to the channel. The channels can be controlled by a controller, such as a digital controller, which operates the delay control. In the ultrasound receiving circuit, the received ultrasonic waves are converted to current by the transducers (set in a receiving mode), which is transmitted to a data capture circuit. In some embodiments, an amplifier, an analog-to-digital converter (ADC), a variable-gain-amplifier or a time-gain-controlled variable-gain-amplifier (which can compensate for tissue loss), and/or a band pass filter is included in the receiving circuit. The ASIC can draw power from a power supply, such as a battery (which is preferred for a wearable embodiment of the interrogator). In the embodiment illustrated in FIG. 2A, a 1.8V supply is provided to the ASIC, which is increased by the charge pump to 32V, although any suitable voltage can be used. In some embodiments, the interrogator includes a processor and or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, the transducer array contains more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

Figure 2B:
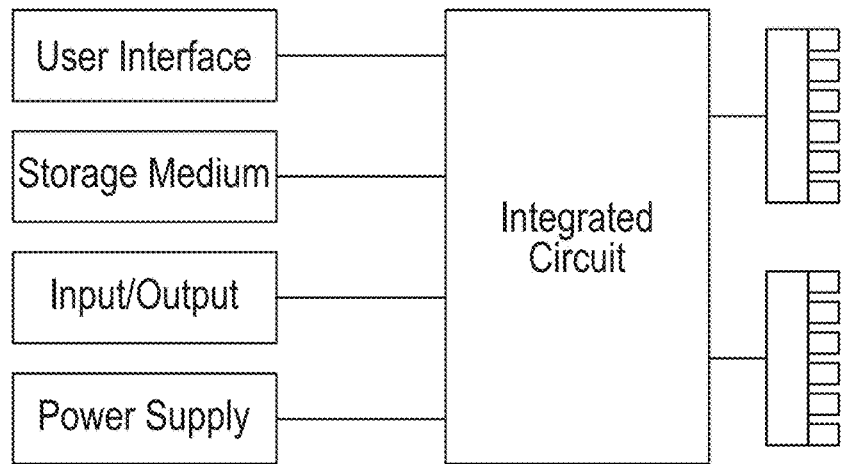
FIG. 2B is a schematic of another exemplary interrogator for a system described herein. The illustrated interrogator includes two ultrasonic transducer arrays, with each ultrasonic transducer array including a plurality of ultrasonic transducers. The interrogator also includes an integrated circuit (which can include a digital circuit, which can include a processor). The integrated circuit is connected to a user interface (which can include a display, keyboard, buttons, etc.), a storage medium (i.e., a non-transitory memory), an input/output (which may be wireless, such as a Bluetooth), and a power supply (such as a battery).

FIG. 2B illustrates another embodiment of interrogator. As shown in FIG. 2B, the interrogator includes one or more transducers 202. Each transducer 202 is connected to a transmitter/receiver switch 204, which can alternatively configure the transducer to transmit or receive ultrasonic waves. The transmitter/receiver switch is connected to a processor 206 (such as a central processing unit (CPU), a custom dedicated processor ASIC, a field programmable gate array (FPGA), microcontroller unit (MCU), or a graphics processing unit (GPU)). In some embodiments, the interrogator further includes an analog-digital converter (ADC) or digital-to-analog converter (DAC). The interrogator can also include a user interface (such as a display, one or more buttons to control the interrogator, etc.), a memory, a power supply (such as a battery), and/or an input/output port (which may be wired or wireless).

In some embodiments, the interrogator is implantable. An implanted interrogator may be preferred when the implantable devices are implanted in a region blocked by a barrier that does not easily transmit ultrasonic waves. For example, the interrogator can be implanted subcranially, either subdurally or supradurally. A subcranial interrogator can communicate with implantable devices that are implanted in the brain. Since ultrasonic waves are impeded by the skull, the implanted subcranial interrogator allows for communication with the implantable devices implanted in the brain. In another example, an implantable interrogator can be implanted as part of, behind or within another implanted device or prosthetic. In some embodiments, the implanted interrogator can communicate with and/or is powered by an external device, for example by EM or RF signals.

Figure 3A:
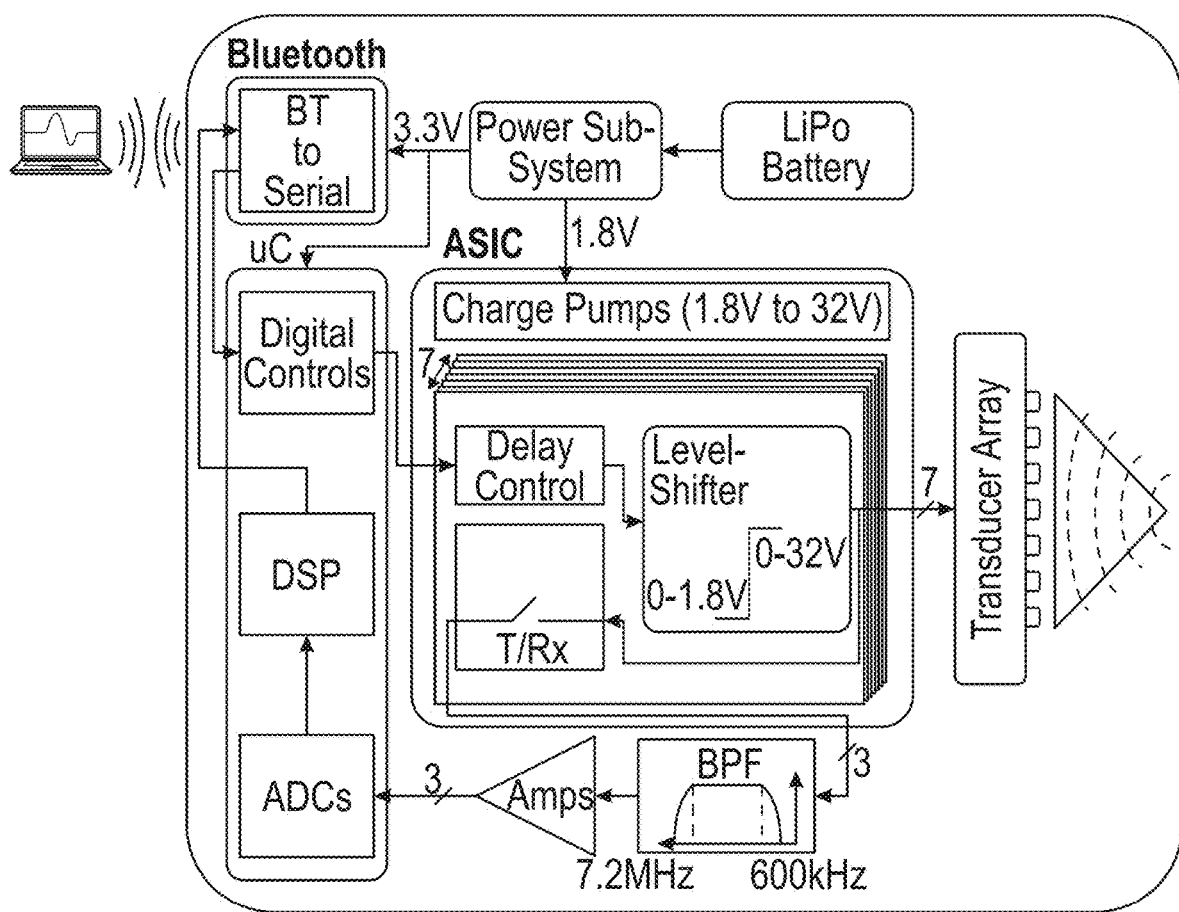
FIG. 3A shows a block diagram of an exemplary interrogator that can be worn by a subject. The interrogator includes a wireless communication system (a Bluetooth radio, in the illustration), which can be used to communicate with a computer system.
Figure 3B:
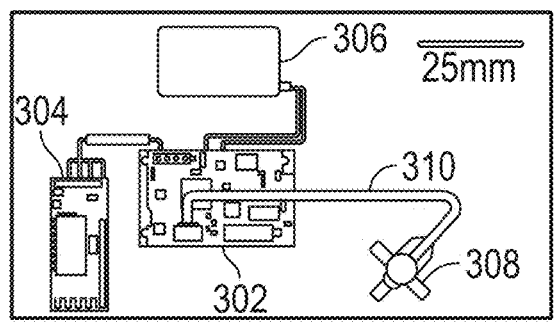
FIG. 3B shows an exploded view of a wearable interrogator. The interrogator includes a battery, a wireless communication system, and a transducer array.
Figure 3C:
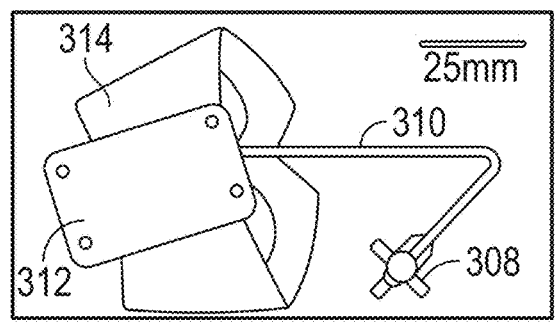
FIG. 3C shows the wearable interrogator shown in FIG. 3B fully assembled with a harness for attachment to a subject.
Figure 3D:
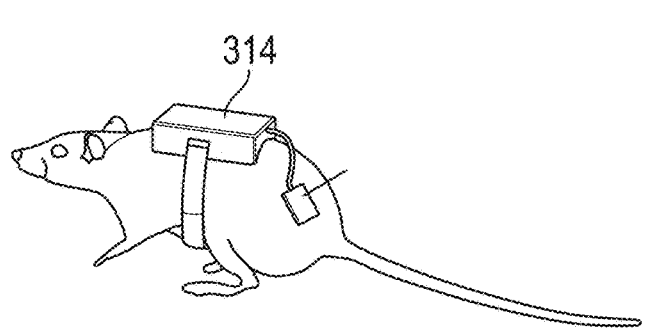
FIG. 3D illustrates the wearable interrogator attached a subject, namely a rodent (although could be any other animal, such as a human, dog, cat, horse, cow, pig, sheep, goat, chicken, monkey, rat, or mouse). The interrogator includes a transducer array, which is fixed to the body of the subject by an adhesive.
Figure 3E:
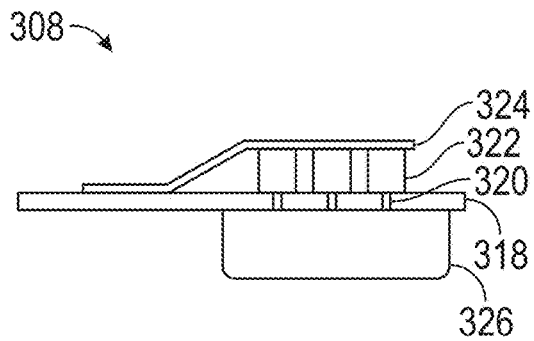
FIG. 3E illustrates a cross-section of the transducer array of the interrogator shown in FIGS. 3A-D.

In some embodiments, the interrogator is external (i.e., not implanted). By way of example, the external interrogator can be a wearable, which may be fixed to the body by a strap or adhesive. In another example, the external interrogator can be a wand, which may be held by a user (such as a healthcare professional). In some embodiments, the interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator. FIG. 3A-E shows an example of a wearable external interrogator. FIG. 3A shows a block diagram of the interrogator, which includes a transducer array comprising a plurality of transducers, an ASIC comprising a channel for each transducer in the transducer array, a battery (lithium polymer (LiPo) battery, in the illustrated example), and a wireless communication system (such as a Bluetooth system). FIG. 3B illustrates an exploded view of a wearable interrogator, including a printed circuit board (PCB) 302, which includes the ASIC, a wireless communication system 304, a battery 306, an ultrasonic transducer array 308, and a wire 310 tethering the ultrasonic transducer array 308 to the ASIC. FIG. 3C shows the wearable interrogator 312 shown in FIG. 3B with a harness 314, which can be used to attach the interrogator to a subject. FIG. 3D shows the assembled interrogator 316 attached to a subject, with the transducer array 308 attached at a first location, and the rest of the interrogator attached to a second location. FIG. 3E shows a cross-section schematic of an exemplary ultrasonic transducer array 308, which includes a circuit board 318, vias 320 attaching each transducer 322 to the circuit board 318, a metalized polyester film 324, and an absorptive backing layer 326. The metalized polyester film 324 can provide a common ground and acoustic matching for the transducers, while the absorptive backing layer 326 (such as tungsten powder filled polyurethane) can reduce ringing of the individual transducers.

The specific design of the transducer array depends on the desired penetration depth, aperture size, and the size of the transducers in the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and $\lambda$ is the wavelength of ultrasound in the propagation medium (i.e., the tissue). As understood in the art, the Rayleigh distance is the distance at which the beam radiated by the array is fully formed. That is, the pressure filed converges to a natural focus at the Rayleigh distance in order to maximize the received power. Therefore, in some embodiments, the implantable device is approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., *Beamforming Approaches for Untethered, Ultrasonic Neural Dust Motes for Cortical Recording: a Simulation Study*, IEEE EMBC (August 2014). In some embodiments, beam steering is performed by adjusting the power or phase of the ultrasonic waves emitted by the transducers in an array.

In some embodiments, the interrogator includes one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Communication Between an Implantable Device and an Interrogator

The implantable device and the interrogator wirelessly communicate with each other using ultrasonic waves. The implantable device receives ultrasonic waves from the interrogator through a miniaturized ultrasonic transducer on the implantable device. Vibrations of the miniaturized ultrasonic transducer on the implantable device generate a voltage across the electric terminals of the transducer, and current flows through the device, including, if present, an integrated circuit. The current can be used to charge an energy storage circuit, which can store energy to be used to emit an electrical pulse, for example after receiving a trigger signal. The trigger signal can be transmitted from the interrogator to the implantable device, signaling that an electrical pulse should be emitted. In some embodiments, the trigger signal includes information regarding the electrical pulse to be emitted, such as frequency, amplitude, pulse length, or pulse shape (e.g., alternating current, direct current, or pulse pattern). A digital circuit can decipher the trigger signal and operate the electrodes and electrical storage circuit to emit the pulse.

In some embodiments, ultrasonic backscatter is emitted from the implantable device, which can encode information relating to the implantable device or the electrical pulse emitted by the implantable device. For example, the ultrasonic backscatter can encode a verification signal, which verifies that electrical pulse was emitted. In some embodiments, an implantable device is configured to detect an electrophysiological signal, and information regarding the detected electrophysiological signal can be transmitted to the interrogator by the ultrasonic backscatter. To encode signals in the ultrasonic backscatter, current flowing through the miniaturized ultrasonic transducer is modulated as a function of the encoded information, such as a detected electrophysiological signal. In some embodiments, modulation of the current can be an analog signal, which may be, for example, directly modulated by the detected electrophysiological signal. In some embodiments, modulation of the current encodes a digitized signal, which may be controlled by a digital circuit in the integrated circuit. The backscatter is received by an external ultrasonic transceiver (which may be the same or different from the external ultrasonic transceiver that transmitted the initial ultrasonic waves). The information from the electrophysiological signal can thus be encoded by changes in amplitude, frequency, or phase of the backscattered ultrasound waves.

Figure 4:
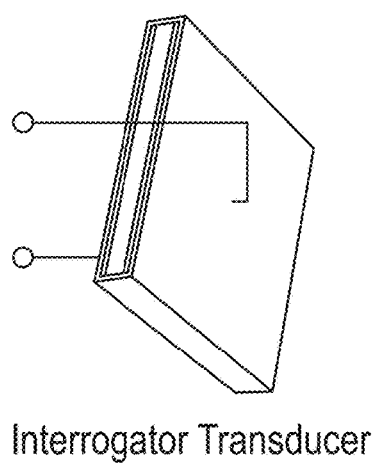
FIG. 4 provides a schematic showing the communication between a transducer from an interrogator and an implantable device having a miniaturized ultrasonic transducer. The interrogator transmits ultrasonic waves to the implantable device, and the miniaturized ultrasonic transducer emits ultrasonic backscatter modulated by the sensor. The backscatter is then received by the interrogator.
Figure 4:
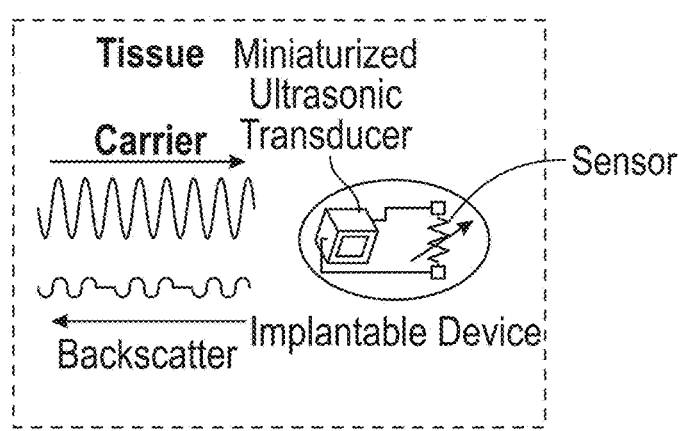

FIG. 4 illustrates an interrogator in communication with an implantable device. The external ultrasonic transceiver emits ultrasonic waves ("carrier waves"), which can pass through tissue. The carrier waves cause mechanical vibrations on the miniaturized ultrasonic transducer (e.g., a miniaturized bulk piezoelectric transducer, a PUMT, or a CMUT). A voltage across the miniaturized ultrasonic transducer is generated, which imparts a current flowing through an integrated circuit on the implantable device. The current flowing through to the miniaturized ultrasonic transducer causes the transducer on the implantable device to emit backscatter ultrasonic waves. In some embodiments, a detected electrophysiological signal either directly or indirectly (such as though an integrated circuit) modulates the current flowing through the miniaturized ultrasonic transducer, the backscatter waves encode information relating to the detected electrophysiological signal. The backscatter waves can be detected by the interrogator, and can be analyzed to recognize the electrophysiological signal detected by the implantable device.

Communication between the interrogator and the implantable device can use a pulse-echo method of transmitting and receiving ultrasonic waves. In the pulse-echo method, the interrogator transmits a series of interrogation pulses at a predetermined frequency, and then receives backscatter echoes from the implanted device. In some embodiments, the pulses are about 200 nanoseconds (ns) to about 1000 ns in length (such as about 300 ns to about 800 ns in length, about 400 ns to about 600 ns in length, or about 540 ns in length). In some embodiments, the pulses are about 100 ns or more in length (such as about 150 ns or more, 200 ns or more, 300 ns or more, 400 ns or more, 500 ns or more, 540 ns or more, 600 ns or more, 700 ns or more, 800 ns or more, 900 ns or more, 1000 ns or more, 1200 ns or more, or 1500 ns or more in length). In some embodiments, the pulses are about 2000 ns or less in length (such as about 1500 ns or less, 1200 ns or less, 1000 ns or less, 900 ns or less, 800 ns or less, 700 ns or less, 600 ns or less, 500 ns or less, 400 ns or less, 300 ns or less, 200 ns or less, or 150 ns or less in length). In some embodiments, the pulses are separated by a dwell time. In some embodiments, the dwell time is about 100 ns or more in length (such as about 150 ns or more, 200 ns or more, 300 ns or more, 400 ns or more, 500 ns or more, 540 ns or more, 600 ns or more, 700 ns or more, 800 ns or more, 900 ns or more, 1000 ns or more, 1200 ns or more, or 1500 ns or more in length). In some embodiments, the dwell time is about 2000 ns or less in length (such as about 1500 ns or less, 1200 ns or less, 1000 ns or less, 900 ns or less, 800 ns or less, 700 ns or less, 600 ns or less, 500 ns or less, 400 ns or less, 300 ns or less, 200 ns or less, or 150 ns or less in length). In some embodiments, the pulses are square, rectangular, triangular, sawtooth, or sinusoidal. In some embodiments, the pulses output can be two-level (GND and POS), three-level (GND, NEG, POS), 5-level, or any other multiple-level (for example, if using 24-bit DAC). In some embodiments, the pulses are continuously transmitted by the interrogator during operation. In some embodiments, when the pulses are continuously transmitted by the interrogator a portion of the transducers on the interrogator are configured to receive ultrasonic waves and a portion of the transducers on the interrogator are configured to transmit ultrasonic waves. Transducers configured to receive ultrasonic waves and transducers configured to transmit ultrasonic waves can be on the same transducer array or on different transducer arrays of the interrogator. In some embodiments, a transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period. In some embodiments, the one or more pulses in the cycle includes about 1 to about 10 pulses (such as about 2 to about 8, or about 4 to about 7, or about 6) pulses of ultrasonic waves in any given cycle. In some embodiments, the one or more pulses in the cycle includes about 1 or more, 2 or more, 4 or more, 6 or more, 8 or more, or 10 or more pulses of ultrasonic waves in any given cycle. In some embodiments, the one or more pulses in the cycle includes about 20 or fewer, about 15 or fewer, about 10 or fewer, about 8 or fewer, or about 6 or fewer pulses in the cycle. The pulse cycle can be regularly repeated, for example every about 50 microseconds (µs) to about 300 µs (such as about every 75 µs to about 200 µs, or every about 100 µs) during operation. In some embodiments, the cycle is reaped every 50 µs or longer, every 100 µs or longer, every 150 µs or longer, every 200 µs or longer, every 250 µs or longer, or every 300 µs or longer. In some embodiments, the cycle is repeated every 300 µs or sooner, every 250 µs or sooner, every 200 µs or sooner, every 150 µs or sooner, or every 100 µs or sooner. The cycle frequency can set, for example, based on the distance between the interrogator and the implantable device and/or the speed at which the transducer can toggle between the transmitting and receiving modes.

FIG. 5 illustrates cycled pulse-echo ultrasonic communication between the interrogator and the implantable device. FIG. 5A shows a series of pulse cycles with a frequency of every 100 microseconds. During the transmission of the pulses, the transducers in the array are configured to transmit the ultrasonic waves. After the pulses are transmitted, the transducers are configured to receive backscattered ultrasonic waves. FIG. 5B shows a zoom-in view of a cycle, which shows six pulses of ultrasonic waves, with a frequency of every 540 nanoseconds. Backscattered ultrasonic waves detected by the interrogator are shown in FIG. 5C, with a zoom-in view of a single pulse shown in FIG. 5D. As shown in FIG. 5D, the ultrasonic backscatter received from the implantable device can be analyzed, which may include filtering (for example, to remove the wave decay) the backscattered waves, rectifying the backscattered waves, and integrating the waves to determine the data encoded by the waves. In some embodiments, the backscatter waves are analyzed using a machine learning algorithm. FIG. 5E shows a zoomed in version of the filtered backscattered waves. The backscatter wave shown in FIG. 5E includes four distinct regions corresponding to reflections arising from mechanical boundaries: (1) reflection from the biocompatible material that encapsulates the implantable device; (2) reflection from the top surface of the miniaturized ultrasonic transducer; (3) reflection from the boundary between the printed circuit board and the miniaturized ultrasonic transducer; and (4) reflection from the back of the printed circuit board. The amplitude of the backscatter waves reflected from the surface of the miniaturized transducer changed as a function of changes in impedance of the current flowing through the miniaturized ultrasonic transducer, and can be referred to as the "responsive backscatter" since this region of the backscatter can encode information transmitted from the ultrasonic device to the interrogator. The other regions of the ultrasonic backscatter can be referred to as "non-responsive backscatter," and are useful in determining the position of the implantable device, movement of the implantable device, and/or temperature changes proximal to the implantable device, as explained below. In some embodiments, the device further comprises a non-responsive reflector. In some embodiments, the non-responsive reflector is a cube. In some embodiments, the non-responsive reflector comprises silicon. In some embodiments, the non-responsive reflector is a surface of rigid material. The non-responsive reflector is attached to the implantable device but electrically isolated, and can reflect ultrasonic waves that are not responsive to changes in current impedance.

The frequency of the ultrasonic waves transmitted by the transducer can be set depending on the drive frequency or resonant frequency of the miniaturized ultrasonic transducer on the implantable device. In some embodiments, the miniaturized ultrasonic transducers are broad-band devices. In some embodiments, the miniaturized ultrasonic transducers are narrow-band. For example, in some embodiments the frequency of the pulses is within about 20% or less, within about 15% or less, within about 10% or less, within about 5% or less of the resonant frequency of the miniaturized ultrasonic transducer. In some embodiments, the pulses are set to a frequency about the resonant frequency of the miniaturized ultrasonic transducer. In some embodiments, the frequency of the ultrasonic waves is between about 100 kHz and about 100 MHz (such as between about 100 kHz and about 200 kHz, between about 200 kHz and about 500 kHz, between about 500 kHz and about 1 MHz, between about 1 MHz and about 5 MHz, between about 5 MHz and about 10 MHz, between about 10 MHz and about 25 MHz, between about 25 MHz and about 50 MHz, or between about 50 MHz and about 100 MHz). In some embodiments, the frequency of the ultrasonic waves is about 100 kHz or higher, about 200 kHz or higher, about 500 kHz or higher, about 1 MHz or higher, about 5 MHz or higher, about 10 MHz or higher, about 25 MHz or higher, or about 50 MHz or higher. In some embodiments, the frequency of the ultrasonic waves is about 100 MHz or lower, about 50 MHz or lower, about 25 MHz or lower, about 10 MHz or lower, about 5 MHz or lower, about 1 MHz or lower, about 500 kHz or lower, or about 200 kHz or lower. Higher frequency allows for a smaller miniaturized ultrasonic transducer on the implantable device. However, higher frequency also limits the depth of communication between the ultrasonic transducer and the implantable device. In some embodiments, the implantable device and the ultrasonic transducer are separated by about 0.1 cm to about 15 cm (such as about 0.5 cm to about 10 cm, or about 1 cm to about 5 cm). In some embodiments, the implantable device and the ultrasonic transducer are separated by about 0.1 cm or more, about 0.2 cm or more, about 0.5 cm or more, about 1 cm or more, about 2.5 cm or more, about 5 cm or more, about 10 cm or more, or about 15 cm or more. In some embodiments, the implantable device and the ultrasonic transducer are separated by about 20 cm or less, about 15 cm or less, about 10 cm or less, about 5 cm or less, about 2.5 cm or less, about 1 cm or less, or about 0.5 cm or less.

In some embodiments, the backscattered ultrasound is digitized by the implantable device. For example, the implantable device can include an oscilloscope or analog-to-digital converter (ADC) and/or a memory, which can digitally encode information in current (or impedance) fluctuations. The digitized current fluctuations, which can encode information, are received by the ultrasonic transducer, which then transmits digitized acoustic waves. The digitized data can compress the analog data, for example by using singular value decomposition (SVD) and least squares-based compression. In some embodiments, the compression is performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

In some embodiments, the digitized data can include a unique identifier. The unique identifier can be useful, for example, in a system comprising a plurality of implantable devices and/or an implantable device comprising a plurality of electrode pairs. For example, the unique identifier can identify the implantable device of origin when from a plurality of implantable devices, for example when transmitting information from the implantable device (such as a verification signal). In some embodiments, an implantable device comprises a plurality of electrode pairs, which may simultaneously or alternatively emit an electrical pulse by a single implantable device. Different pairs of electrodes, for example, can be configured to emit an electrical pulse in different tissues (e.g., different nerves or different muscles) or in different regions of the same tissue. The digitized circuit can encode a unique identifier to identify and/or verify which electrode pairs emitted the electrical pulse.

In some embodiments, the digitized signal compresses the size of the analog signal. The decreased size of the digitized signal can allow for more efficient reporting of information encoded in the ultrasonic backscatter. By compressing the size of the transmitted information through digitization, potentially overlapping signals can be accurately transmitted.

In some embodiments, an interrogator communicates with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. In some embodiments, two or more (such as 3, 4, 5, 6, 7, 8, 9, 10 or more, 12 or more, about 15 or more, about 20 or more, about 25 or more, about 50 or more, or about 100 or more) implantable devices communicate with the interrogator. In some embodiments, about 200 or fewer implantable devices (such as about 150 or fewer, about 100 or fewer, about 50 or fewer, about 25 or fewer, about 20 or fewer, about 15 or fewer, about 12 or fewer, or about 10 or fewer implantable devices) are in communication with the interrogator. The interrogator can receive a combined backscatter from the plurality of the implantable devices, which can be deconvoluted, thereby extracting information from each implantable device. In some embodiments, interrogator focuses the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. In some embodiments, the interrogator transmits ultrasonic waves to a plurality of implantable devices, and then receives ultrasonic waves from the plurality of implantable devices.

In some embodiments, the interrogator is used to determine the location or velocity of the implantable device. Velocity can be determined, for example, by determining the position or movement of a device over a period of time. The location of the implantable device can be a relative location, such as the location relative on the transducers on the interrogator. Knowledge of the location or movement of the implantable device allows for knowledge of the precise location of the electrophysiological signal detected in the tissue. By determining the location of the implantable device and associating the location with the detected electrophysiological signal, it is possible to characterize or monitor the tissue at a more localized point. A plurality of transducers on the interrogator, which may be disposed on the same transducer array or two or more different transducer arrays, can collect backscatter ultrasonic waves from an implantable device. Based on the differences between the backscatter waveform arising from the same implantable device and the known location of each transducer, the position of the implantable device can be determined. This can be done, for example by triangulation, or by clustering and maximum likelihood. The differences in the backscatter may be based on responsive backscatter waves, non-responsive backscatter waves, or a combination thereof.

In some embodiments, the interrogator is used to track movement of the implantable device. Movement of the implantable device that can be tracked by the interrogator includes lateral and angular movement. Such movement may arise, for example, due to shifting of one or more organs such as the liver, stomach, small or large intestine, kidney, pancreas, gallbladder, bladder, ovaries, uterus, or spleen, bones, or cartilage (which may be result, for example, of respiration or movement of the subject), or variations in blood flow (such as due to a pulse). Movement of the implantable device can be tracked, for example, by monitoring changes in the non-responsive ultrasonic waves. In some embodiments, movement of the implantable device is determined my comparing the relative location of the implantable device at a first time point to the relative location of the implantable device at a second time point. For example, as described above, the location of an implantable device can be determined using a plurality of transducers on the interrogator (which may be on a single array or on two or more arrays). A first location of the implantable device can be determined at a first time point, and a second location of the implantable device can be determined at a second time point, and a movement vector can be determined based on the first location at the first time point and the second location at the second time point.

Implantable Device

An implantable device configured to emit an electrical pulse include includes a miniaturized ultrasonic transducer (such as a miniaturized piezoelectric transducer, a capacitive micro-machined ultrasonic transducer (CMUT), or a piezoelectric micro-machined ultrasonic transducer (PMUT)) configured to receive ultrasonic waves that power the implantable device, a power circuit comprising an energy storage circuit, and two or more electrodes configured to engage a tissue and emit an electrical pulse. In some embodiments, the ultrasonic waves encode a trigger signal. The implantable device is configured to emit the electrical pulse upon receipt of the trigger signal. In some embodiments, the implantable device includes an integrated circuit. The integrated circuit can include, for example, the power circuit and a digital circuit. The digital circuit or a mixed-signal integrated circuit can operate the power circuit and the electrodes to signal emission of the electric pulse. In some embodiments, for example when the implantable device is configured to emit ultrasonic backscatter encoding information, the integrated circuit can include a modulation circuit, which can be operated by the digital circuit.

The implantable device can engage the tissue to apply an electrical pulse to the tissue. In some embodiments, the electrodes are placed within, placed on, placed near, or in electrical communication with the tissue to be stimulated. In some embodiments, the electrodes are positioned in contact with the tissue. The tissue can be, for example, nervous tissue, muscle tissue, or an organ. For example, the nervous tissue can be central nervous system nervous tissue (such as the brain or the spinal cord), or peripheral nervous system nervous tissue (e.g., a nerve). The muscle tissue can be, for example, skeletal muscle, cardiac muscle, or smooth muscle. In some embodiments, the electrical pulse stimulates an action potential in the tissue. In some embodiments, the electrical pulse blocks an action potential in a tissue.

In some embodiments, the electrical pulse emitted by the implantable device is a direct current pulse or an alternating current pulse. In some embodiments, the electrical pulse comprises a plurality of pulses, which may be separated by a dwell time. In some embodiments, the electrical pulse is about 1 microsecond (µs) or longer (such as about 5 µs or longer, about 10 µs or longer, about 20 µs is or longer, about 50 µs or longer, about 100 µs or longer, about 250 µs or longer, about 500 µs or longer, about 1 millisecond (ms) or longer, about 5 ms or longer, about 10 ms or longer, about 25 ms or longer, about 50 ms or longer, about 100 ms or longer, about 200 ms or longer, or about 500 ms or longer). In some embodiments, the electrical pulse is about 1000 ms or shorter (such as about 500 ms or shorter, about 200 ms or shorter, about 100 ms or shorter, or about 50 ms or shorter, about 25 ms or shorter, about 10 ms or shorter, about 5 ms or shorter, about 1 ms or shorter, about 500 µs or shorter, about 250 µs or shorter, about 100 µs or shorter, about 50 µs is or shorter, about 20 µs or shorter, about 10 µs or shorter, or about 5 µs or shorter). In some embodiments, the dwell time is about 1 microsecond (µs) or longer (such as about 5 µs or longer, about 10 µs or longer, about 20 µs or longer, about 50 µs or longer, about 100 µs or longer, about 250 µs or longer, about 500 µs or longer, about 1 millisecond (ms) or longer, about 5 ms or longer, about 10 ms or longer, about 25 ms or longer, or about 50 ms or longer). In some embodiments, the dwell time is about 100 ms or shorter (such as about 50 ms or shorter, about 25 ms or shorter, about 10 ms or shorter, about 5 ms or shorter, about 1 ms or shorter, about 500 µs or shorter, about 250 µs or shorter, about 100 µs or shorter, about 50 µs or shorter, about 20 µs or shorter, about 10 µs or shorter, or about 5 µs or shorter).

In some embodiments, the electrical pulse is about 1 microamp (µA) or more (such as about 5 µA or more, about 10 µA or more, about 25 µA or more, about 50 µA or more, about 100 µA or more, about 250 µA or more, about 500 µA or more, about 1 milliamp (mA) or more, about 5 mA or more, about 10 mA or more, or about 25 mA or more). In some embodiments, the electrical pulse is about 50 mA or less (such as about 25 mA or less, about 10 mA or less, about 5 mA or less, about 1 mA or less, about 500 µA or less, about 250 µA or less, about 100 µA or less, about 50 µA or less, about 25 µA or less, about 10 µA or less, about 5 µA or less, or about 1 µA or less.

In some embodiments, the electrical pulse has a current frequency of about 0.1 Hz or more (such as about 0.5 Hz or more, about 1 Hz or more, about 5 Hz or more, about 10 Hz or more, about 25 Hz or more, about 50 Hz or more, about 100 Hz or more, about 200 Hz or more, about 300 Hz or more, about 400 Hz or more, about 500 Hz or more about 600 Hz or more, about 700 Hz or more, about 800 Hz or more, about 1 kHz or more, about 2 kHz or more, or about 5 kHz or more). In some embodiments, the electrical pulse has a current frequency of about 10 kHz or less (such as about 5 kHz or less, about 2 kHz or less, about 1 kHz or less, about 800 Hz or less, about 700 Hz or less, about 600 Hz or less, about 500 Hz or less, about 400 Hz or less, about 300 Hz or less, about 200 Hz or less, about 100 Hz or less, about 50 Hz or less, about 25 Hz or less, about 10 Hz or less, about 5 Hz or less, about 1 Hz or less, or about 0.5 Hz or less).

In some embodiments, the implantable device generates a voltage pulse in the tissue. In some embodiments, the voltage is about 50 mV or more (such as about 100 mV or more, about 250 mV or more, about 500 mV or more about 1 V or more, about 2.5 V or more, about 5 V or more, or about 10 V or more). In some embodiments, the voltage is about 20 V or less (such as about 15 V or less, about 10 V or less, about 5 V or less, about 2.5 V or less, about 1 V or less, about 500 mV or less, about 250 mV or less, or about 100 mV or less).

In some embodiments, the implantable device comprises a plurality of electrodes. In some embodiments, the electrodes are paired. Electrode pairs can be formed from two electrodes; thus, an implantable device with three electrodes can have three electrode pairs. The electrophysiological signal can be detected between the electrodes in the electrode pairs. In some embodiments, the implantable device comprises 1, 2, 3, 4, 5, 6, 7, 8, 9, 10 or more, or 15 or more electrode pairs. In some embodiments, the implantable device comprises 2, 3, 5, 6, 7, 8, 9, 10 or more electrodes. In some embodiments, the implantable device includes an even number of electrodes, and in some embodiments the implantable device includes an odd number of electrodes. In some embodiments, the implantable device includes a multiplexer, which can select the electrodes in the electrode pair to emit the electrical pulse.

Two or more electrodes interface with (or engage) the tissue (e.g., nervous tissue or muscular tissue). The electrodes need not be linearly disposed along the tissue. For example, the electrodes may engage a nerve along a transverse axis relative to the nerve, which can emit an electrical pulse in the transverse direction. Two or more electrodes can engage a nerve along the transverse axis at any angle, such as directly opposite (i.e., 180°), or less than 180° (such as about 170° or less, about 160° or less, about 150° or less, about 140° or less, about 130° or less, about 120° or less, about 110° or less, about 100° or less, about 90° or less, about 80° or less, about 70° or less, about 60° or less, about 50° or less, about 40° or less, or about 30° or less).

In some embodiments, the electrodes in an electrode pair are separated by about 5 mm or less (such as about 4 mm or less, about 3 mm or less, about 2 mm or less, about 1.5 mm or less, about 1 mm or less, or about 0.5 mm or less). In some embodiments, the electrodes in the electrode pair are separated by about 0.5 mm or more (such as about 1 mm or more, about 1.5 mm or more, about 2 mm or more, about 3 mm or more, or about 4 or more. In some embodiments, the electrodes are separated by about 0.5 mm to about 1 mm, about 1 mm to about 1.5 mm, about 1.5 mm to about 2 mm, about 2 mm to about 3 mm, about 3 mm to about 4 mm, or about 4 mm to about 5 mm.

In some embodiments, the implantable device includes a power circuit, which includes an energy storage circuit. The energy storage circuit can include one or more capacitors. Energy from the ultrasonic waves is converted into a current by the miniaturized ultrasonic transducer, and can be stored in the energy storage circuit. The energy can be used to operate the implantable device, such as providing power to the digital circuit or one or more amplifiers, or can be used to generate the electrical pulse used to stimulate the tissue. In some embodiments, the power circuit further includes, for example, a rectifier and/or a charge pump.

In some embodiments the integrated circuit includes one or more digital circuits or mixed-signal integrated circuits, which can include a memory and one or more circuit blocks or systems for operating the implantable device. These systems can include, for example, an onboard microcontroller or processor, a finite state machine implementation or digital circuits capable of executing one or more programs stored on the implant or provided via ultrasonic communication between interrogator and implantable device. In some embodiments, the digital circuit includes an analog-to-digital converter (ADC), which can convert analog signal encoded in the ultrasonic waves emitted from the interrogator so that the signal can be processed by the digital circuit. The digital circuit can also operate the power circuit, for example to generate the electrical pulse to stimulate the tissue. In some embodiments, the digital circuit receives the trigger signal encoded in the ultrasonic waves transmitted by the interrogator, and operates the power circuit to discharge the electrical pulse in response to the trigger signal.

In some embodiments, the implantable device emits ultrasonic backscatter that encodes information. The ultrasonic backscatter can be received by the interrogator, for example, and deciphered to determine the encoded information. The information can be encoded using a modulation circuit (or "backscatter circuit"). The modulation circuit can modulate the current flowing through the miniaturized ultrasonic transducer, which modulates the ultrasonic backscatter. In some embodiments, the modulation circuit is operated by a digital circuit, which can encode a digitized signal transmitted to the modulation circuit, which transmits the digitized signal to the ultrasonic transducer thereby encoding digitized information in the ultrasonic backscatter. The modulation circuit (or "backscatter circuit) includes a switch, such as an on/off switch or a field-effect transistor (FET). An exemplary FET that can be used with some embodiments of the implantable device is a metal-oxide-semiconductor field-effect transistor (MOSFET). The modulation circuit can alter the impedance of a current flowing through the miniaturized ultrasonic transducer, and variation in current flowing through the transducer encodes the electrophysiological signal. In some embodiments, information encoded in the ultrasonic backscatter includes a unique identifier for the implantable device. This can be useful, for example, to ensure the interrogator is in communication with the correct implantable device when a plurality of implantable devices is implanted in the subject. In some embodiments, the information encoded in the ultrasonic backscatter includes a verification signal that verifies an electrical pulse was emitted by the implantable device. In some embodiments, the information encoded in the ultrasonic backscatter includes an amount of energy stored or a voltage in the energy storage circuit (or one or more capacitors in the energy storage circuit). In some embodiments, the information encoded in the ultrasonic backscatter includes a detected impedance. Changes in the impedance measurement can identify scarring tissue or degradation of the electrodes over time.

FIG. 6 illustrates one embodiment of a miniaturized ultrasonic transducer (identified as the "piezo") connected to an ASIC. The ASIC includes a power circuit and an optional modulation circuit (or "backscatter circuit"). The power circuit includes an energy storage capacitor ("cap"). Additionally, the implantable device includes a stimulation circuit (e.g., a digital circuit), which can operate the power circuit and the electrodes, which are implanted in or positioned against the tissue to be stimulated.

Figure 7:
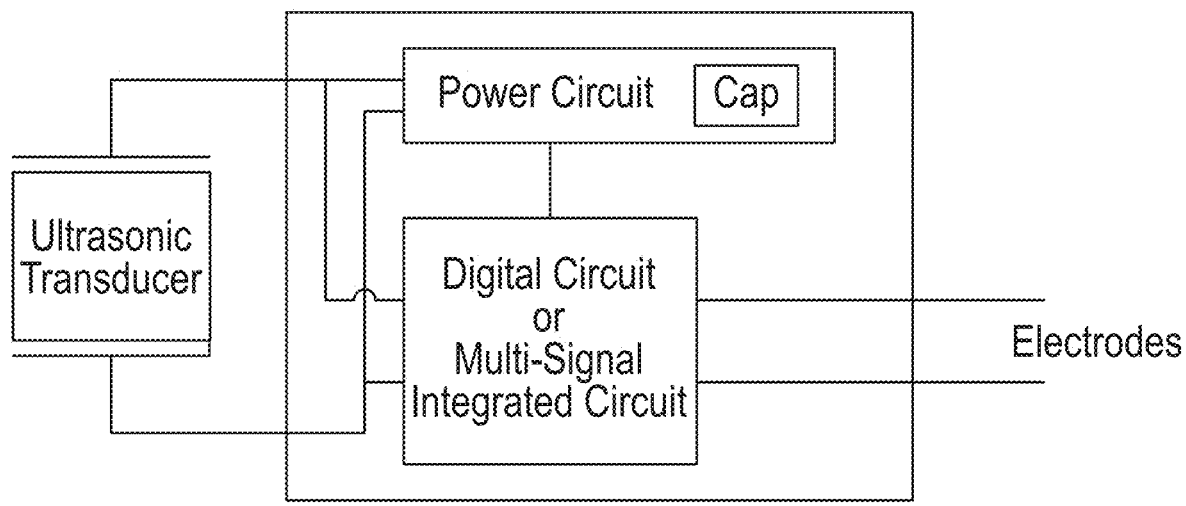
FIG. 7 illustrates an embodiment of an implantable device configured to emit an electrical pulse. The implantable device includes a miniaturized ultrasonic transducer, a power circuit including an energy storage circuit (which can include one or more capacitors ("cap"), a digital circuit, and a pair of electrodes.

FIG. 7 illustrates an embodiment of an implantable device configured to emit an electrical pulse. The implantable device includes a miniaturized ultrasonic transducer, a power circuit including an energy storage circuit (which can include one or more capacitors ("cap"), a digital circuit or multi-signal integrated circuit, and a pair of electrodes. The ultrasonic transducer is connected to the power circuit, which allows energy from the ultrasonic waves to be stored in the energy storage circuit. The power circuit is connected to the digital circuit or multi-signal integrated circuit so that the digital circuit or multi-signal integrated circuit can operate the power circuit. The digital circuit or multi-signal integrated circuit is also connected to the ultrasonic transducer. When a trigger signal is encoded in ultrasonic waves received by the ultrasonic transducer, the digital circuit or multi-signal integrated circuit can detect the trigger signal. The digital circuit or multi-signal integrated circuit can then operate the power circuit to release energy stored in the energy circuit, thereby emitting an electrical pulse using the electrodes.

The implantable devices are miniaturized, which allows for comfortable and long-term implantation while limiting tissue inflammation that is often associated with implantable devices. The body forms the core of the miniaturized implantable device (e.g., the ultrasonic transducer and the integrated circuit), and the electrodes branch from the body and engage the tissue to deliver an electrical pulse to stimulate the tissue. In some embodiments, the longest dimension of the implantable device or the body of the implantable device is about 5 mm or less, about 4 mm or less, about 3 mm or less, about 2 mm or less, about 1 mm or less, about 0.5 mm or less, or about 0.3 mm or less in length. In some embodiments, the longest dimension of the implantable device or body of the implantable device is about 0.2 mm or longer, about 0.5 mm or longer, about 1 mm or longer, about 2 mm or longer, or about 3 mm or longer in the longest dimension of the device. In some embodiments, the longest dimension of the implantable device or the body of the implantable device is about 0.2 mm to about 5 mm in length, about 0.3 mm to about 4 mm in length, about 0.5 mm to about 3 mm in length, about 1 mm to about 3 mm in length, or about 2 mm in length.

In some embodiments, one or more of the electrodes are on the body of the device, for example a pad on the body of the device. In some embodiments, one or more of the electrodes extend from the body of the implantable device at any desired length, and can be implanted at any depth within the tissue. In some embodiments, an electrode is about 0.1 mm in length or longer, such as about 0.2 mm or longer, about 0.5 mm or longer, about 1 mm in length or longer, about 5 mm in length or longer, or about 10 mm in length or longer. In some embodiments, the electrodes are about 15 mm or less in length, such as about 10 mm or less, about 5 mm or less, about 1 mm or less, or about 0.5 mm or less in length. In some embodiments, the first electrode is disposed on the body of the implantable device and the second electrode extends from the body of the implantable device.

In some embodiments, the implantable device has a volume of about 5 mm$^3$ or less (such as about 4 mm$^3$ or less, 3 mm$^3$ or less, 2 mm$^3$ or less, or 1 mm$^3$ or less). In certain embodiments, the implantable device has a volume of about 0.5 mm$^3$ to about 5 mm$^3$, about 1 mm$^3$ to about 5 mm$^3$, about 2 mm$^3$ to about 5 mm$^3$, about 3 mm$^3$ to about 5 mm$^3$, or about 4 mm$^3$ to about 5 mm$^3$. The small size of the implantable device allows for implantation of the device using a biopsy needle.

In some embodiments, the implantable device is implanted in a subject. The subject can be for example, a vertebrate animal, such as a mammal. In some embodiments, the subject is a human, dog, cat, horse, cow, pig, sheep, goat, chicken, monkey, rat, or mouse.

In some embodiments, the implantable device or a portion of the implantable device (such as the miniaturized ultrasonic transducer and the integrated circuit) is encapsulated by a biocompatible material (such as a biocompatible polymer), for example a copolymer of N-vinyl-2-pyrrolidinone (NVP) and n-butylmethacrylate (BMA), polydimethylsiloxane (PDMS), parylene, polyimide, silicon nitride, silicon dioxide, silicon carbide, alumina, niobium, or hydroxyapatite. The silicon carbide can be amorphous silicon carbide or crystalline silicon carbide. The biocompatible material is preferably impermeable to water to avoid damage or interference to electronic circuitry within the device. In some embodiments, the implantable device or portion of the implantable device is encapsulated by a ceramic (for example, alumina or titania) or a metal (for example, steel or titanium). In some embodiments, the electrodes or a portion of the electrodes are not encapsulated by the biocompatible material.

Figure 8A:
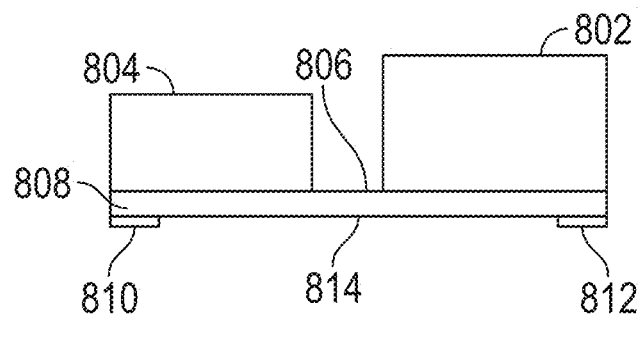
FIG. 8A illustrates a schematic of an exemplary implantable device including a miniaturized ultrasonic transducer and an ASIC on a printed circuit board (PCB).
Figure 8B:
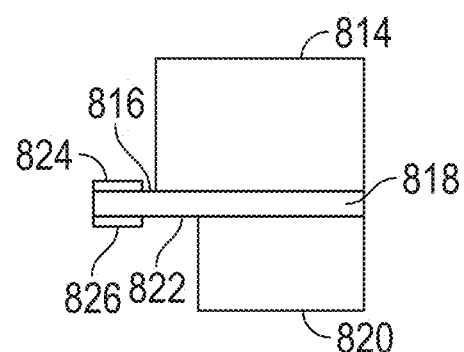
FIG. 8B illustrates a schematic of another exemplary implantable device including a miniaturized ultrasonic transducer and an ASIC on a printed circuit board (PCB).

In some embodiments, the miniaturized ultrasonic transducer and the ASIC are disposed on a printed circuit board (PCB). The electrodes can optionally be disposed on the PCB, or can otherwise be connected to the integrated circuit. FIGS. 8A and 8B illustrate exemplary configurations of the implantable device including a PCB. FIG. 8A shows the piezoelectric transducer 802 and an ASIC 804 disposed on a first side 806 of the PCB 808. A first electrode 810 and a second electrode 812 are disposed on a second side 814 of the PCB 808. FIG. 8B sows the piezoelectric transducer 814 on a first side 816 of the PCB 818, and the ASIC 820 on the second side 822 of the PCB 818. A first electrode 824 initiates on the first side 816 of the PCB, and a second electrode 826 is initiates on the second side 822 of the PCB 818. The first electrode 824 and the second electrode 826 can extend from the PCB 818 to be configured to be in electrical connection with each other through the tissue.

The miniaturized ultrasonic transducer of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di)fluoride (PVDF), and lead magnesium niobate-lead titanate (PMN-PT).

In some embodiments, the miniaturized bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. In some embodiments, the miniaturized bulk piezoelectric transducer is long and narrow, with an aspect ratio of about 3:1:1 or greater, and where the longest dimension is aligned to the direction of propagation of the carrier ultrasound wave. In some embodiments, one dimension of the bulk piezoelectric transducer is equal to one half of the wavelength (λ) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 µm to about 1000 µm (such as about 40 µm to about 400 µm, about 100 µm to about 250 µm, about 250 µm to about 500 µm, or about 500 µm to about 1000 µm). In some embodiments, the height of the piezoelectric transducer is about 5 mm or less (such as about 4 mm or less, about 3 mm or less, about 2 mm or less, about 1 mm or less, about 500 µm or less, about 400 µm or less, 250 µm or less, about 100 µm or less, or about 40 µm or less). In some embodiments, the height of the piezoelectric transducer is about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in length.

In some embodiments, the ultrasonic transducer has a length of about 5 mm or less such as about 4 mm or less, about 3 mm or less, about 2 mm or less, about 1 mm or less, about 500 µm or less, about 400 µm or less, 250 µm or less, about 100 µm or less, or about 40 µm or less) in the longest dimension. In some embodiments, the ultrasonic transducer has a length of about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in the longest dimension.

The miniaturized ultrasonic transducer is connected two electrodes; the first electrode is attached to a first face of the transducer and the second electrode is attached to a second face of the transducer, wherein the first face and the second face are opposite sides of the transducer along one dimension. In some embodiments, the electrodes comprise silver, gold, platinum, platinum-black, poly(3,4-ethylenedioxythiophene (PEDOT), a conductive polymer (such as conductive PDMS or polyimide), or nickel. In some embodiments, the transducer is operated in shear-mode where the axis between the metallized faces (i.e., electrodes) of the transducer are orthogonal to the motion of the transducer.

In some embodiments, the implantable devices are configured to engage with nervous tissue. In some embodiments, engagement of the nervous tissue does not completely surround the nervous tissue. In some embodiments, the nervous tissue is part of the central nervous system, such as the brain (e.g., cerebral cortex, basal ganglia, midbrain, medulla, pons, hypothalamus, thalamus, cerebellum, pallium, or hippocampus) or spinal cord. In some embodiments, engagement with brain tissue includes electrodes that are implanted in the tissue, whereas the body of the implantable device is located outside of the tissue. In some embodiments, the nervous tissue is part of the peripheral nervous system, such as a peripheral nerve. In some embodiments, the implantable device is engaged with a muscle, such as skeletal muscle, cardiac muscle, or smooth muscle. In some embodiments, electrodes from the implantable device are engaged with the muscle, such as skeletal muscle, smooth muscle, or cardiac muscle.

Manufacture of an Implantable Device

The implantable devices can be manufactured by attaching a miniaturized ultrasonic transducer (such as a bulk piezoelectric transducer, a CMUT, or a PMUT) to a first electrode on a first face of the piezoelectric transducer, and a second electrode to a second face of the transducer, wherein the first face and the second face are on opposite sides of the transducer. The first electrode and the second electrode can be attached to an integrated circuit, which may be disposed on a printed circuit board (PCB). The integrated circuit includes a power circuit including an energy storage circuit. In some embodiments, the integrated circuit includes a digital circuit (or a multi-signal integrated circuit) and/or a modulation circuit. Two or more electrodes are also attached to the integrated circuit, and are configured to be in electrical connection with each other through the tissue. Attachment of the components to the PCB can include, for example, wirebonding, soldering, flip-chip bonding, or gold bump bonding Certain piezoelectric materials can be commercially obtained, such as metalized PZT sheets of varying thickness (for example, PSI-5A4E, Piezo Systems, Woburn, Mass., or PZT 841, APC Internationals, Mackeyville, Pa.). In some embodiments, a piezoelectric material sheet is diced into a desired size, and the diced piezoelectric material is attached to the electrodes. In some embodiments, the electrodes are attached to the piezoelectric material sheet, and the piezoelectric material sheet is diced to the desired size with the electrodes attached to the piezoelectric material. The piezoelectric material can be diced using a dicing saw with a ceramic blade to cut sheets of the piezoelectric material into individualized piezoelectric transducer. In some embodiments, a laser cutter is used to dice or singulate the piezoelectric material. In some embodiments, patterned etching is used to dice or singulate the piezoelectric material.

Electrodes can be attached to the top and bottom of the faces of the piezoelectric transducers, with the distance between the electrodes being defined as the height of the piezoelectric transducer. Exemplary electrodes can comprise one or more of silver, gold, platinum, platinum-black, poly (3,4-ethylenedioxythiophene (PEDOT), a conductive polymer (such as conductive PDMS or polyimide), or nickel. In some embodiments, the electrode is attached to the piezoelectric transducer by electroplating or vacuum depositing the electrode material onto the face of the piezoelectric transducer. In some embodiments, the electrodes are soldered onto the piezoelectric transducer using an appropriate solder and flux. In some embodiments, the electrodes are attached to the piezoelectric transducer using an epoxy (such as a silver epoxy) or low-temperature soldering (such as by use of a solder paste).

In an exemplary embodiment, solder paste is applied to a pad on a printed circuit board (PCB), either before or after the integrated circuit is attached to the PCB. The size of the pad on the circuit board can depend on the desired size of the piezoelectric transducer. Solely by way of example, if the desired size of piezoelectric transducer is about 100 µm×100 µm×100 µm, the pad can be about 100 µm×100 µm. The pad functions as the first electrode for the implantable device. A piezoelectric material (which may be larger than the pad) is placed on the pad, and is held to the pad by the applied solder paste, resulting in a piezoelectric-PCB assembly. The piezoelectric-PCB assembly is heated to cure the solder paste, thereby bonding the piezoelectric transducer to the PCB. If the piezoelectric material is larger than the pad, the piezoelectric material is cut to the desired size, for example using a wafer dicing saw or a laser cutter. Non-bonded portions of the piezoelectric material (for example, the portions of the piezoelectric material that did not overlay the pad) are removed. A second electrode is attached to the piezoelectric transducer and the PCB, for example by forming a wirebond between the top of the piezoelectric transducer and the PCB, which completes the circuit. The wirebond is made using a wire made from any conductive material, such as aluminum, copper, silver, or gold.

The integrated circuit and the miniaturized transducer can be attached on the same side of the PCB or on opposite sides of the PCB. In some embodiments, the PCB is a flexible PCB, the integrated circuit and the miniaturized transducer are attached to the same side of the PCB, and the PCB is folded, resulting in an implantable device in which the integrated circuit and the miniaturized transducer are on opposite sides of the PCB.

Optionally, the device or a portion of the device is encapsulated in or a portion of the device is encapsulated in a biocompatible material (such as a biocompatible polymer), for example a copolymer of N-vinyl-2-pyrrolidinone (NVP) and n-butylmethacrylate (BMA), polydimethylsiloxane (PDMS, e.g., Sylgard 184, Dow Corning, Midland, Mich.), parylene, polyimide, silicon nitride, silicon dioxide, alumina, niobium, hydroxyapatite, or silicon carbide. The silicon carbide can be amorphous silicon carbide or crystalline silicon carbide. In some embodiments, the biocompatible material (such as amorphous silicon carbide) is applied to the device by plasma enhanced chemical vapor deposition (PECVD) or sputtering. PECVD may use precursors such as $SiH_4$ and $CH_4$ to generate the silicon carbide. In some embodiments, the implantable device or portion of the implantable device is encased in a ceramic (for example, alumina or titania) or a metal (for example, steel or titanium) suitable for medical implantation.

Figure 9:
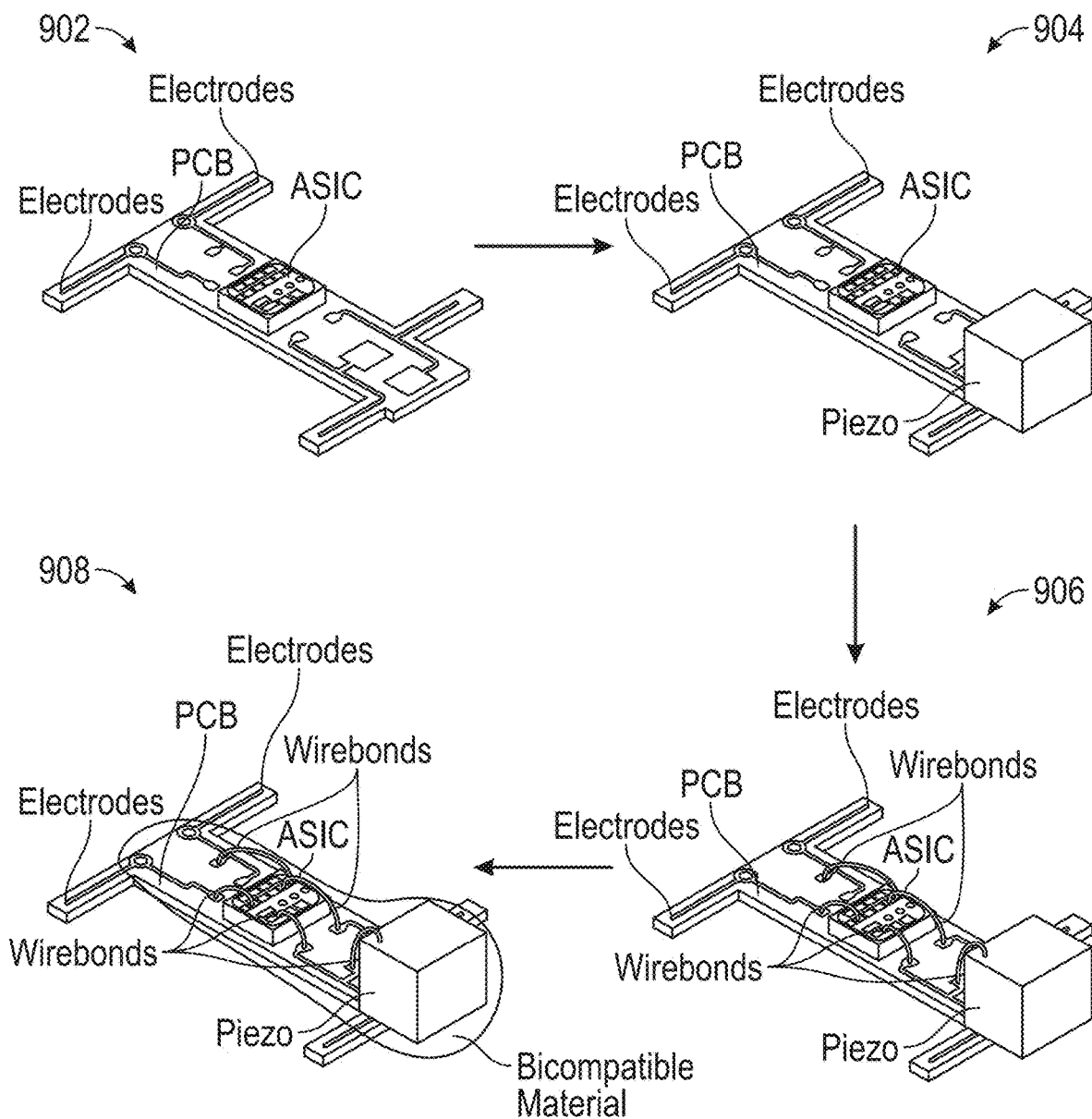
FIG. 9 illustrates a method of manufacturing an implantable device described herein.

FIG. 9 illustrates an exemplary method of producing the implantable device described herein. At step 902, an application specific integrated circuit (ASIC) is attached to a PCB. The PCB can include two or more electrodes for emitting an electrical pulse to stimulate the tissue. A solder (such as a silver epoxy) can be applied to the PCB (for example, at a first pad disposed on the PCB), and the ASIC can be placed on the solder. The solder can be cured, for example by heating the PCB with the ASIC. In some embodiments, the PCB with the ASIC is heated to about 50° C. to about 200° C., such as about 80° C. to about 170° C., or about 150° C. In some embodiments, the PCB with the ASIC is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. Optionally, the ASIC is coated with additional solder. At step 904, a piezoelectric transducer (the "piezo" in FIG. 9) is attached to the PCB. A solder (such as a silver epoxy) can be applied to the PCB (for example, at a second pad disposed on the PCB), and a piezoelectric material can be placed on the solder. The piezoelectric material can be a fully formed (i.e., "diced") piezoelectric transducer, or can be a piezoelectric material sheet that is cut to form the piezoelectric transducer once attached to the PCB. The solder can be cured, for example by heating the PCB with the piezoelectric material. In some embodiments, the PCB with the piezoelectric material is heated to about 50° C. to about 200° C., such as about 80° C. to about 170° C., or about 150° C. In some embodiments, the PCB with the piezoelectric material is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. The piezoelectric material can be cut using a saw or laser cutter to the desired dimensions. In some embodiments, the piezoelectric material is a solgel (such as a PZT solgel) and the transducer material can be shaped with deep reactive ion etching (DRIE). Although FIG. 9 illustrates attachment of the ASIC to the PCB at step 902 prior to attachment of the piezoelectric material to the PCB at step 904, a person of skill in the art will appreciate that the ASIC and the piezoelectric material can be attached in any order. At step 906, the ASIC and the piezoelectric transducer are wirebonded to the PCB. Although the method illustrated in FIG. 9 shows the ASIC and the piezoelectric transducer to the PCB after the ASIC and the piezoelectric transducer are attached to the PCB, a person of skill in the art will appreciate that the ASIC can be wirebonded to the PCB after the ASIC is attached to the PCB, and can be wirebonded either before or after attachment of the piezoelectric transducer. Similarly, the piezoelectric transducer may be wirebonded to the PCB either before or after attachment or wirebonding of the ASIC to the PCB. At step 908, at least a portion of the device is coated with a biocompatible material. Preferably, at least the piezoelectric transducer and the ASIC are coated with the biocompatible material. In some embodiments, the sensor is not or at least a portion of the sensor is not coated with the biocompatible material. For example, in some embodiments, the implantable device comprises a pair of electrodes which are not coated with the biocompatible material, which allows the electrodes to stimulate the tissue with an electrical pulse. In some embodiments, the biocompatible material is cured, for example by exposure to UV light or by heating.

Figure 10:
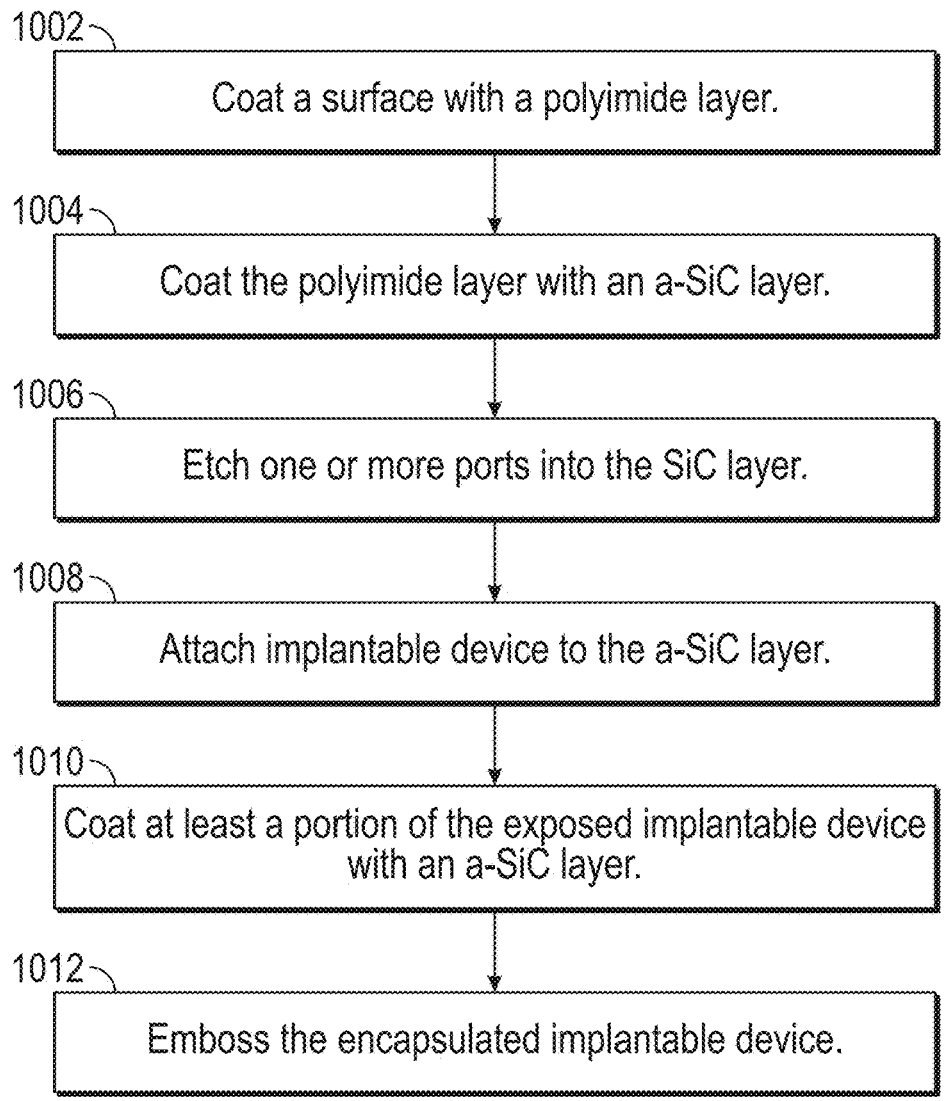
FIG. 10 is a flowchart for a method of encapsulating an implantable device with amorphous silicon carbide.

In some embodiments, the implantable device or a portion of the implantable device is encapsulated in an amorphous silicon carbide (a-SiC) film. FIG. 10 illustrates a method of manufacturing an implantable device encapsulated in an a-SiC film. At step 1002, a polyimide layer is applied to a smooth surface. At step 1004, an a-SiC layer is applied to the polyimide layer. This can be done, for example, using plasma enhanced chemical vapor deposition (PECVD), using $SiH_4$ and $CH_4$ as precursors. At step 1006, one or more ports are etched into the a-SiC layer. In some embodiments, ports are also etched into the polyimide layer. The ports provide access for portions of the implantable device that are not encapsulated by the a-SiC, such as portions of a sensor or an electrode that will contact the tissue after implant. In some embodiments, etching comprises reactive-ion etching. At step 1008, the implantable device is attached to the a-SiC layer. The implantable device may be pre-assembled before being attached to the a-SiC layer, or may be built on the a-SiC. In some embodiments, a printed circuit board (PCB), miniaturized ultrasonic transducer, and sensor are attached to the a-SiC layer. The miniaturized ultrasonic transducer and the sensor need not come in direct contact with the a-SiC layer, as they may be attached to the PCB. Attachment of miniaturized ultrasonic transducer or sensor to the PCB may occur before or after attachment of the PCB to the a-SiC layer. In some embodiments, attachment of miniaturized ultrasonic transducer or sensor to the PCB comprises wirebonding the miniaturized ultrasonic transducer or sensor to the PCB. In some embodiments, the sensor includes a portion that interfaces with the ports etched into the a-SiC layer. In some embodiments, an ASIC is attached to the PCB, which may occur before or after attachment of the PCB to the a-SiC layer. At step 1010, an exposed portion of the implantable device is coated with an a-SiC layer. In some embodiments, the exposed portion of the implantable device is coated with an a-SiC layer using PECVD. At step 1012, the encapsulated implantable device is embossed, thereby releasing the implantable device from the SiC layer.

Closed-Loop Recording and Stimulation Systems

There remains a need for new electrode-based recording technologies that can detect abnormalities in physiological signals and be used to update stimulation parameters in real time. Features of such technologies preferably include high-density, stable recordings of a large number of channels in single nerves, wireless and implantable modules to enable characterization of functionally specific neural and electromyographic signals, and scalable device platforms that can interface with small nerves of 100 mm diameter or less, as well as specific muscle fibers. Current approaches to recording peripheral nerve activity fall short of this goal; for example, known uses of cuff electrodes are limited to recording compound activity from the entire nerve. Single-lead intrafascicular electrodes can record from multiple sites within a single fascicle but do not enable high-density recording from discrete sites in multiple fascicles. Similarly, surface EMG arrays allow for very-high-density recording but do not capture fine details of deep or small muscles. Recently, wireless devices to enable untethered recording in rodents and nonhuman primates, as well as mm-scale integrated circuits for neurosensing applications have been developed. See, e.g., Biederman et al., *A 4.78 $mm^2$ fully-integrated neuromodulation SoC combining 64 acquisition channels with digital compression and simultaneous dual stimulation*, IEEE J. Solid State Circuits, vol. 5, pp. 1038-1047 (2015); Denison et al., *A 2 $\mu W$ 100 $nV/rtHz$ chpper-stabilized instrumentation amplifier for chronic measurement of neural field potentials*, IEEE J. Solid State Circuits, vol. 42, pp. 2934-2945 (2007); and Muller et al., *A minimially invasive 64-channel wireless uECOoG implant*, IEE J. Soid State Circuits, vol. 50, pp. 344-359 (2015). However, most wireless systems use electromagnetic (EM) energy coupling and communication, which becomes extremely inefficient in systems smaller than ~5 mm due to the inefficiency of coupling radio waves at these scales within tissue. Further miniaturization of wireless electronics platforms that can effectively interface with small-diameter nerves will require new approaches.

Figure 11:
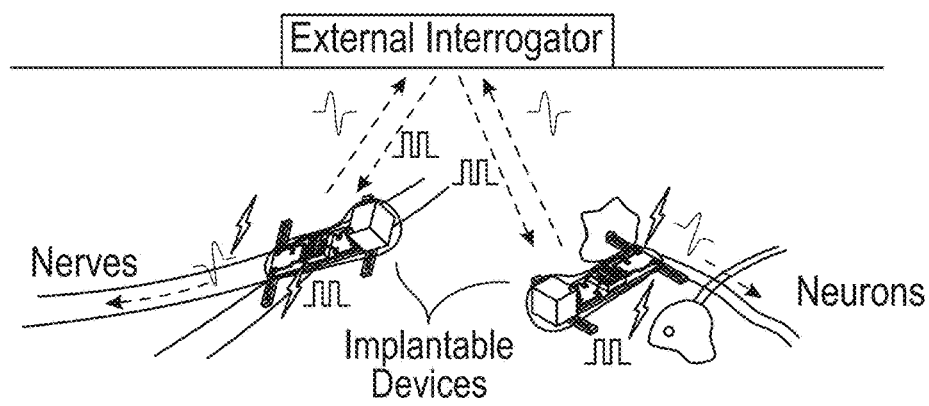
FIG. 11 shows a closed-loop system for neural recording and stimulation. One or more implantable devices configured to detect an electrophysiological pulse transmit ultrasonic backscatter to an external device (which includes an interrogator). The ultrasonic backscatter encodes the electrophysiological pulse. The external device then transmits ultrasonic waves encoding a trigger signal to one or more implantable devices configured to emit an electrical pulse. Upon receipt of the trigger signal, the implantable device emits an electrical pulse that stimulates the tissue.

In some embodiments, a wirelessly powered, scalable backscatter ultrasonic implantable system, which is used to record, stimulate, and/or block signals in the central and/or peripheral nervous system. As shown in FIG. 11, the implant is batteryless and embedded near a single or groups of neurons or implanted into either a nerve or muscle. A single or a group of external units (i.e., interrogators) placed outside powers and communicates with a single or a group of implants. In one embodiment, the implant measures and wirelessly reports recorded electrophysiological signatures back to the source via backscatter modulation. Alternatively, the implant harvests acoustic waves and converts it to electrical energy to power the application-specific integrated circuits (ASIC). The ASIC is used to generate a series of pulses to stimulate target nerves either electrically or acoustically. Existing clinical solutions for neural recording and stimulation are limited to recording and stimulating from the entire nerve or a large population of neurons and do not enable high-density recording from multiple discrete sites. Further known clinical solutions are large and cumbersome for long term use.

In some embodiments, the closed-loop system comprises an interrogator and an implantable device configured to stimulate a tissue in response to a detected electrophysiological signal. In some embodiments, the implantable device is configured to detect the electrophysiological signal. In some embodiments, a second implantable device is configured to detect the electrophysiological signal. The implantable devices can be deployed in a large, closed loop network. For example, in some embodiments, the closed-loop system includes a plurality of implantable devices configured to detect an electrophysiological signal and a plurality of implantable devices configured to emit an electrical pulse to stimulate a tissue.

Implantable Devices for Detecting an Electrophysiological Signal

The implantable device configured for detecting an electrophysiological signal includes a miniaturized ultrasonic transducer (such as a miniaturized piezoelectric transducer, a capacitive micro-machined ultrasonic transducer (CMUT), or a piezoelectric micro-machined ultrasonic transducer (PMUT)) configured to emit ultrasonic backscatter encoding a detected electrophysiological signal, a backscatter circuit (i.e., a modulation circuit) configured to modulate a current flowing through the miniaturized ultrasonic transducer based on the detected electrophysiological signal, and a first electrode and a second electrode configured to detect the electrophysiological signal in a tissue. In some embodiments, the implantable device includes an integrated circuit, which can include the modulation circuit, a digital circuit (or multi-signal integrated circuit), and/or a power circuit. Ultrasonic backscatter emitted from the miniaturized ultrasonic transducer can encode information related to the detected electrophysiological signal, and is received by an interrogator. The interrogator can be the same interrogator that is used to operate the implantable devices configured to emit the electrical pulse that stimulates tissue, or a different interrogator.

The modulation circuit (or "backscatter circuit) includes a switch, such as an on/off switch or a field-effect transistor (FET). An exemplary FET that can be used with some embodiments of the implantable device is a metal-oxide-semiconductor field-effect transistor (MOSFET). The modulation circuit can alter the impedance of a current flowing through the miniaturized ultrasonic transducer, and the variation in current flowing through the transducer encodes the electrophysiological signal.

Figure 12:
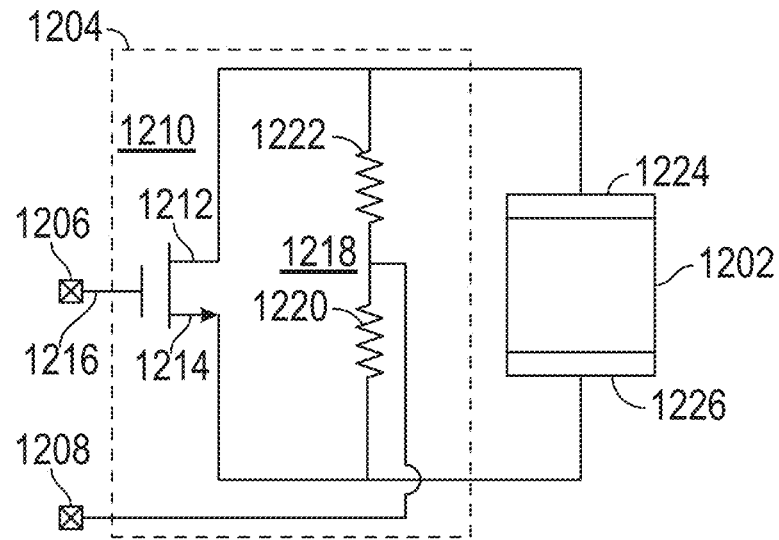
FIG. 12 illustrates an implantable device configured to detect an electrophysiological pulse having a miniaturized ultrasonic transducer, a modulation circuit configured to modulate a current flowing through the miniaturized ultrasonic transducer based on an electrophysiological signal detected by an electrode pair.

FIG. 12 illustrates an exemplary implantable device for recording electrophysiological signals. The implantable device includes a miniaturized ultrasonic transducer 1202, a modulation circuit 1204, a first electrode 1206, and a second electrode 1208. The first electrode 1206 and the second electrode 1208 are configured to engage a tissue (e.g., nervous or muscular tissue) to detect an electrophysiological signal. The modulation circuit includes a transistor 1210, which includes a drain 1212, source 1214, and a gate 1216. The gate 1216 is connected to the first electrode 1206. A resistor bridge 1218 comprising a first resistor 1220 and a second resistor 1222 bridge the drain 1212 and the source 1214. The second electrode 1208 is connected to the resistor bridge 1218 between the first resistor 1220 and the second resistor 1222. The ultrasonic transducer 1202 includes a first transducer electrode 1224 and a second transducer electrode 1226. The ultrasonic transducer 1202 can receive ultrasonic carrier waves from an interrogator, which generates a current through the circuit. Impedance of the current flowing through the modulation circuit is a function of the gate to source voltage, which is shifted by an electrophysiological pulse. The modulated current causes an ultrasonic backscatter to be emitted from the transducer 1202, which encodes the electrophysiological pulse.

In some embodiments the integrated circuit includes one or more digital circuits or multi-signal integrated circuits, which can include a memory and one or more circuit blocks or systems for operating the implantable device. These systems can include, for example an onboard microcontroller or processor, a finite state machine implementation or digital circuits capable of executing one or more programs stored on the implant or provided via ultrasonic communication between interrogator and implant. In some embodiments, the digital circuit includes an analog-to-digital converter (ADC), which can convert analog signal from the electrodes configured to detect the electrophysiological pulse into a digital signal. In some embodiments, the digital circuit includes a digital-to-analog converter (DAC), which converts a digital signal into an analog signal prior to directing the signal to a modulator. In some embodiments, the digital circuit or multi-signal integrated circuit operates the modulation circuit (which can also be referred to as a "backscatter circuit"). In some embodiments, the digital circuit or multi-signal integrated circuit transmits a signal to the modulation circuit encoding the detected phase-sensitive current and voltage. In some embodiments, the digital circuit or multi-signal integrated circuit can operate the modulation circuit (which can also be referred to as the "backscatter circuit"), which connects to the miniaturized ultrasonic transducer. The digital circuit or multi-signal integrated circuit can also operate one or more amplifiers, which amplifies the current directed to the switch.

In some embodiments, the digital circuit encodes a unique identifier a digitized signal comprising the electrophysiological signal. The unique identifier can identify the implantable device of origin of the ultrasonic backscatter (for example, in a system with a plurality of implantable devices), or may identify which electrodes on the implantable device detected the electrophysiological signal.

In some embodiments, the digitized circuit compresses the size of the analog signal. The decreased size of the digitized signal can allow for more efficient reporting of detected electrophysiological signals encoded in the ultrasonic backscatter. This can be useful, for example, when an implantable device includes a plurality of electrode pairs that simultaneously or approximately simultaneously detect an electrophysiological signal. By compressing the size of the electrophysiological signal through digitization, potentially overlapping signals can be accurately transmitted.

In some embodiments the integrated circuit filters false electrophysiological signals. In some embodiments, the filtering is performed by the digital circuit. An unfiltered voltage fluctuation can cause changes in the modulated current, which is encoded in the ultrasonic backscatter, which can be recorded as a false positive. To limit the false positives, current modulation can be filtered, for example by requiring the electrophysiological signal to be above a predetermined threshold to cause modulation of the current flowing through the ultrasonic transducer. In some embodiments, a spike detector is used to filter false-positive electrophysiological signals.

In some embodiments, the implantable device comprises one or more amplifiers. The amplifiers can, for example, amplify an electrophysiological signal. This may occur, for example, prior to the signal being transmitted to the digital circuit.

In some embodiments, the integrated circuit includes a power circuit, which is configured to power components of the implanted device. The power circuit can include, for example, a rectifier, a charge pump, and/or an energy storage capacitor. In some embodiments, the energy storage capacitor is included as a separate component. Ultrasonic waves that induce a voltage differential in the miniaturized ultrasonic transducer provide power for the implantable device, which can be managed by the power circuit.

In some embodiments, the implantable device comprises a plurality of electrode pairs. Electrode pairs can be formed from two electrodes; thus, an implantable device with three electrodes can have three electrode pairs. The electrophysiological signal can be detected between the electrodes in the electrode pairs. In some embodiments, the implantable device comprises 1, 2, 3, 4, 5, 6, 7, 8, 9, 10 or more, or 15 or more electrode pairs. In some embodiments, the implantable device comprises 2, 3, 5, 6, 7, 8, 9, 10 or more electrodes. In some embodiments, tin implantable device includes a multiplexer, which can select the electrodes in the electrode pair to detect an electrophysiological signal.

In some embodiments, the electrodes in an electrode pair are separated by about 5 mm or less (such as about 4 mm or less, about 3 mm or less, about 2 mm or less, about 1.5 mm or less, about 1 mm or less, or about 0.5 mm or less). In some embodiments, the electrodes in the electrode pair are separated by about 0.5 mm or more (such as about 1 mm or more, about 1.5 mm or more, about 2 mm or more, about 3 mm or more, or about 4 or more. In some embodiments, the electrodes are separated by about 0.5 mm to about 1 mm, about 1 mm to about 1.5 mm, about 1.5 mm to about 2 mm, about 2 mm to about 3 mm, about 3 mm to about 4 mm, or about 4 mm to about 5 mm.

Figure 13A:
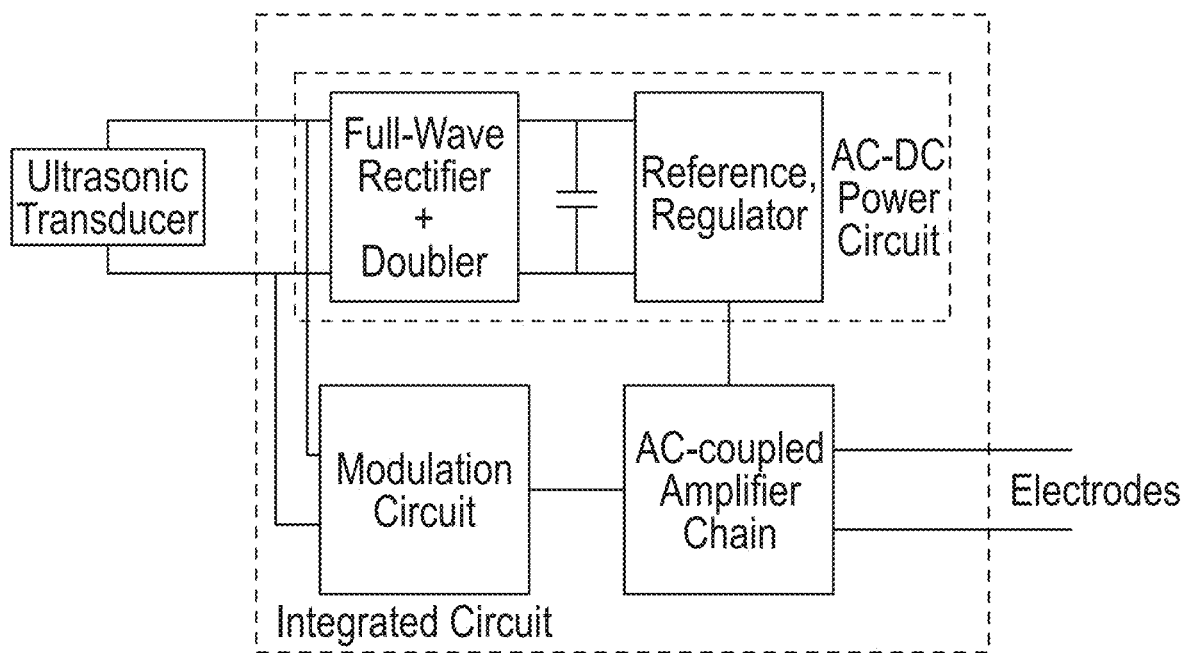
FIG. 13A illustrates an implantable device configured to detect an electrophysiological signal with a miniaturized ultrasonic transducer, and integrated circuit, and a pair of electrodes. The integrated circuit includes a modulation circuit, an AC-coupled amplifier chain, and a power circuit, which includes a full-wave rectifier and doubler, a reference, and a regulator.
Figure 13B:
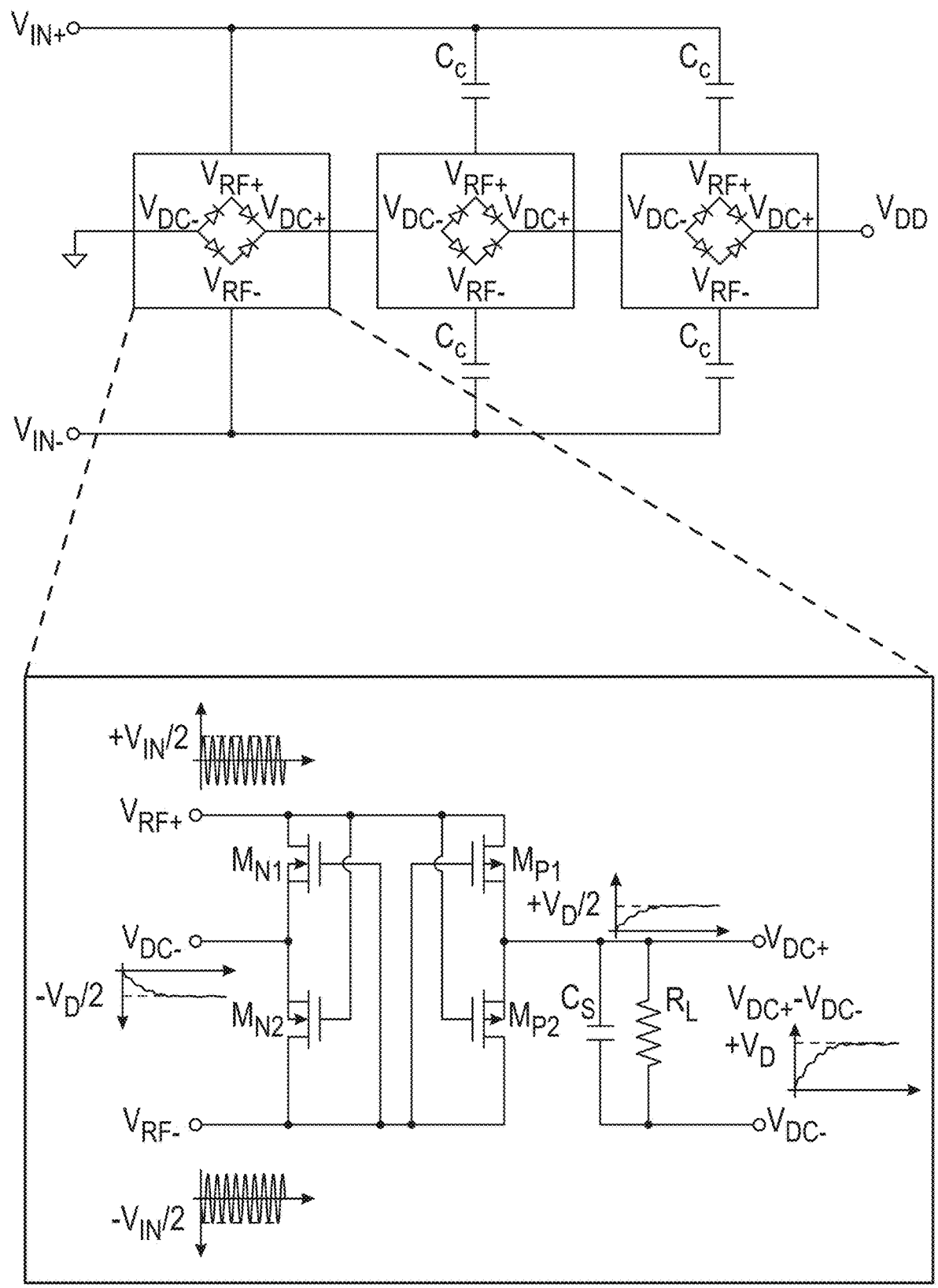
FIG. 13B illustrates an exemplary rectifier that can be used in the integrated circuit shown in FIG. 13A.
Figure 13C:
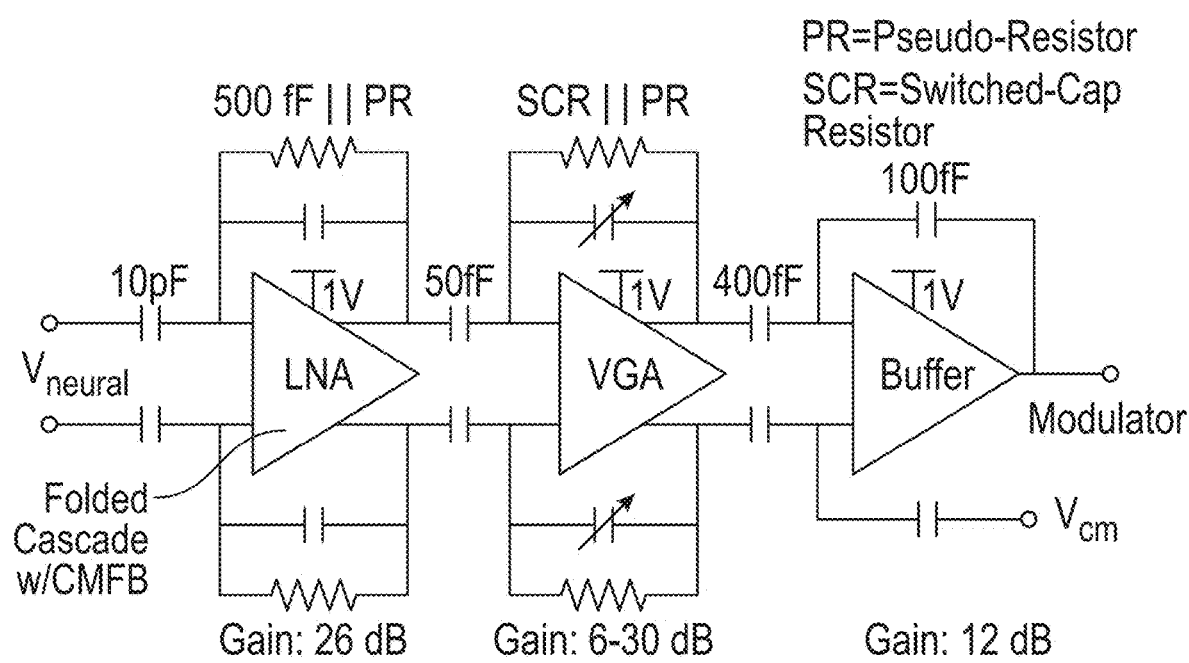
FIG. 13C illustrates an exemplary amplifier chain that can be used in the integrated circuit shown in FIG. 13A.

FIG. 13A illustrates an implantable device with a miniaturized ultrasonic transducer, an integrated circuit, and a first electrode and second electrode. The integrated circuit includes a modulation circuit, which is configured to receive a signal based on a detected electrophysiological signal, and modulate a current flowing through the ultrasonic transducer based on the received signal. The integrated circuit further includes an AC-DC power circuit, which includes a full-wave rectifier and doubler, as well as components for referencing or regulating the supplied power. FIG. 13B illustrates an exemplary rectifier that can be used with the implantable device. FIG. 13C illustrates exemplary architecture for an AC-coupled amplifier chain. The electrophysiological signal ("$V_{neural}$") is detected using the electrodes, and is amplified by the amplifier chain before the signal is transmitted to the modulation circuit.

The implantable devices are miniaturized, which allows for comfortable and long-term implantation while limiting tissue inflammation that is often associated with implantable devices. The body forms the core of the miniaturized implantable device (e.g., the ultrasonic transducer and the integrated circuit), and the electrodes branch from the body and engage the tissue. In some embodiments, the longest dimension of the implantable device or the body of the implantable device is about 5 mm or less, about 4 mm or less, about 3 mm or less, about 2 mm or less, about 1 mm or less, about 0.5 mm or less, or about 0.3 mm or less in length. In some embodiments, the longest dimension of the implantable device or body of the implantable device is about 0.2 mm or longer, about 0.5 mm or longer, about 1 mm or longer, about 2 mm or longer, or about 3 mm or longer in the longest dimension of the device. In some embodiments, the longest dimension of the implantable device or the body of the implantable device is about 0.2 mm to about 5 mm in length, about 0.3 mm to about 4 mm in length, about 0.5 mm to about 3 mm in length, about 1 mm to about 3 mm in length, or about 2 mm in length. The electrodes can extend from the device at any desired length, and can be implanted at any depth within the tissue. In some embodiments, an electrode is about 0.1 mm in length or longer, such as about 0.2 mm or longer, about 0.5 mm or longer, about 1 mm in length or longer, about 5 mm in length or longer, or about 10 mm in length or longer. In some embodiments, the electrodes are about 15 mm or less in length, such as about 10 mm or less, about 5 mm or less, about 1 mm or less, or about 0.5 mm or less in length.

In some embodiments, the implantable device has a volume of about 5 mm³ or less (such as about 4 mm³ or less, 3 mm³ or less, 2 mm³ or less, or 1 mm³ or less). In certain embodiments, the implantable device has a volume of about 0.5 mm³ to about 5 mm³, about 1 mm³ to about 5 mm³, about 2 mm³ to about 5 mm³, about 3 mm³ to about 5 mm³, or about 4 mm³ to about 5 mm³.

In some embodiments, the implantable device is implanted in a subject. The subject can be for example, a vertebrate animal, such as a mammal. In some embodiments, the subject is a human, dog, cat, horse, cow, pig, sheep, goat, chicken, monkey, rat, or mouse.

In some embodiments, the implantable device or a portion of the implantable device (such as the miniaturized ultrasonic transducer and the integrated circuit) is encapsulated by a biocompatible material (such as a biocompatible polymer), for example a copolymer of N-vinyl-2-pyrrolidinone (NVP) and n-butylmethacrylate (BMA), polydimethylsiloxane (PDMS), parylene, polyimide, silicon nitride, silicon dioxide, silicon carbide, alumina, niobium, or hydroxyapatite. The silicon carbide can be amorphous silicon carbide or crystalline silicon carbide. The biocompatible material is preferably impermeable to water to avoid damage or interference to electronic circuitry within the device. In some embodiments, the implantable device or portion of the implantable device is encapsulated by a ceramic (for example, alumina or titania) or a metal (for example, steel or titanium). In some embodiments, the electrodes or a portion of the electrodes are not encapsulated by the biocompatible material.

The miniaturized ultrasonic transducer of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di)fluoride (PVDF), and lead magnesium niobate-lead titanate (PMN-PT).

In some embodiments, the miniaturized bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. The height h of the miniaturized bulk piezoelectric transducer is defined as the distance along the shortest aspect ratio. The height of the bulk piezoelectric transducer is equal to one half of the resonant frequency ($\lambda$) of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 μm to about 500 μm (such as about 40 to about 400 μm, or about 100 μm to about 250 μm). In some embodiments, the height of the piezoelectric transducer about 3 mm or less (such as about 2 mm or less, about 1 mm or less, about 500 μm or less, about 400 μm or less, 250 μm or less, about 100 μm or less, or about 40 μm or less). In some embodiments, the height of the piezoelectric transducer is about 20 μm or more (such as about 40 μm or more, about 100 μm or more, about 250 μm or more, about 400 μm or more, about 500 μm or more, or about 1 mm or more) in length.

The miniaturized ultrasonic transducer is connected two electrodes; the first electrode is attached to a first face of the transducer and the second electrode is attached to a second face of the transducer, wherein the first face and the second face are opposite sides of the transducer along the height dimension. In some embodiments, the electrodes comprise silver, gold, platinum, platinum-black, poly(3,4-ethylenedioxythiophene) (PEDOT), a conductive polymer (such as conductive PDMS or polyimide), a carbon fiber, or nickel.

In some embodiments, the implantable devices are configured to engage with nervous tissue. In some embodiments, engagement of the nervous tissue does not completely surround the nervous tissue. In some embodiments, the nervous tissue is part of the central nervous system, such as the brain (e.g., cerebral cortex, basal ganglia, midbrain, medulla, pons, hypothalamus, thalamus, cerebellum, pallium, or hippocampus) or spinal cord. In some embodiments, engagement with brain tissue includes electrodes that are implanted in the tissue, whereas the body of the implantable device is located outside of the tissue. In some embodiments, the nervous tissue is part of the peripheral nervous system, such as a peripheral nerve.

In some embodiments, the implantable device is used to detect epileptic activity. See, for example, Mohseni et al., *Guest editorial: Closing the loop via advanced neurotechnologies*, IEEE Transactions on Neural Systems and Rehabilitation Engineering, vol. 20, no. 4, pp. 407-409 (2012). In some embodiments, the implantable device is used to optimize a cochlear implant. See, for example, Krook-Magnuson et al., *Neuroelectronics and biooptics: Closed-loop technologies in neurological disorders*, JAMA Neurology, vol. 72, no. 7, pp. 823-829 (2015).

In some embodiments, the implantable device is engaged with a muscle, such as skeletal muscle, smooth muscle or cardiac muscle. In some embodiments, electrodes from the implantable device are engaged with the muscle, such as skeletal muscle, cardiac muscle, or smooth muscle.

EXEMPLARY EMBODIMENTS

Embodiment 1

An implantable device, comprising:
an ultrasonic transducer configured to receive ultrasonic waves that power the implantable device and encode a trigger signal;
a first electrode and a second electrode configured to be in electrical communication with a tissue and emit an electrical pulse to the tissue in response to the trigger signal; and
an integrated circuit comprising an energy storage circuit.

Embodiment 2

The implantable device of embodiment 1, wherein the electrical pulse is a current pulse.

Embodiment 3

The implantable device of embodiment 1, wherein the electrical pulse is a voltage pulse.

Embodiment 4

The implantable device of any one of embodiments 1-3, wherein the first electrode and the second electrode are within the tissue or in contact with the tissue.

Embodiment 5

The implantable device of any one of embodiments 1-4, wherein the integrated circuit comprises a digital circuit.

Embodiment 6

The implantable device of any one of embodiments 1-5, wherein the integrated circuit comprises a mixed-signal integrated circuit configured to operate the first electrode and the second electrode.

Embodiment 7

The implantable device of any one of embodiments 1-6, wherein the integrated circuit comprises a power circuit comprising the energy storage circuit.

Embodiment 8

The implantable device of any one of embodiments 1-7, comprising a body that comprises the ultrasonic transducer and the integrated circuit, wherein the body is about 5 mm or less in length in the longest dimension.

Embodiment 9

The implantable device of any one of embodiments 1-8, comprising a non-responsive reflector.

Embodiment 10

The implantable device of any one of embodiments 1-9, wherein the tissue is muscle tissue, organ, or nervous tissue.

Embodiment 11

The implantable device of any one of embodiments 1-10, wherein the tissue is part of the peripheral nervous system or the central nervous system.

Embodiment 12

The implantable device of any one of embodiments 1-10, wherein the tissue is a skeletal muscle, smooth muscle, or cardiac muscle.

Embodiment 13

The implantable device of any one of embodiments 1-12, comprising three or more electrodes.

Embodiment 14

The implantable device of any one of embodiments 1-13, wherein the integrated circuit comprises an analog-to-digital converter (ADC).

Embodiment 15

The implantable device of any one of embodiments 1-14, wherein the implantable device comprises a modulation circuit configured to modulate a current flowing through the ultrasonic transducer.

Embodiment 16

The implantable device of embodiment 15, wherein the modulated current encodes information, and the ultrasonic transducer is configured to emit ultrasonic waves encoding the information.

Embodiment 17

The implantable device of embodiment 16, wherein the information comprises a signal verifying that an electrical pulse was emitted by the implantable device, a signal indicating an amount of energy stored in the energy storage circuit, or a detected impedance.

Embodiment 18

The implantable device of any one of embodiments 15-17, wherein the implantable device comprises a digital circuit configured to operate the modulation circuit.

Embodiment 19

The implantable device of embodiments 18, wherein the digital circuit is configured to transmit a digitized signal to the modulation circuit.

Embodiment 20

The implantable device of embodiment 19, wherein the digitized signal comprises a unique implantable device identifier.

Embodiment 21

The implantable device of any one of embodiments 15-20, wherein the modulation circuit comprising a switch.

Embodiment 22

The implantable device of embodiment 21, wherein the switch comprises a field effect transistor (FET).

Embodiment 23

The implantable device of any one of embodiments 1-22, wherein the ultrasonic transducer has a length of about 5 mm or less in the longest dimension.

Embodiment 24

The implantable device of any one of embodiments 1-23, wherein the body has a volume of about 5 mm3 or less.

Embodiment 25

The implantable device of any one of embodiments 1-24, wherein the body has a volume of about 1 mm3 or less.

Embodiment 26

The implantable device of any one of embodiments 1-25, wherein the ultrasonic transducer is configured to receive ultrasonic waves from an interrogator comprising one or more ultrasonic transducers.

Embodiment 27

The implantable device of any one of embodiments 1-26 wherein the ultrasonic transducer is a bulk piezoelectric transducer.

Embodiment 28

The implantable device of embodiment 27, wherein the bulk ultrasonic transducer is approximately cubic.

Embodiment 29

The implantable device of any one of embodiments 1-26, wherein the ultrasonic transducer is a piezoelectric micro-machined ultrasonic transducer (PMUT) or a capacitive micro-machined ultrasonic transducer (CMUT).

Embodiment 30

The implantable device of any one of embodiments 1-29, wherein the implantable device is implanted in a subject.

Embodiment 31

The implantable device of embodiment 30, wherein the subject is a human.

Embodiment 32

The implantable device of any one of embodiments 1-31, wherein the implantable device is at least partially encapsulated by a biocompatible material.

Embodiment 33

The implantable device of embodiment 32, wherein at least a portion of the first electrode and the second electrode are not encapsulated by the biocompatible material.

Embodiment 34

The implantable device of embodiment 32 or 33, wherein the biocompatible material is a copolymer of N-vinyl-2-pyrrolidinone (NVP) and n-butylmethacrylate (BMA), polydimethylsiloxane (PDMS), parylene, polyimide, silicon nitride, silicon dioxide, alumina, niobium, hydroxyapatite, silicon carbide, titania, steel, or titanium.

Embodiment 35

The implantable device of any one of embodiments 32-34, wherein the biocompatible material is a ceramic or a metal.

Embodiment 36

A system comprising one or more implantable devices according to any one of embodiments 1-35 and an interrogator comprising one or more ultrasonic transducers configured to transit ultrasonic waves to the one or more implantable devices, wherein the ultrasonic waves power the one or more implantable devices.

Embodiment 37

The system of embodiment 36, wherein the ultrasonic waves encode a trigger signal.

Embodiment 38

The system of embodiment 36 or 37, wherein the system comprises a plurality of implantable devices.

Embodiment 39

The system of embodiment 38, wherein the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices.

Embodiment 40

The system of embodiment 38, wherein the interrogator is configured to simultaneously receive ultrasonic backscatter from at least two implantable devices.

Embodiment 41

The system of embodiment 38, wherein the interrogator is configured to transit ultrasonic waves to the plurality of implantable devices or receive ultrasonic backscatter from the plurality of implantable devices using time division multiplexing, spatial multiplexing, or frequency multiplexing.

Embodiment 42

The system according to any one of embodiments 38-41, wherein the interrogator is configured to be wearable by a subject.

Embodiment 43

A closed-loop system, comprising:
(a) a first device configured to detect a signal;
(b) an interrogator comprising one or more ultrasonic transducers configured to receive the ultrasonic backscatter encoding the signal and emit ultrasonic waves encoding a trigger signal; and
(c) a second device configured to emit an electrical pulse in response to the trigger signal, wherein the second device is implantable, comprising:
an ultrasonic transducer configured to receive ultrasonic waves that power the second device and encode a trigger signal;
a first electrode and a second electrode configured to be in electrical communication with a tissue and emit an electrical pulse to the tissue in response to the trigger signal; and an integrated circuit comprising an energy storage circuit.

Embodiment 44

The system of embodiment 43, wherein the signal is an electrophysiological pulse, a temperature, a molecule, an ion, pH, pressure, strain, or bioimpedance.

Embodiment 45

The system of embodiment 43 or 44, wherein the first device is implantable.

Embodiment 46

The system of any one of embodiments 43-45, wherein the first device comprises:
a sensor configured to detect the signal;
an integrated circuit comprising a modulation circuit configured to modulate a current based on the detected signal, and a first ultrasonic transducer configured to emit an ultrasonic backscatter encoding the detected signal from the tissue based on the modulated current

Embodiment 47

The system of embodiment 46, wherein the sensor comprises a first electrode and a second electrode configured to be in electrical communication with a second tissue and detect and electrophysiological signal.

Embodiment 48

The system of embodiment 47, wherein the first tissue and the second tissue are the same tissue.

Embodiment 49

The system of embodiment 47, wherein the first tissue and the second tissue are different tissues.

Embodiment 50

The system of any one of embodiments 43-49, wherein the first electrode and the second electrode of the second device are within the first tissue or contact the tissue.

Embodiment 51

The system of any one of embodiments 43-50, wherein the integrated circuit of the second device comprises a digital circuit.

Embodiment 52

The system of any one of embodiments 43-51, wherein the integrated circuit of the second device comprises a mixed-signal integrated circuit configured to operate the first electrode and the second electrode.

Embodiment 53

The system of any one of embodiments 43-52, wherein the integrated circuit comprises a power circuit comprising the energy storage circuit.

Embodiment 54

The system of any one of embodiments 43-53, wherein the first implantable device or the second implantable device comprises a body that comprises the ultrasonic transducer and the integrated circuit, wherein the body is about 5 mm or less in length in the longest dimension.

Embodiment 55

The system of any one of embodiments 43-54, wherein the tissue is muscle tissue, an organ, or nervous tissue.

Embodiment 56

The system of any one of embodiments 43-55, wherein the first device and the second device are implanted in a subject.

Embodiment 57

The system of embodiment 56, wherein the subject is a human.

Embodiment 58

A computer system, comprising:
an interrogator comprising one or more ultrasonic transducers;
one or more processors;
non-transitory computer-readable storage medium storing one or more programs configured to be executed by the one or more processors, the one or more programs comprising instructions for operating the interrogator to emit ultrasonic waves encoding a trigger signal that signals an implantable device to emit an electrical pulse to a tissue.

Embodiment 59

The computer system of embodiment 58, wherein the interrogator is operated to emit ultrasonic waves encoding the trigger signal in response to a detected physiological signal.

Embodiment 60

The computer system of embodiment 58, wherein the physiological signal comprises an electrophysiological pulse, a temperature, a molecule, an ion, pH, pressure, strain, or bioimpedance.

Embodiment 61

The computer system of embodiment 59 or 60, wherein the one or more programs comprise instructions for detecting the physiological signal based on ultrasonic backscatter encoding the physiological signal emitted from a second implantable device.

Embodiment 62

The computer system of any one of embodiments 59-61, wherein the one or more programs comprise instructions for determining a location of the first implantable device or the second implantable device relative to the one or more ultrasonic transducers of the interrogator.

Embodiment 63

The computer system of any one of embodiments 59-62, wherein the one or more programs comprise instructions for detecting movement of the first implantable device or the second implantable device.

Embodiment 64

The computer system of embodiment 63, wherein the movement comprises lateral movement.

Embodiment 65

The computer system of embodiment 63 or 64, wherein the movement comprises angular movement.

Embodiment 66

A method of electrically stimulating a tissue, comprising:
receiving ultrasonic waves at one or more implantable devices;
converting energy from the ultrasonic waves into an electrical current that charges an energy storage circuit;
receiving a trigger signal encoded in the ultrasonic waves at the one or more implantable devices; and
emitting an electrical pulse that stimulates the tissue in response to the trigger signal.

Embodiment 67

A method of electrically stimulating a tissue, comprising emitting ultrasonic waves encoding a trigger signal from an interrogator comprising one or more ultrasonic transducers to one or more implantable devices configured to emit an electrical pulse to the tissue in response to receiving the trigger signal.

Embodiment 68

The method of embodiment 66 or 67, wherein the trigger signal is transmitted in response to a detected physiological signal.

Embodiment 69

The method of embodiment 69, wherein the physiological signal comprises an electrophysiological pulse, a temperature, a molecule, an ion, pH, pressure, strain, or bioimpedance.

Embodiment 70

The method of any one of embodiments 66-69, wherein the tissue is a muscle tissue, an organ, or a nervous tissue.

Embodiment 71

The method of any one of embodiments 66-70, comprising implanting the one or more implantable devices in a subject.

Embodiment 72

The method of embodiment 71, wherein the subject is a human.

Embodiment 73

The method of any one of embodiments 66-72, comprising determining a location of the one or more implantable devices.

Embodiment 74

The method of any one of embodiments 66-73, comprising detecting angular or lateral movement of the one or more implantable devices.

Embodiment 75

A method of stimulating a tissue, comprising:
receiving ultrasonic waves at one or more implantable devices configured to detect a physiological signal;
converting energy from the ultrasonic waves into an electrical current that flows through a modulation circuit;
detecting the physiological signal;
modulating the electrical current based on the detected physiological signal;
transducing the modulated electrical current into an ultrasonic backscatter that encodes information related to the detected physiological signal; and
emitting the ultrasonic backscatter to an interrogator comprising one or more transducer configured to receive the ultrasonic backscatter;
emitting ultrasonic waves from the interrogator to one or more implantable devices configured to emit an electrical pulse to the tissue;
converting energy from the ultrasonic waves emitted from the interrogator to the one or more implantable devices configured to emit the electrical pulse into an electrical current that charges an energy storage circuit;
emitting ultrasonic waves encoding a trigger signal from the interrogator;
receiving the trigger signal at the one or more implantable devices configured to emit the electrical pulse; and
emitting an electrical pulse that stimulates the tissue in response to the trigger signal.

Embodiment 76

The method of embodiment 75, wherein the physiological signal comprises an electrophysiological pulse, a temperature, a molecule, an ion, pH, pressure, strain, or bioimpedance.

EXAMPLES

Example 1—Manufacture of an Implantable Device

In short form, the assembly steps of the implantable device are as follows:
1. Attach ASIC to PCB.
2. Wirebond ASIC ports to PCB
3. Attach piezoelectric element to PCB.
4. Wirebond piezoelectric element ports to PCB.
5. Encapsulate full device except for recording electrodes.

The ASIC measures 450 µm by 500 µm by 500 µm and is fabricated by Taiwan Semiconductor Manufacturing Company's 65 nm process. Each chip contains two transistors with 5 ports each: source, drain, gate, center, and bulk. Each FET uses the same bulk, so either bulk pad can be bonded to, but the transistors differ in that the transistor padded out to the top row does not contain a resistor bias network whereas the transistor padded out in the bottom row does. The chip additionally contains smaller pads for electroplating. The same process can be applied to ASIC's with more complex circuitry and thus more pads. These pads were not used in this example. Three versions of the FET were taped out:

Die 1: Long channel FET with threshold voltage: 500 mV
Die 2: Short channel FET with threshold voltage at 500 mV
Die 3: Native FET with threshold voltage at 0 mV Confirmation of electrical characteristics of these FETs were measured using a specially designed CMOS characterization board which contained of a set of pads as wirebonding targets and a second set of pads in which wires were soldered to. A sourcemeter (2400 Sourcemeter, Keithley Instruments, Cleveland, Ohio) was used to supply $V_{DS}$ to the FET and measure $I_{DS}$. An adjustable power supply (E3631A, Agilent, Santa Clara, Calif.) was used to modulate $V_{Gs}$ and the I-V characteristics of the FETs were obtained. Uncharacteristic IV curves for type 2 dies were consistently measured, and upon impedance measurement, found that the short channel of the die 2s would short out the FET.

The piezoelectric element is lead-zirconium titanate (PZT). It is purchased as a disc from APC International and diced into. 750 μm×750 μm×750 μm cubes using a wafer saw (DAD3240, Disco, Santa Clara, Calif.) with a ceramic blade (PN CX-010-'270-080-H). This mote size was chosen as it maximized power transfer efficiency. For more details, see Seo et al., *Neural dust: an ultrasonic, low power solution for chronic brain-machine interfaces*, arXiv: 1307.2196v1 (Jul. 8, 2013).

The implantable device was implanted in the sciatic nerve of a Long-Evans rat. The nerve is a large diameter nerve bundle which innervates the hind limb. The nerve is between 1 and 1.4 mm in diameter, and its size and accessibility make it an ideal candidate for device implantation. While several iterations of the implantable device were made, the following example discusses the development of two versions implanted in rat models.

The implantable device substrate integrates the ASIC with the piezoelectric element and recording electrodes. The first version of the implantable device used custom-designed PCBs purchased from The Boardworks (Oakland, Calif.) as a substrate. The PCBs were made of FR-4 and were 30 mil (approximately 0.762 mm) in thickness. The dimensions of the board were 3 mm×1 mm. This design was the first attempt an integrated communication and sense platform, so pad size and spacing was chosen to facilitate assembly at the cost of larger size. To conserve PCB real-estate, each face of the PCB included pads for either the piezoelectric element or the ASIC and its respective connections to the PCB. Additionally, two recording pads were placed on the ASIC-face of the board. All exposed electrodes were plated with ENIG by The Boardworks. The pad for the ASIC to sit on was 500 μm by 500 μm, chosen to fit the size of the die. The wirebond target pad size was chosen to be 200 μm by 200 μm and spaced roughly 200 μm away from the edge of the die in order to give enough clearance for wirebonding (discussed below). Electrode size and spacing varied and were empirically optimized using four pairs of electrodes spaced 2 mm, 1.5 m, 1 mm, and 0.5 mm away from each other. It was found that electrodes spacing greater than 1.5 mm were optimal for recording. Minimal signal attenuation was noted between 2 mm and 1.5 mm, and signal strength decreased by about 33% between 1.5 mm and 1 mm.

Figure 14A:
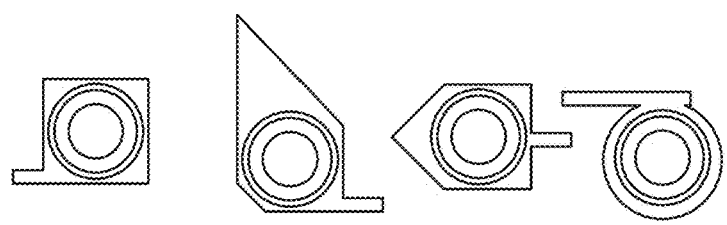
FIG. 14A shows different geometries of vias used to connect components of the implantable device.

In the second iteration of implantable device, three concerns primary concerns were addressed: 1) size, 2) ease of wirebonding, 3) implantation/communication. First, to decrease board thickness the FR-4 substrate was replaced with a 2 mil (about 50.8 μm) thick polyimide flexible PCB (AltaFlex, Santa Clara, Calif.), as well as thinning the ASIC (Grinding and Dicing Services Inc., San Jose, Calif.) to 100 μm. To facilitate bonding, the ASIC and PZT coupon were moved to the same side, with only the recording electrodes on the backside of the substrate. While putting the ASIC and PZT coupon on the same side of the board does impose a limit on how much the substrate size can be reduced, spacing between the electrodes restricted the board length of at least 2 mm. To push minimization efforts ASIC bonding pads were reduced to 100 μm by 100 μm, but the 200 μm spacing between bonding pads and the ASIC itself had to be maintained to provide space for wirebonding. The attachment pads for the PZT coupon was also shrunk and placed closer to the edge of the board, with the rationale that the PZT coupon did not have to wholly sit on the board, but could hang off it. Additionally, the location of the pads relative to the ASIC was also modified to facilitate bonding. In the original design, the bond pad layout surrounding the ASIC required two wirebonds to cross. This is not impossible, but very difficult to avoid shorting the pads. Thus, the pad layout was shifted so that the bonds are relatively straight paths. Finally, during animal experiments, it was found that alignment of the implantable device was quite difficult. To combat this, four 1 inch test leads that extended off the board were added, two of which connected directly to the source and drain of the device to harvest power could be measured and to use that as an alignment metric. The other two leads connect to the gate and center ports in order to obtain a ground truth signal. In order to prevent confusion over which lead belonged to which port, the vias were given unique geometries. See FIG. 14A.

Figure 14B:
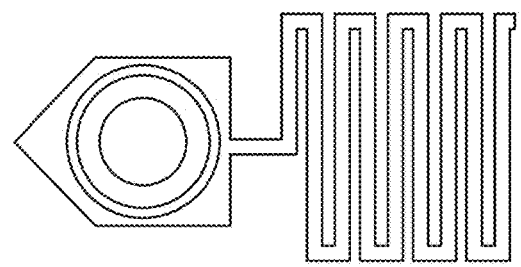
FIG. 14B shows a serpentine trace configuration for deformable interconnects.

There was some fear that the test leads may be easily broken or would easily displace the mote if force was applied on them. Thus, a version with serpentine traces was designed. Serpentine traces (FIG. 14B) have often been used to enable deformable interconnects, as their structure allows them to "accordion" out. Conceptually, the serpentine trace design can be through of a series of cantilevers in series via connector beams.

Along with the presented designs, a miniaturized version of the implantable device using both sides of the substrate was also designed and assembled. In this design, the board measures roughly 1.5 mm by 0.6 mm by 1 mm. Due to the miniaturization of the board, a 5 mil silver wire "tail" was attached to the device for recording. This version was not tested in vivo.

The ASIC and PZT coupon were attached to the PCB substrate using adhesives. There are three majors concerns to choosing an adhesive: 1) the adhesive needs to fix the ASIC and PZT tightly enough that the ultrasonic power from wirebonding does not shake the components, 2) due to the sub-millimeter scales and pitches of the components/substrate pads, application of the adhesive was done in a relatively precise way, and 3) the adhesive must be electrically conductive.

Figure 15:
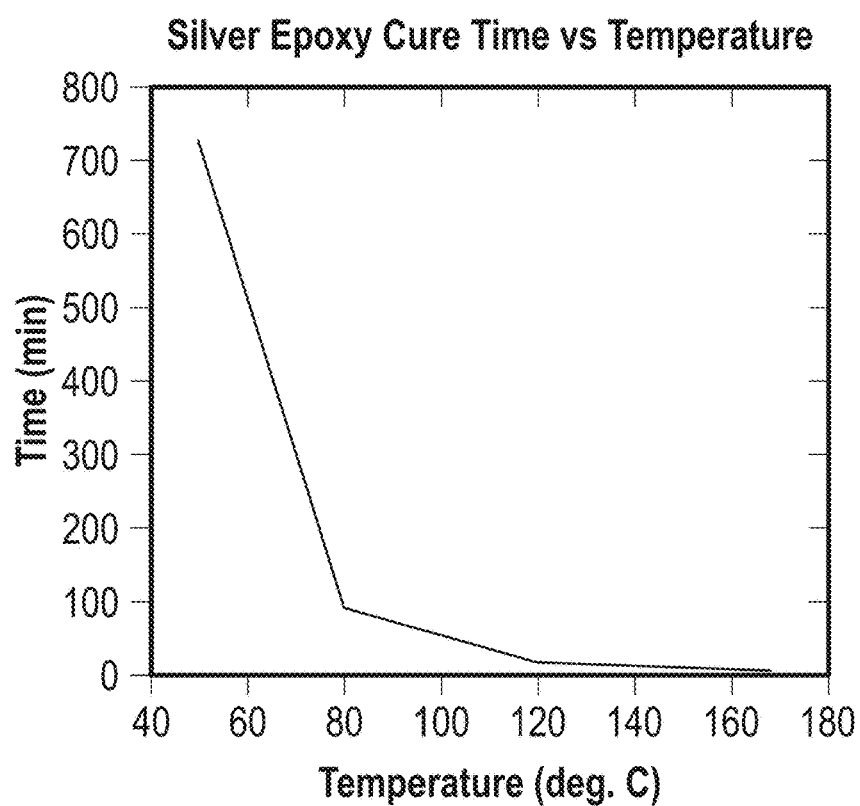
FIG. 15 shows the relationship between time and temperature for curing silver epoxy, an exemplary material for attaching wirebonds during the manufacture of the implantable device.

The ASIC and diced PZT were originally attached to the PCB substrate using a low temperature-curing solder paste. Solder paste consists of powder metal solder suspended as spheres in flux. When heat is applied, the solder balls begin to melt and fuse together. However, it was found that the curing of the solder paste would often result in translating or rotating the PZT coupon or mote during reflow. This presented problems for PZT alignment and power harvesting, as well as problems for wirebonding due to the bondpads no longer being appropriately positioned from the chip. However, it was found that a two-part silver epoxy, which simply consists of silver particles suspended in epoxy was capable of curing without repositioning the chip or PZT coupon. Thus, the ASIC and diced PZT were pasted onto the PCB using a two-part conductive silver epoxy (H20E, Epotek, Billerica, Mass.). The PCBs were then affixed to a glass slide using Kapton tape (Polyimide Film Tape 5413, 3M, St. Paul, Minn.) and put into a convection oven at 150° C. for 15 minutes to cure the epoxy. While higher temperatures could yield faster curing (FIG. 15), care was taken to avoid heating the PZT beyond 160° C., half the Curie temperature of the PZT. Heating the PZT any higher runs the risk of depolarizing the PZT. It was found that the 150° C. cure had no effect on the CMOS performance.

The connections between the top of the PZT and the PCB as well as the ASIC and the PCB were made by wirebonding 1 mil Al wire using an ultrasonic wedge bonder (740DB, West Bond, Scotts Valley, Calif.); in this method of bonding, the Al wire is threaded through the wedge of the bondhead and ultrasonic energy "scrubs" the Al wire against the substrate, generating heat through friction. This heat results in welding the two materials together.

Wirebonding to the ASIC was challenging to avoid shorts due to the size of the CMOS pads and the size of the foot of the wirebond. This problem was accentuated due to the positioning of the wirebonding targets in the first version of the implantable device board, which forced the feet of two bonds to be placed across the smaller width of the ASIC pad rather than the length. While thinner gold wire was available to use for bonding, the difficulty of bonding gold thermosonically with a wedge bonder made it impractical to use gold wires for bonding with this equipment. Furthermore, in order to effectively wirebond, it is important to have a flat and fixed substrate; hence, our original design of having the ASIC and PZT on different sides of the board often caused trouble during the wirebonding process in our first version of implantable boards. Thus, the substrate design choices made in the second iteration of the implantable device (moving ASIC and PZT to the same side, repositioning the pads to provide straight paths to wirebond targets) greatly improved wirebonding yield.

Finally, because an ultrasonic bonder was used, it was found that bonding to the PZT resulted in a charge build up would damage the chip once the PZT was fully bonded to the substrate. To avoid this, the source and drain test leads of the device were discharged to Earth ground directly prior to wirebonding the PZT.

The final step of the implantable device assembly is encapsulation. This step achieves two goals: 1) insulation of the PZT, bondpads, and ASIC from aqueous environments and 2) protection of the wirebonds between the ASIC/PZT coupon and the PCB. At the same time, there must be some method to either remove or prevent the encapsulant from covering the recording electrodes. Additionally, the encapsulant must not impede device implantation. Finally, while it is not crucial, it is of interest to choose an encapsulant that is optically transparent so that the device can be inspected for physical defects if some damage occurred during the encapsulation.

The first encapsulant used was Crystalbond (509', SPI Supplies, West Chester, Pa.). Crystalbond is an adhesive that is solid at room temperature but begins to soften' at 71° C. and melts into a viscous liquid at 121° C. Upon removing heat from the Crystalbond, it re-solidifies within minutes, allowing for good control. To encapsulate the implantable device, a small flake of Crystalbond was shaved off with a razor and placed directly over the device. The board was then heated using a hotplate, first bringing the temperature to around 70° C. when the flake would begin to deform and then slowly increasing the temperature until the Crystalbond became fully liquid. Once the edge of the liquid Crystalbond drop expanded past the furthest wirebond but not the recording pad, the hotplate was turned off and the board was quickly moved off the plate onto a cooling chuck where the Crystalbond would re-solidify.

While Crystal bond was effective, it was found that UV curable epoxide could give us better selectivity and biocompatibility, as well as rapid curing. First, a light-curable acrylic (3526, Loctite, Dusseldorf; Germany) was tested, which cures with exposure to ultraviolet light. A sewing needle was used as an applicator to obtain high precision and the epoxy was cured with a 405 nm laser point for 2 minutes. This epoxy worked well, but was not medical-grade and thus not appropriate for a biological implant. Thus, a medical-grade UV curable epoxy (OG116-31, EPO-TEK, Billercia, Mass.) was tried. The epoxy was cured in a UV chamber (Flash, Asiga, Anaheim Hills, Calif.) with 92 mW/cm$^2$ at 365 nm for 5 minutes. While this epoxy was slightly less viscous than the Loctite epoxy, using a sewing needle again as an applicator allowed for selective encapsulation. As an insulator and protection mechanism for the wirebonds; the epoxy was very effective, but was found to leak during prolonged submersion in water (~1 hour). A second medical grade epoxy which touted stability for up to a year, was considered (301-2, EPO-TEK, Billerica, Mass.), but was found to be not viscous enough and required oven-baking for curing. Despite the instability of the UV epoxy, the duration of use was suitable for acute in vivo experiments.

To improve encapsulant stability, parylene-C was also considered as an encapsulation material. Parylene-C is an FDA approved biocompatible polymer which is chemically and biologically inert, a good barrier and electrical insulator, and extremely conformal when vapor deposited). Vapor deposition of Parylene-C is achieved by vaporizing powder Parylene-C dimer at temperatures above 150° C. The vapor Parylene-C dimer is then heated at 690° C. in order for pyrolysis to occur, cleaving the Parylene-C dimer into monomers. The monomer then fills the chamber, which is kept at room temperature. The monomer almost instantaneously polymerizes once it comes into contact with any surfaces. For all devices, Paraylene-C was deposited using a parylene deposition system (SCS Labcoter 2 Parylene Deposition System, Specialty Coating Systems, Indianapolis, Ind.) with the parameters shown in Table 1. Note that the table indicates the chamber gauge temperature as 135° C. This is distinct from the actual chamber temperature; rather the chamber gauge is simply the vacuum gauge of the process chamber. It is important to keep the temperature to at least 135° C. to prevent parylene from depositing onto the gauge. For the first batch of FR-4 boards, parylene was addressed by selectivity by using Kapton tape to mask off the electrodes. However, it was found that due to the small pitch between the recording electrodes and the ASIC wirebonding targets, there was not enough surface area for the tape to affix well to the board and it often slipped off, resulting in coated electrode pads. In the second iteration of implantable device, a parylene coat was attempted using a strategy in which the entire board was coated, then remove the parylene off the electrodes with a probe tip. In order to assure that parylene was coated onto the entire device, the implantable devices were suspended in air by damping them between two stacks of glass slides.

TABLE 1

Parylene-C Deposition Parameters

| | |
|---|---|
| Furnace Temperature | 690 deg. C. |
| Chamber Gauge Temperature | 135 deg. C. |
| Vaporizer Temperature | 175 deg. C. |
| Base Pressure | 14 mTorr |
| Operating Pressure | 35 mTorr |
| Paralyene-C Mass | 5 g |

The following provides additional details for manufacturing the implantable device.

Before beginning to work with the PCBs, ASICs, or PZT coupons, prepare two sample holders for the dust boards. To do so, simply take two glass slides (3 mm×1 mm×1 mm slides work well) and put a strip of double-sided tape on the slide lengthwise. The tape will be used to fix the dust motes in place so that the rest of the steps can be performed. On one of the slides, also add a piece of Kapton tape (3M) sticky-side up on top of the double-sided tape. This slide will be the slide used for curing as the high temperature of the cure can cause problems with the adhesive on the double-sided tape.

Next, mix a small amount of silver paste by weighing out a 1:1 ratio of part A and part B in a weigh boat. A large amount of silver-epoxy is not needed for the assembly process. Shown below is roughly 10 g of epoxy (5 g of each part) which is more than enough for three boards, Note that the mixed-silver epoxy has a shelf life of two weeks if placed at 4° C. So leftover epoxy can and should be refrigerated when not in use. Additionally, older epoxies (several days to a week) tend to be slightly more viscous than fresh epoxy which can make application easier, The substrates come panelized and will need to be removed. Each board is connected to the panel at several attachment points on the test leads and vias—these attachment points can be cut using a micro-scalpel (Feather Safety Razor Co., Osaka, Japan). Once the PCB has been singulated, using carbon-fiber tipped tweezers. or ESD plastic tweezers, place the singulated PCB onto the high-temperature sample holder.

The diced/thinned die are shipped on dicing tape, which can make it tricky to remove the die. In order to reduce the adhesion between the die and tape, it can be helpful to deform the tape. Using carbon-tipped or ESD plastic tweezers, gently press the tape and work the tweezers in a circular motion around the die. To check if the die has been freed, gently nudge the chip with the tip of the tweezers. If the die does not come off easily, continue to press into tape surrounding the chip. Once the chip has come off, carefully place the chip onto the high-temperature sample holder next to its board. It is advisable to bring the sample holder to the chip rather than the other way around so that the chip is not in transit, Care must be taken in this step to avoid losing or damaging the die. Never force a die off the tape, as excessive force can cause a chip to fly off the tape.

Next, attach the die using silver epoxy. Under a microscope, use a pin or something equally fine to apply a small amount silver epoxy to the CMOS pad on the PCB. In this step, it is better to err on the side of too little epoxy than too much epoxy since more silver paste can always be applied, but removing silver paste is non-trivial. Small amounts of uncured epoxy can be scraped away with the same tool used for application, just ensure the epoxy has been wiped off the tool.

Once the epoxy has been placed on the pad, the ASIC can be placed onto the epoxy. Due to a CAD error, some of the chips have been reflected. It is important to take care that chips which are reflected have been oriented the correct way on the board to ensure no wires need to cross during wirebonding.

Once the ASICs have been situated on the boards correctly, the silver epoxy can be cured by placing it into an oven at 150° C. for 15 minutes. Note that different temperatures can be used if needed—see FIG. 15 for details. After the silver epoxy has been cured, double-check adhesion by gently pushing on each die, If the die moves; a second coat of silver epoxy will be needed.

To prepare for wirebonding, move the devices from the high-temperature sample holder to the regular sample holder. This change is necessary because the adhesion of double-sided tape is stronger than that of the Kapton tape so wirebonding will be made easier. A piece of double-sided tape should be good enough to affix the sample holder to the wirebonder's workholder. It is best to ensure that the workholder has not been previously covered with double-sided tape so that the test leads do not get accidentally stuck to anything. If necessary, clean-room tape can be used to provide additional clamping of the sample holder.

Ensure the wirebonder is in good condition by making bonds on the provided test-substrate using default settings. Ensuring that the wirebonder is in condition is important, as a damaged wedge will not bond well and effectively just damage the ASIC pads. Forward bonds (first bond on the die, second bond on the substrate) should be made in the following order: 1. Gate. 2. Bulk. 3. Center. 4. Drain. 5. Source. While it is not critical that the bonds be made in this order, this order minimizes the number of substrate reorientations and prevents accidental damage to the bonds due to the bondhead. Small angle adjustments of the workholder can be made to facilitate bonding; it is imperative that this bond be as straight as possible. In the case that the foot of the second bond lifts from the substrate, changing the number of bonds to one and bonding the foot again may help. If proper adhesion cannot be made, a potential solution is to connect the foot of the bond and the substrate using silver epoxy. Additionally, shorts caused by two bond-feet touching can be resolved by very carefully cutting away the bridging metal using a microscalpel.

Known working bonding parameters can be found in Table 2, below. These parameters are simply guidelines and should be modified as necessary. Needing excess power (greater than 490) is typically indicative of a problem: substrate fixing (both PCB to glass slide and CMOS to PCB), wedge condition, and pad condition should all be checked. In the case of pad condition, damaged pads due to previous wirebonding attempts will usually require higher power—in some cases, the devices are salvageable, but failed attempts to bond with power higher than 600 usually results in too much damage to the pads for good bonding.

TABLE 2

Westbond 7400B A1 Parameters for ASIC

| Bond # | Power | Time |
|---|---|---|
| 1 (ASIC) | 420 | 40 ms |
| 2 (Substrate) | 420 | 40 ms |

Post-wire bonding, the device should undergo electrical testing to ensure proper bonding. If using a type 1 die, the I-V characteristics should be roughly as shown in Table 3.

TABLE 3

Typical I-V characteristics for Type 1 Die under $V_{ds} = 0.1$ V

| $V_{gs}$ | $I_{ds}$ |
| --- | --- |
| 0 V | 0.5 µA |
| 0.1 V | 0.74 µA |
| 0.2 V | 10.6 µA |
| 0.3 V | 51.4 µA |
| 0.4 V | 0.192 mA |
| 0.5 V | 0.39 mA |
| 0.6 V | 1.14 mA |
| 0.7 V | 1.55 mA |
| 0.8 V | 1.85 mA |

If the I-V characteristics do not seem correct, a valuable troubleshooting method is checking the resistances between the drain and center, source and center, and drain and source. If the die is working properly, one should expect roughly 90 kΩ resistance between the drain and center and source and center, and roughly 180 kΩ between the drain and source.

After confirmation that the FET is connected properly, the PZT coupon should be attached. This is done in a similar fashion to attaching the ASIC: place a dab of silver epoxy using a sewing needle on the appropriate pad. It is best to put the epoxy dab on the back edge of the pad (towards the end of the board) since the PZT coupon will not be centered on the pad, but pushed back so that the coupon hangs off the board. Keep in mind that the polarity of the PZT coupon has a small effect on its efficiency. To determine whether or not the coupon is in the correct position, check if the bottom face is larger than the top face. Due to the path of the dicing saw, the bottom of the coupon, is slightly larger than the top of the coupon. Thus, the edges of the bottom face can be seen from a top down view, then the coupon has been placed in the same orientation as it was when the disk was diced.

Wirebonding the PZT is done in a similar manner to the ASIC (forward bonding, the PZT to the PCB). However, one crucial change is that the drain and source vias should be grounded. There is an earth ground port next to Westbond which can be accessed via a banana connector. As a guideline, the parameters shown in Table 4 have been known to work.

TABLE 4

Westbond 7400B A1 Parameters for PZT

| Bond # | Power | Time |
| --- | --- | --- |
| 1 (PZT) | 390 | 40 ms |
| 2 (Substrate) | 490 | 40 ms |

A successful bond may require several attempts depending on how well the PZT coupon is attached to the substrate. The more attempts that are made, the worse the mechanical structure of the PZT becomes (the silver coating will become damaged) so it is best to try to very quickly optimize the process. Bonds that fail due to foot detachment generally imply not enough power. Bonds that fail due to the wire breaking at the foot generally imply too much power.

After a successful bond is made, it is always good to do another electrical test to ensure that bonding the PZT has not damaged the ASIC.

As a final step, test wires were soldered to the vias and encapsulate the device, The test wires are 3 mil silver wires. Note that these wires are insulated: the insulation can be removed by putting the wire close to a flame (not in the flame) and watching the plastic melt and recede.

After soldering wires, the device can now be encapsulated. The encapsulant is OG116-31 medical-grade UV curable epoxy and should be dispensed using a sewing needle. An effective method is to put a large drop of epoxy over the PZT coupon and a large drop over the ASIC. Using a clean needle, push the droplet over the board so that the entire topside of the board is coated. The epoxy should wet the board, but not spill over due to its surface tension. Once the main body of the board is coated, the vias should also be coated, as well as the side faces of the piezo. The board can then be cured in a UV chamber for roughly 5 minutes. It has been found that the test wires can occasionally contact something in the UV chamber and short the ASIC. Thus, prior to putting the board in the chamber, it is good to wrap the wires down or place it on some tape in order to isolate them from any chamber surfaces.

Following curing, the backside should be coated. In particular the exposed PZT coupon which hangs over the board as well as the backside of the test vias and the two vias on the backside of the board which connect the electrodes to the topside of the board. This part can be a little tricky due to the small space between the backside vias and the electrodes, so it is best to start with a very small amount of epoxy and place it near the edge of the board, then drag the epoxy up towards the vias. The backside of the board should be cured in the same manner as the topside. Once the board is fully encapsulated, a final electrical test should be done, and upon passing, the implantable device is now complete.

Example 2—Set-Up for Testing Implantable Devices

Testing of implantable has always been tricky due to the thinness of the test leads that extend out from the board. Clipping onto and off of these vias for I-V measurements has often resulted in pulling the leads off the body of the device. Furthermore, due to the test leads, it is difficult to perform water-tank test measurements; as exposed electronics in water would result in shorts. In order to circumvent this issue, a PCB was designed to serve as a testbed for implantable device measurements. The PCB (Bay Area Circuits, Fremont, Calif.) was made of FR-4 and 60 mil thick; it includes four vias, distributed on the board to match the layout of the version two implantable device boards.

Gold header pins (Pin Strip Header, 3M, Austin, Tex.) were soldered into the vias so that they extended from the board on both sides of the board. This enabled us to place our devices onto the test bed, and tap into the implantable by accessing the header pins. Next, to insulate the vias, plastic caps made out of polyethylene terephthalate (PETG) were 3D printed (Flashforge Creator X, FlashForge, Jinhua, China). These caps were printed with a groove so that an O-ring could be placed inside the groove and create a waterproof seal around the header pins. The caps were connected to the board and compression was created by drilling 2 mm holes through the PCB and cap using a micro-mill (47158, Harbor Freight, Camarillo, Calif.) and screwing the cap and board together. Wires extending from the testbed were soldered to the header pins and the pins were then encapsulated. To measure the effectiveness of the seal, the boards were submerged in an aqueous 6 M NaCl solution and the resistance between the pins was measured using a Keithley 2400. A MATLAB script was written to automatically record and plot the resistance over time. A drop in the resistance would indicate that the seal was broken. As an additional test, a piece of litmus paper was also put under the plastic cap with the intention that if the cap leaked, the litmus paper would change color. The pins were encapsulated using the same medical grade epoxy used to encapsulate the implantable device boards, and parylene was deposited over the epoxy on the back side of the testboards for a completely waterproof barrier. The resistance between the two neighboring pins of the testbed submerged in salt water solution as a function of time for only epoxy insulation and epoxy plus parylene insulation was measured. Without a parylene barrier, the epoxy began to leak, allowing salt water to short out the pins of the testbed.

One version of the implantable device was 1 mm×3 mm×1 mm PCBs made of FR-4 with a PZT piezoelectric, silicon AS!C, and encapsulated using crystal bond. These were implanted into a the sciatic nerve of an Adult male Long-Evans rat anesthetized with a mixture of ketamine and xylazine IP. A ground truth measurement was obtained using a tungsten microwire with a 28G stainless steel needle electrode placed in the foot of the animal as a reference. Nerve activity was evoked using electrical stimulation and backscatter data was acquired by sending and receiving pressure waves using a transducer (V323-SU-F1 Olympus, Waltham, Mass.).

Figure 16:
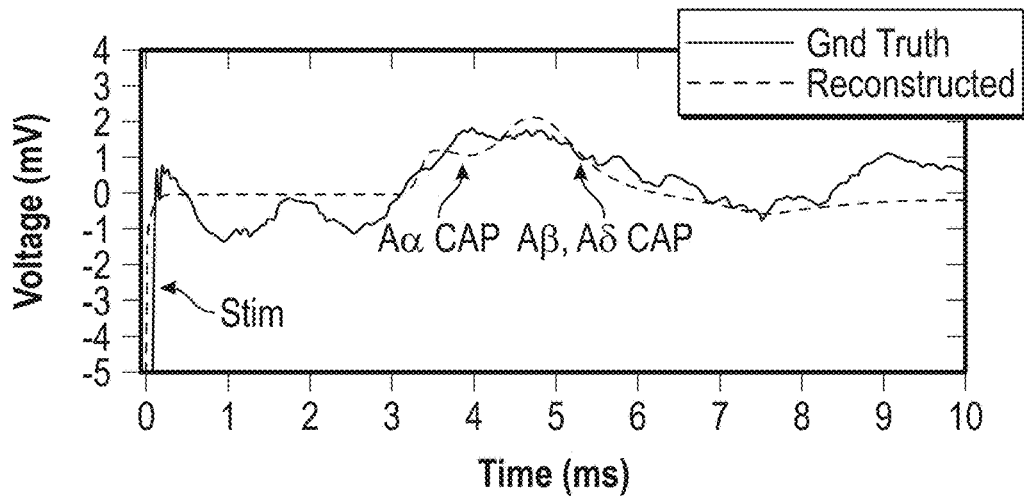
FIG. 16 shows a recorded electroneurogram (ENG) using an implantable device. The dotted trace shows the signal recorded by the ground truth electrode. A general profile including the compound action potentials was reconstructed from the acquired data, which matches the profile of the ground truth.

The original signal across the dust mote was later calculated from the backscatter data using MATLAB. A representative trace of the reconstructed signal versus the ground truth is shown in FIG. 16.

The reconstructed implantable device data followed the general profile of the ground truth, capturing the compound action potential of the nerve, but several features present in the reconstructed data (such as the "dips" found from the first to third second) could not be explained.

A second version of the implantable device was roughly 0.8 mm×3 mm×1 mm and used a polyimide substrate and medical-grade UV curable epoxy as encapsulation. A crucial change was the addition of test leads 1 in. long, allowing the voltage across the piezoelectric element to be measured, as well as take ground truth measurements by tapping into the recording electrodes. The same device implantation protocol was used in version two as was used in version one, but reconstruction of the backscattered signal was done on the fly using a custom transceiver board.

Example 3—Implantable Devices Encapsulated in Silicon Carbide

Rather than an epoxy encapsulant, silicon carbide (SiC) may be a more effective material for insulating and protecting the implantable device. SiC is formed by the covalent bonding of Si and C, forming tetrahedrally oriented molecules with short bond length and thus, high bond strength, imparting high chemical and mechanical stability. Amorphous SiC (a-SiC) has been welcomed by the biomedical community as a coating material as it can be deposited at much lower temperatures than ordinarily required by crystalline SiC and is an electrical insulator. Deposition of a-SiC is generally performed via plasma enhanced chemical vapor deposition (PECVD) or sputtering. Ongoing research using sputtered a-SiC has shown that it is difficult to achieve a pinhole free layer of SiC. Rather, PECVD using $SiH_4$ and $CH_4$ as precursors is capable of yielding impressive, pinhole free SiC films.

Furthermore, implanted a-SiC has shown impressive biocompatibility. Previous studies have shown that a 50 µm iridium shaft coated with a-SiC implanted in the rabbit cortex for ~20 days did not show the usual chronic inflammatory response of macrophage, lymphocyte, monocyte recruited to the insertion site. See Hess et al., *PECVD silicon carbide as a thin film packaging material for microfabricated neural electrodes*, Materials Research Society Symposium Proceedings, vol. 1009, doi: 10.1557/PROC-1009-U04-03 (2007).

Figure 17:
FIG. 17 illustrates a schematic for encapsulating an implantable device in silicon carbide.
Figure 17:
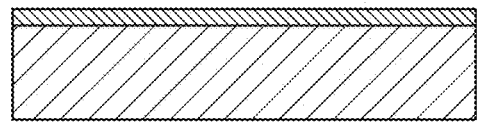
Figure 17:
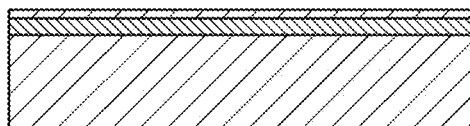
Figure 17:
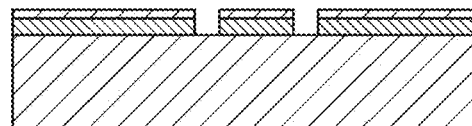
Figure 17:
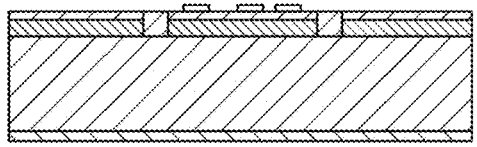
Figure 17:
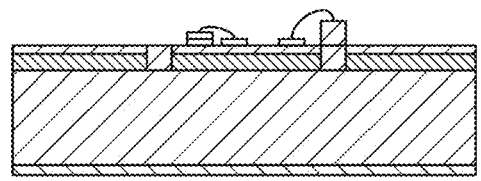
Figure 17:
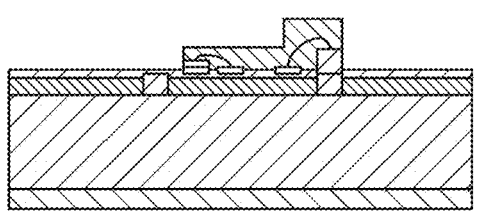
Figure 17:
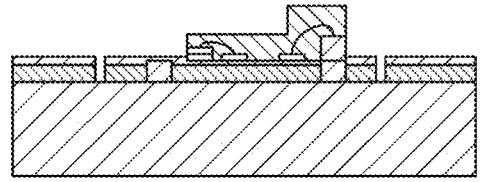
Figure 17:

It is interesting to consider an approach to implantable devices that would involve constructing the devices on silicon with a silicon carbide encapsulant for a truly chronic implant. A possible process is shown in FIG. 17. One of the largest challenges here is ensuring that the PECVD of SiC dues not depole the piezoelectric material. In order to have contamination-free films, it is important to deposit at a minimum temperature of 200° C., but below the Curie temperature of the piezoelectric transducer.

Example 4—Power Transfer to and Backscatter of a Miniaturized Ultrasonic Transducer A set of experiments were carried out with PZT due to the relative ease of obtaining PZT crystals with varying geometry. Metalized PZT sheets of several thicknesses were obtained (PSI-5A4E, Piezo Systems, Woburn, Mass. and PZT 84, APC Internationals, Mackeyville, Pa.), with a minimum PZT thickness of 127 µm. The PZT was fully encapsulated in PDMS silicon for biocompatibility.

The most commonly used method to dice PZT ceramics is to use a wafer dicing saw with an appropriate ceramic blade to cut PZT sheets into individual PZT crystals. The minimum resolution of the cut is determined by the kerf of the blade and can be as small as 30 µm.

Another possible option is to use a laser cutter. Unlike the dicing saw, laser cutting realizes the cuts by focusing a high-power laser beam onto a material, which melts, vaporizes, removes, and scribes the piece. The precision of laser cutting can be down to 10 µm and is limited by the wavelength of the laser. However, for treating sensitive samples such as PZT ceramics, the temperature at the site of cuts can be damaging to the piezoelectric performance of the material. Excimer laser cutting of ceramics uses UV laser to cut with excimer from noble gases, but such laser cutter is extremely expensive and no suitable services are currently available. As a result, a dicing saw was used to perform all the cuts.

In order to drive or extract electrical energy from the PZT, an electrical connection is made to both the top and bottom plates. The materials typically used as an electrode for PZT are silver or nickel. Silver is generally used for a wide variety of non-magnetic and AC applications and silver in the form of flakes suspended in a glass frit is usually screened onto the ceramic and fired. For high electric field DC applications, silver is likely to migrate and bridge the two plates. As a result, nickel, which has good corrosion resistance and does not electro-migrate as readily can be electroplated or vacuum deposited as an alternative.

Both materials can be soldered onto with the appropriate solder and flux. For instance, silver is soluble in tin, but a silver loaded solder can be used to prevent scavenging of silver in the electrode. Phosphor content from the nickel plating can make soldering tricky, but the correct flux can remove surface oxidation. However, when soldering, in order to avoid exceeding the Curie point and depoling the PZT sample, the soldering temperature must be between 240 and 300° C. Even at these temperatures, since the PZT is also pyroelectric, one must be careful not to exceed 2-4 seconds of soldering time.

Alternatively, an electrical connection can be made using either silver epoxy or low temperature soldering using solder paste. Standard two-part silver epoxy can provide a sufficient electrical conductivity and can be cured even at room temperature overnight. However, the joints tend to be fragile and can easily break during testing. The bond can be reinforced by using a non-conductive epoxy as an encapsulation but this additional layer presents a mechanical load to the PZT and can significantly dampen its quality factor. Low-temperature solder paste on the other hand undergoes a phase change between the temperature of 150 and 180° C. and can provide great electrical connection and a bond strength that is comparable to that achieved with flash soldering. Therefore, the low-temperature soldering approach was used.

Wafer dicing is capable of cutting PZTs into small crystals of 10's of µm. However, samples that are smaller than 1 mm in dimension are extremely difficult to handle with tweezers and bond to. In addition, due to the variation in the length of wire used to interface with top and bottom plates of PZT crystals (and therefore parasitic inductance and capacitance introduced by the wire) and the amount of solder paste dispensed across a number of samples, the impedance spectroscope measurements were inconsistent.

Figure 18:
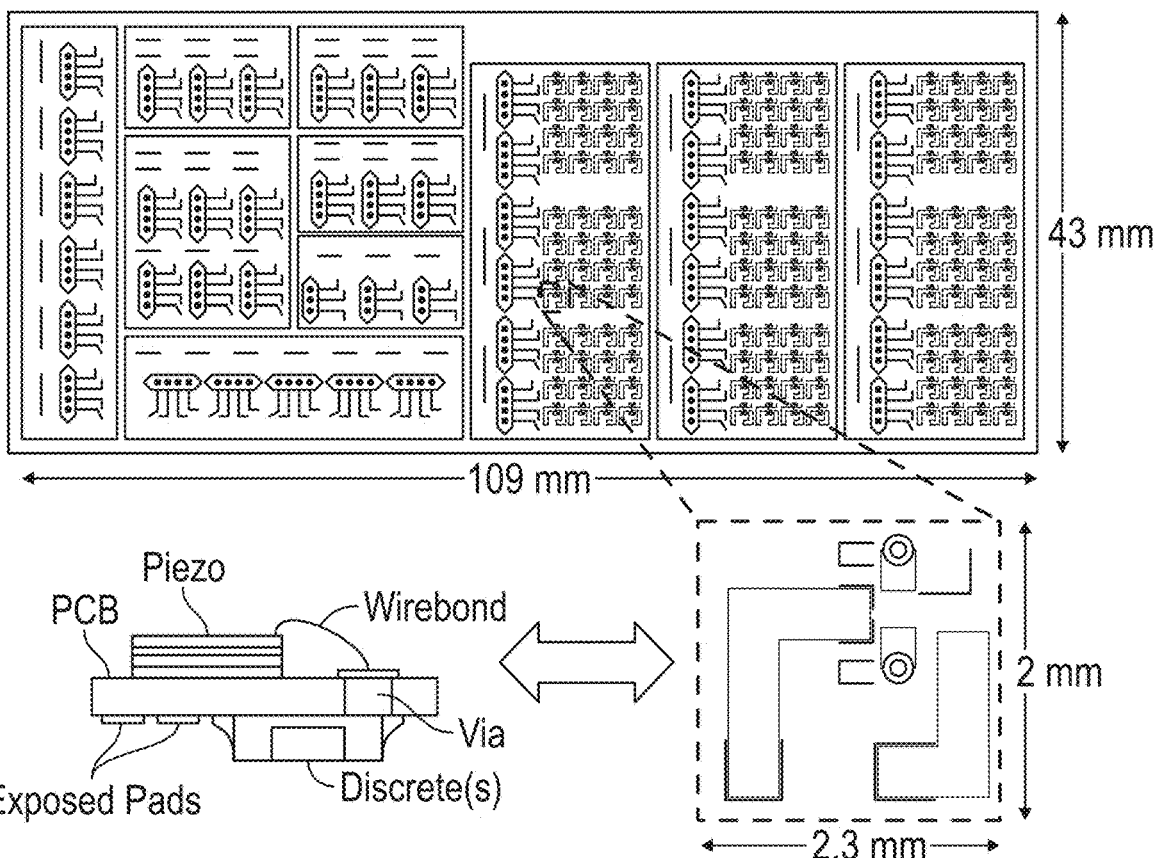
FIG. 18 shows an assembly prototype schematic and PCB.

Therefore, a 31 mil thick two-layer FR-4 PCB where all of the electrical interconnects short and de-embed out the parasitics from the wires and the board was fabricated. The fabricated board, which includes numerous test structures and a module for individually characterizing 127 µm, 200 µm, and 250 µm thick PZT crystals are shown with dimensions in FIG. 18. Each unit cell in the test module contains two pads with specified dimensions on one side of the PCB to interface with the PZT crystals and pads for discrete components for backscattering communication on the opposite side. The pitch between the unit cells is limited by the size of the discrete components and is roughly 2.3 mm×2 mm.

Figure 19A:
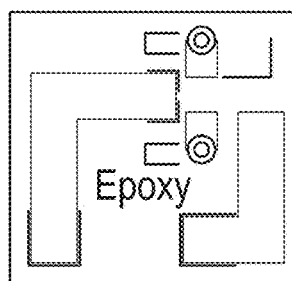
FIG. 19A-19E show processing steps to ensure that the desired miniaturized ultrasonic transducer (PZT) dimension is assembled on the PCB. At FIG. 19A, epoxy solder paste is dispensed onto the board. At FIG. 19B, a piezoelectric material is attached to the PCB. At FIG. 16C, the piezoelectric material is diced to form a bulk piezoelectric ultrasonic transducer of the desired size. At FIG. 19D, the ultrasonic transducer is wirebonded to the PCB. At FIG. 19E, the PCB and ultrasonic transducer is encapsulated in PDMS.
Figure 19B:
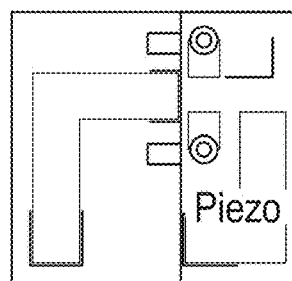
Figure 19C:
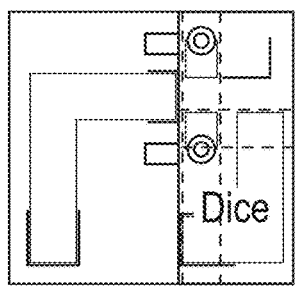
Figure 19D:
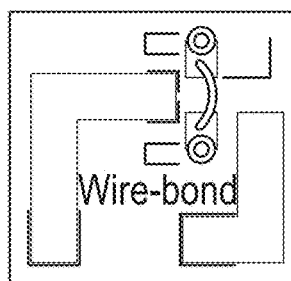
Figure 19E:
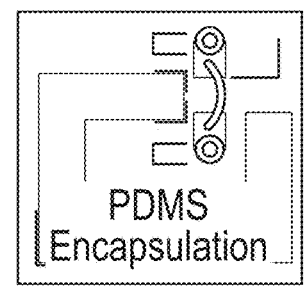

In order to avoid directly handling tiny PZT crystals, FIGS. 19A-E outline a scalable process flow to bond PZT onto the PCB. As shown in FIG. 19A, the solder paste is dispensed using a pump at a constant pressure and for a controlled amount of time on one of the pads on the top side. The pads are either 250 µm², 200 µm², or 127 µm² based on the thickness of the PZT used. FIG. 19B shows a PZT piece larger than the pad (that can be easily handled) is placed on top to cover the pads. The board and piezo assembly is baked in an oven to cure the solder paste. Therefore, PZT crystals are now bonded to pre-soldered bumped electrodes. FIG. 19C shows a wafer dicing saw makes a total of four cuts along the edges of the pad with the solder paste using alignment markers on the board, with non-bonded areas dropping off and leaving an array of small PZT crystals bonded to the PCB. FIG. 19D shows single wirebond makes an electrical contact between the top plate of the PZT and an electrode on the PCB, completing the circuit. Finally, FIG. 19E shows the entire assembly is encapsulated in PDMS (Sylgard 184, Dow Corning, Midland, Mich.) to protect the wirebond and provide insulation.

Since piezoelectric material is an electro-mechanical structure, its electrical and mechanical properties were characterized. The following details the test setup and techniques to perform such measurements.

Any electrical device can be modeled as a black box using a mathematical construct called two-port network parameters. The properties of the circuits are specified by a matrix of numbers and the response of the device to signals applied to its input can be calculated easily without solving for all the internal voltages and currents in the network. There are several different types of two-port network parameters, such as Z-parameters, Y-parameters, S-parameters, and ABCD-parameters, etc. and the conversion between different parameters can be easily derived. The apparatus that enables us to extract these parameters is called a vector network analyzer (VNA). A VNA incorporates directional couplers to decompose the voltage in each port into incident and reflected waves (based on impedance mismatching), and calculate the ratio between these waves to compute scattering or S-parameters.

Figure 20:
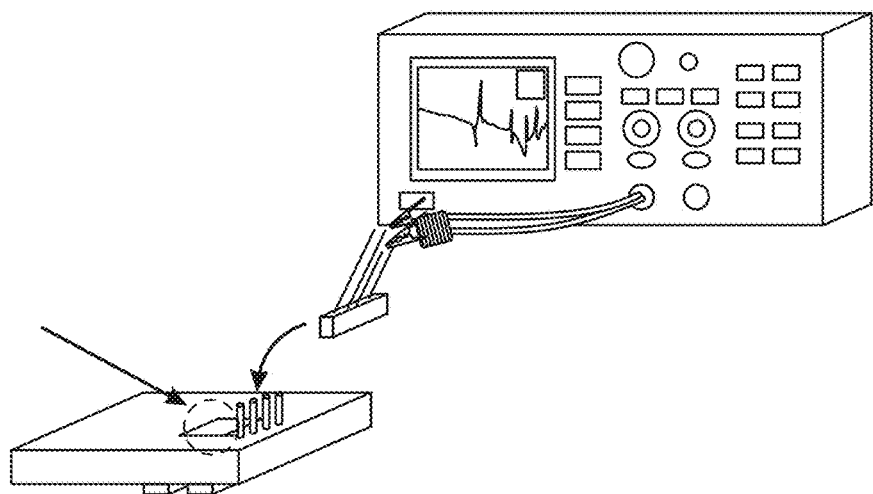
FIG. 20 shows a schematic for measuring electrical impedance with a vector network analyzer (VNA)

Before performing measurements using a VNA, one must calibrate the instrument since the internal directional couples are non-ideal. Calibration also allows us to move the reference plane of the measurement to the tips of the cable, i.e., calibrate out parasitics from the cable. There are several calibration standards but the most commonly used is open, short, and load calibration procedures. The measurement schematic is shown in FIG. 20. Alligator clips, which are soldered onto the ends of the coaxial cable, are used to interface with the top/bottom plates. The parasitics from the clips were not significant below 100 MHz.

As an example, a VNA (E5071C ENA, Agilent Technologies, Santa Clara, Calif.) was used to measure the electrical properties of a $(250\ \mu m)^3$ PZT crystal. It was noted that the measured capacitance of the PZT crystal vastly differs from the capacitance expected from a simple parallel-plate capacitance model due to significant parasitic capacitances from the PCB and the fixture (clip and connector). Since the VNA coefficients from the calibration step previously outlined only moved the measurement plane to the tips of the cable, open/short/load calibration structures fabricated on the same board were used to include the board and fixture parasitics. The measured PZT response matched the expected response after calibration.

Figure 21A:
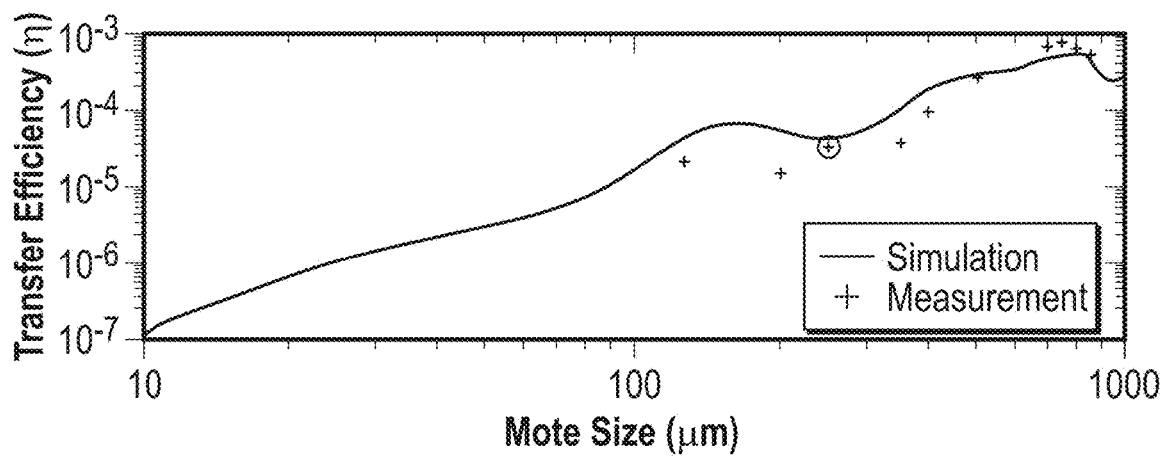
FIG. 21A shows that the measured power transfer efficiency at various bulk piezoelectric ultrasonic transducer sizes matches simulated behavior.
Figure 21B:
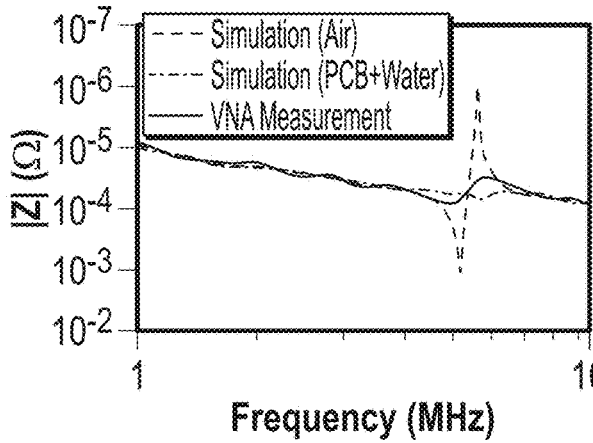
FIG. 21B shows that the measured impedance spectroscopy of a PZT crystal matches a simulation.

Using this calibration technique, the impedance of the PZT can be plotted as a function of frequency, as shown in FIG. 21B. From this plot, however, it is extremely difficult to determine whether there is any electro-mechanical resonance. When the simulation result with air backing (no mechanical clamping) was overlaid, it was noticed that the impedance spectroscopy matches well with the measurement at low and high frequencies, with the exception of noticeable peak at resonant frequency of roughly 6 MHz and its harmonics. Upon clamping and loading one side of PZT with PCB (FR-4), it was seen that a significant dampening of the resonant peaks from air backing. Despite a lack of observable resonance in the measurement, a small blimp around 6 MHz was observed, and the mechanical quality factor $Q_m$ can be calculated using the following equations, $$Q_m = \frac{f_a^2}{2Z_r C_p (f_a^2 - f_r^2)}$$

where $f_a$ and $f_r$ represent anti-resonant (where impedance is maximized) and resonant frequency (where impedance is minimized), $Z_r$ represents an impedance at resonance, and $C_p$ is the low-frequency capacitance. The calculated quality factor from the measurement is roughly 4.2 compared to 5.1 in simulation. According to the datasheet, the unloaded Q of the PZT is ~500, indicating that FR-4 backing and wirebonds are causing significant degradation of the quality factor. Despite the drastic reduction in the mechanical Q of the PZT crystals, experiments showed that the backscattered signal level only decreased by roughly ~19.

In the electrical characterization setup, the VNA has a built-in signal generator to provide the input necessary for characterization. In order to perform acoustic characterization of PZT, acoustic waves were generated and launched onto the sample to use as an input. This can be achieved with commercially available broadband ultrasonic transducers.

Figure 22:
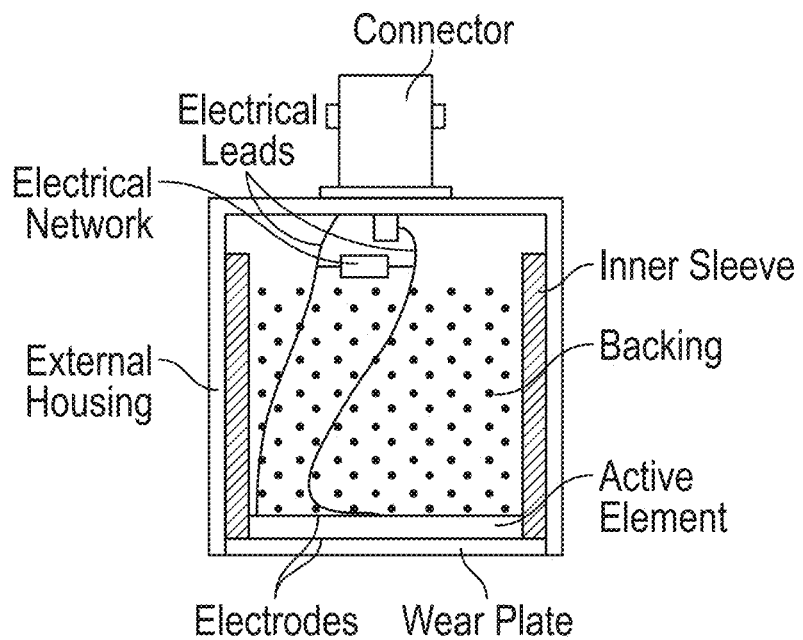
FIG. 22 is a schematic of an exemplary ultrasonic transducer that can be used as part of an interrogator.

FIG. 22 shows the composition of a representative transducer, which consists of a piezoelectric active element, backing, and wear plate. The backing is usually made from a material with high attenuation and high density to control the vibration of the transducer by absorbing the energy radiating from the back face of the active element while the wear plate is used to protect the transducer element from the testing environment and to serve as a matching layer.

Figure 23:
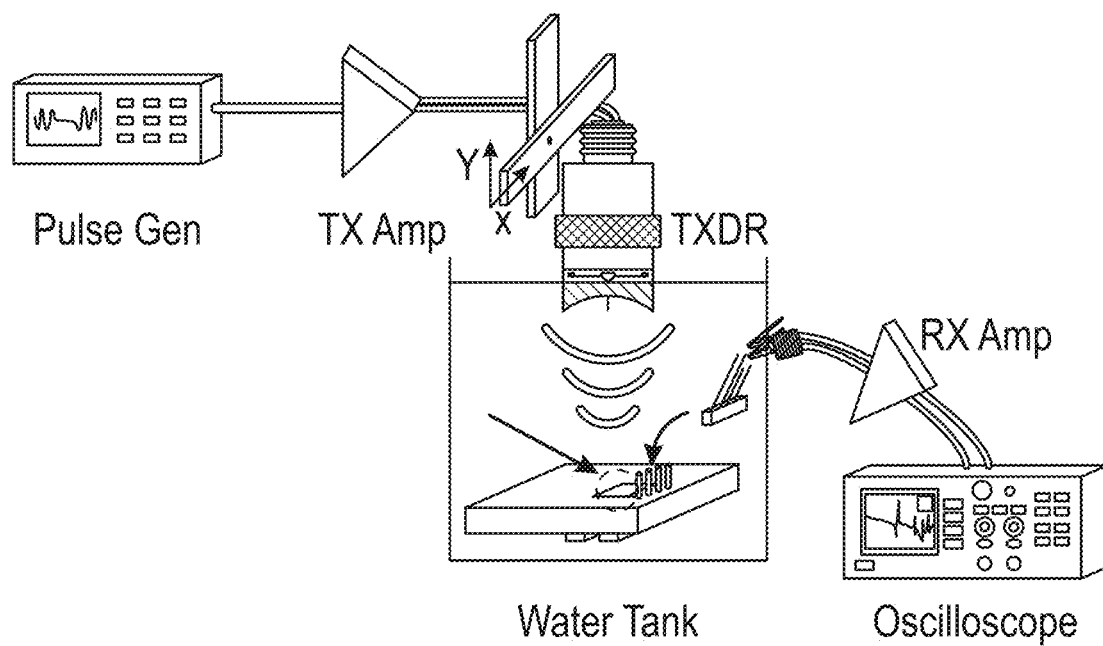
FIG. 23 is a schematic of a setup for acoustic characterization with a calibrated ultrasonic transducer for power delivery verification. The ultrasonic wave receiver is separate from the ultrasonic wave transmitter.

Ultrasonic power transfer tests were performed using the home-built setup shown in FIG. 23. A 5 MHz or 10 MHz single element transducer (6.3 mm and 6.3 mm active area, respectively, ~30 mm focal distance, Olympus, Waltham, Mass.) was mounted on a computer-controlled 2-axis translating stage (VelMex, Bloomfield, N.Y.). The transducer output was calibrated using a hybrid capsule hydrophone (HGL-0400, Onda, Sunnyvale, Calif.). Assembly prototypes were placed in a water container such that transducers could be immersed in the water at a distance of approximately 3 cm directly above the prototypes. A programmable pulse generator (33522B, Agilent Technologies Santa Clara, Calif.) and radio frequency amplifier (A150, ENI, Rochester, N.Y.) were used to drive transducers at specified frequencies with sinusoidal pulse trains of 10-cycles and a pulse-repetition frequency (PRF) of 1 kHz. The received signals were amplified with a radio frequency amplifier (BT00500-AlphaS-CW, Tomco, Stepney, Australia), connected to an oscilloscope (TDS3014B, Tektronix, Beaverton Oreg.) to collect ultrasound signal and record them using MATLAB.

Figure 24A:
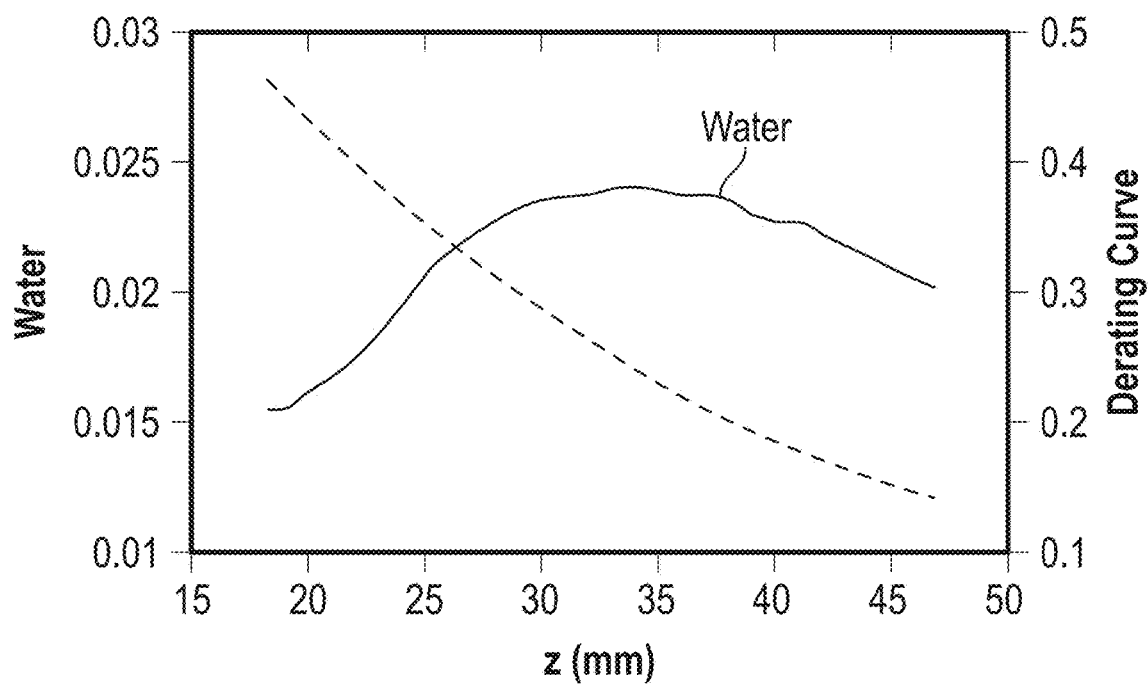
FIG. 24A shows the output power of a 5 MHz transducer as the hydrophone is moved away from the transducer's surface.
Figure 24B:
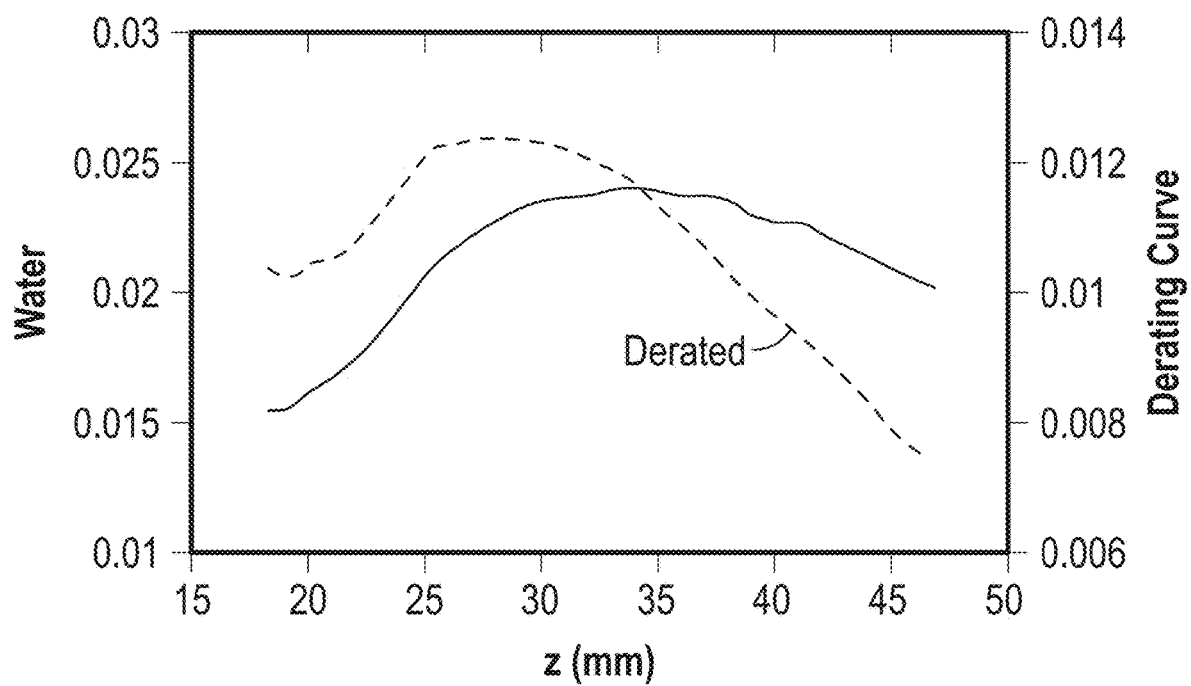
FIG. 24B shows de-rated peak is shifted to the left in relation to the water peak.
Figure 25A:
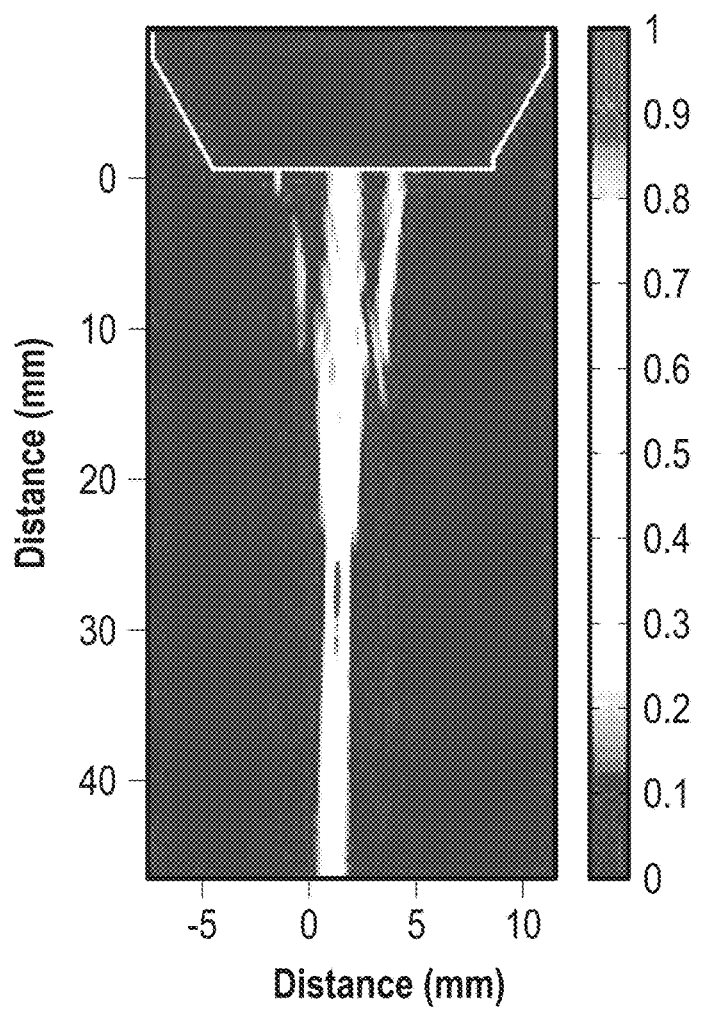
FIG. 25A shows the XZ cross-section of the transducer output, illustrating a Rayleigh distance and a clear transition from the near-field to far-field propagation.
Figure 25B:
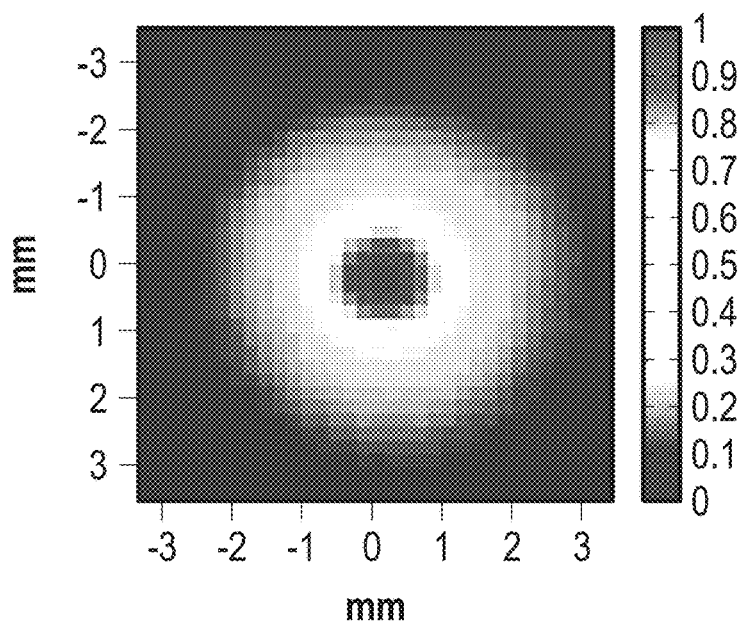
FIG. 25B shows the XY beam cross-section showing a 6 dB bandwidth of the beam at 2.2 mm.

FIG. 24A and FIG. 24B show a representative measurement of the output power of the 5 MHz transducer as a function of the distance between the surface of the transducer and the hydrophone (z-axis). The peak pressure in water was obtained at ~33 mm away from the transducer's surface (FIG. 24A), while the de-rated peak (with 0.3 dB/cm/MHz) was at ~29 mm (FIG. 24B). FIG. 25A shows the de-rated XZ scan of the transducer output, which show both near-field and far-field beam patterns and a Rayleigh distance or a focal point at ~29 mm, matching the de-rated peak in FIG. 24B. FIG. 25B shows a XY cross-sectional scan of the beam at the focal point of ~29 mm, where the 6 dB beamwidth measured roughly 2.2 mm.

The total integrated acoustic output power of the transducer at various frequencies over the 6 dB bandwidth of the beam was nominally kept at a spatial-peak temporal-average $I_{SPTA}$ of 29.2 $\mu W/cm^2$, resulting in a total output power of ~1 $\mu W$ at the focal point, with a peak rarefaction pressure of 25 kPa and a mechanical index (MI) of 0.005. Both the de-rated $I_{SPTA}$ and MI were far below the FDA regulation limit of 720 $mW/cm^2$ and 1.9, respectively (FDA 2008).

FIG. 21A shows the measured power delivery efficiency of the fully assembled prototype with cable loss calibrated out for various implantable device transducer sizes as compared to analytical predictions made for this same setup. Measured results matched the simulated model behavior very closely across all transducer sizes, with the exception of a few smaller transducer dimensions, likely due to the sensitivity to transducer position and the ultrasound beamwidth. The measured efficiency of the link for the smallest PZT crystal (127 $\mu m)^3$ was $2.064\times10^{-5}$, which resulted in 20.64 pW received at the transducer nominally. A maximum of 0.51 $\mu W$ can be recovered at the transducer if the transmit output power density was kept at 720 $mW/cm^2$. Such low power level harvested by the PZT is mainly due to the extreme inefficiency of broadband transducers that were used for the experiments; dedicated, custom-made transducers at each transducer dimension with optimal electrical input impedance could result in more than 2 orders of magnitude improvement in the harvested power level as predicted by the simulation model.

Figure 21C:
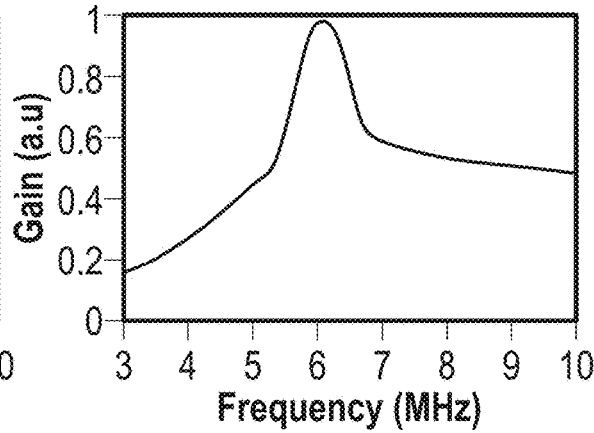
FIG. 21C shows that the frequency response of harvested power of the miniaturized ultrasonic transducer is approximately 6.1 MHz.

The frequency response of electrical voltage harvested on a $(250\ \mu m)^3$ PZT crystal is shown in FIG. 21C. The resonant frequency was measured to be at 6.1 MHz, which matches the shift in the resonant frequency predicted for a cube due to Poisson's ratio and the associated mode coupling between resonant modes along each of the three axes of the cube. Furthermore, the calculated Q of 4 matched the electrically measured Q of the PZT.

The experimental result indicate that the analytical model for power coupling to very small PZT nodes using ultrasound is accurate down to at least ~100 $\mu m$ scale and likely lower. It remains to be seen just how mall a transducer can be fabricated before loss of function. Note that measurements of even smaller nodes (<127 $\mu m$) were limited not by the prototype assembly process but by commercial availability of PZT substrates. Moving forward, the considerable volume of research and techniques that has gone into micro- and nanoelectromechanical RF resonators was be used (see Sadek et al., *Wiring nanoscale biosensors with piezoelectric nanomechanical resonators*, Nano Lett., vol. 10, pp. 1769-1773 (2010); Lin et al., *Low phase noise array-composite micromechanical wine-glass disk oscillator*, IEEE Elec. Dev. Meeting, pp. 1-4 (2005)) and thin-film piezoelectric transducer (see Trolier-McKinstry et al., *Thin film piezoelectrics for MEMS*, J. Electroceram., vol. 12, pp. 7-17 (2004)) to facilitate extremely small (10's of $\mu m$) transducers and to truly assess the scaling theory.

Example 5—Beamforming Using Interrogator Ultrasonic Transducer Array

In this example, an ultrasonic beamforming system capable of interrogating individual implantable sensors via backscatter in a distributed, ultrasound-based recording platform is presented. A custom ASIC drives a 7×2 PZT transducer array with 3 cycles of 32V square wave with a specific programmable time delay to focus the beam at the 800 $\mu m$ neural dust mote placed 50 mm away. The measured acoustic-to-electrical conversion efficiency of the receive mote in water is 0.12% and the overall system delivers 26.3% of the power from the 1.8V power supply to the transducer drive output, consumes 0.75 $\mu m$ in each transmit phase, and has a 0.5% change in the backscatter per volt applied to the input of the backscatter circuit. Further miniaturization of both the transmit array and the receive mote can pave the way for a wearable, chronic sensing and neuromodulation system.

In this highly distributed and asymmetric system, where the number of implanted devices outnumbers the interrogating transceivers by an order of magnitude, beamforming can be used to efficiently interrogate a multitude of implantable devices. Research into beamforming algorithms, trade-offs, and performance in the implantable device platform has demonstrated that cooperation between different interrogators is useful for achieving sufficient interference suppression from nearby implantable devices. See Bertrand et al., *Beamforming approaches for untethered ultrasonic neural dust motes for cortical recording: a simulation study*, IEEE EMBC, 2014, pp. 2625-2628 (August 2014). This example demonstrates a hardware implementation of an ultrasonic beamforming system for the interrogator and implantable device system shown in FIG. 2A. The ASIC (see, e.g., Tang et al., *Integrated ultrasonic system for measuring body-fat composition*, 2015 IEEE International Solid-State Circuits Conference—(ISSCC) Digest of Technical Papers, San Francisco, Calif., 2015, pp. 1-3 (February 2015); Tang et al., *Miniaturizing Ultrasonic System for Portable Health Care and Fitness*, IEEE Transactions on Biomedical Circuits and Systems, vol. 9, no. 6, pp. 767-776 (December 2015)), has 7 identical channels, each with 6 bits of delay control with 5 ns resolution for transmit beam-forming, and integrates high-voltage level shifters and a receive/transmit switch that isolates any electrical feed-through.

The ASIC operates with a single 1.8V supply and generates a 32V square wave to actuate piezoelectric transducers using integrated charge pumps and level shifters. The system delivers ~32.5% of the power from the 1.8V supply to the 32V output voltage and ~81% from 32V to the output load (each transducer element is 4.6 pF). The ASIC block diagram is shown in FIG. 2A; the circuit details to enable such low energy consumption per measurement can be found in Tang et al., *Integrated ultrasonic system for measuring body-fat composition*, 2015 IEEE International Solid-State Circuits Conference—(ISSCC) Digest of Technical Papers, San Francisco, Calif., 2015, pp. 1-3 (February 2015). The ASIC is fabricated in 0.18 μm CMOS with high voltage transistors. The chip area is 2.0 mm$^2$ and includes the complete system except for the digital controller, ADCs, and two off-chip blocking capacitors.

The design of a transducer array is a strong function of the desired penetration depth, aperture size, and element size. Quantitatively, the Rayleigh distance, R, of the array can be computed as follows:

$$R = \frac{D^2}{4\lambda}$$

where D is the size of the aperture and λ is the wavelength of ultrasound in the propagation medium. By definition, Rayleigh distance is the distance at which the beam radiated by the array is fully formed; in other words, the pressure field converges to a natural focus at the Rayleigh distance and in order to maximize the received power, it is preferable to place the receiver at one Rayleigh distance where beam spreading is the minimum.

The frequency of operation is optimized to the size of the element. A preliminary study in a water tank has shown that the maximum energy efficiency is achieved with a (800 μm)$^3$ PZT crystal, which has a resonant frequency of 1.6 MHz post-encapsulation, resulting in λ ~950 μm. The pitch between each element is chosen to be an odd multiple of half wavelength in order to beamform effectively. As a result, for this demonstration of beamforming capabilities, the overall aperture is ~14 mm, resulting in the Rayleigh distance of 50 mm. At 50 mm, given the element size of 800 μm, each element is sufficiently far from the field (R=0.17 mm); therefore, the beam pattern of individual element should be omni-directional enough to allow beamforming.

There are several transmit and receive beamforming techniques that can be implemented. In this paper, time delay-and-sum transmit beamforming algorithm is chosen, such that the signals constructively interfere in the target direction. This algorithm is capable of demonstrating beam-steering and maximal power transfer to various implantable devices. In order to accommodate backscatter communication to multiple implantable devices simultaneously, more sophisticated algorithms may be required. These can include delay-and-sum beamforming, linearly constrained minimum-variance beamforming, convex-optimized beamforming for a single beam, 'multicast' beamforming w/ convex optimization, maximum kurtosis beamforming, minimum variance distortionless response robust adaptive beamforming, polyadic tensor decomposition, and deconvolution of mote impulse response from multi-Rx-channel time-domain data. The detailed treatment of one aspect of this problem is described in Bertrand et al., *Beamforming approaches for untethered ultrasonic neural dust motes for cortical recording: a simulation study*, IEEE EMBC, 2014, pp. 2625-2628 (August 2014).

Each of the 7 channels is driven by 3 cycles of 32V square wave with a specific programmable time delay such that the energy is focused at the observation distance of 50 mm. The time delay applied to each channel is calculated based on the difference in the propagation distance to the focus point from the center of the array and the propagation speed of the ultrasound wave in the medium.

Ultrasim was used to characterize the propagation behavior of ultrasound wave in water with the 1D array described above. Simulated XY (FIG. 26A) and XZ (FIG. 26C) cross-sectional beam patterns closely match the measurement as shown, despite not modeling the PDMS encapsulation.

Water is used as the medium for measuring the beamforming system as it exhibits similar acoustic properties as the tissue. Pre-metalized Lead Zirconate Titanate (PZT) sheets (APC International, Mackeyville, Pa.) are diced with a wafer saw to 800 μm×800 μm×800 μm crystals (parallel capacitance of 4.6 pF each), which is the size of each transmit element. Each PZT element is electrically connected to the corresponding channel in the ASIC by using a conductive copper foil and epoxy for the bottom terminal and a wirebond for the top terminal. The array is encapsulated in PDMS (Sylgard 184, Dow Corning, Midland, Mich.) to protect the wirebond and provide insulation. The quality factor of the PZT crystal post encapsulation is ~7. The array is organized into 7 groups of 2×1 elements, with the pitch of ~5/2λ~2.3 mm. The array measures approximately 14 mm×3 mm. Finally, the entire assembly is encased in a cylindrical tube with the diameter of 25 mm and the height of 60 mm and the tube is filled with water.

The transducer array's 2D beam pattern and output are calibrated using a capsule hydrophone (HGL-0400, Onda, Sunnyvale, Calif.). The hydrophone is mounted on a computer-controlled 2D translating stage (VelMex, Bloomfield, N.Y.). The hydrophone has an acceptance angle (~6 dB at 5 MHz) of 30°, which is sufficient to capture the beam given the transmission distance of 50 mm and the scan range (±4 mm).

Figure 26A:
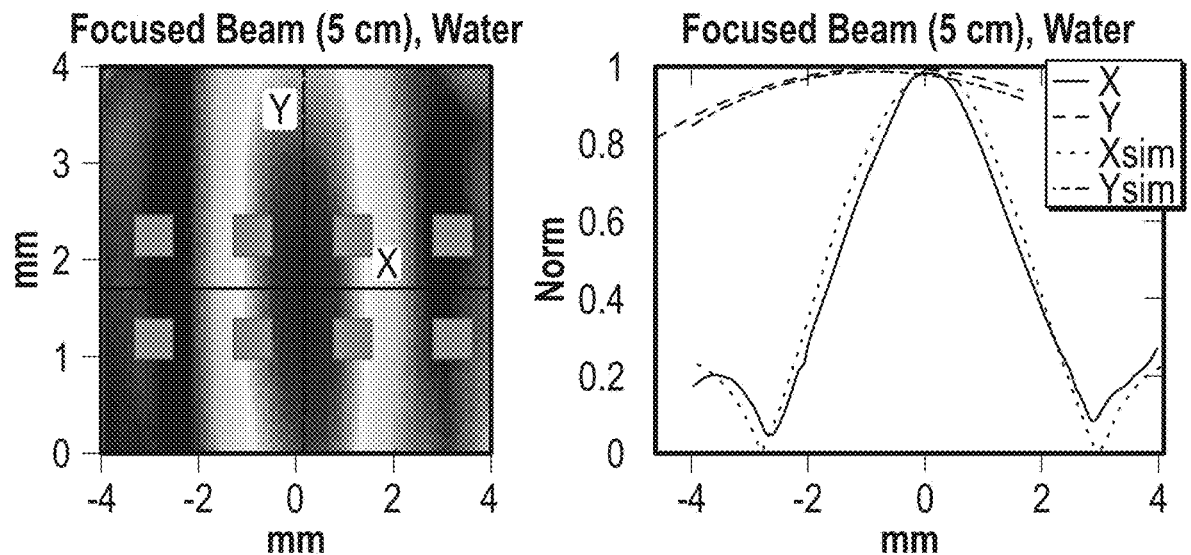
FIG. 26A shows a focused 2D beam pattern from a transducer array in the XY plane. The measured beam approximates the simulated beam in both the X and Y dimensions.
Figure 26B:
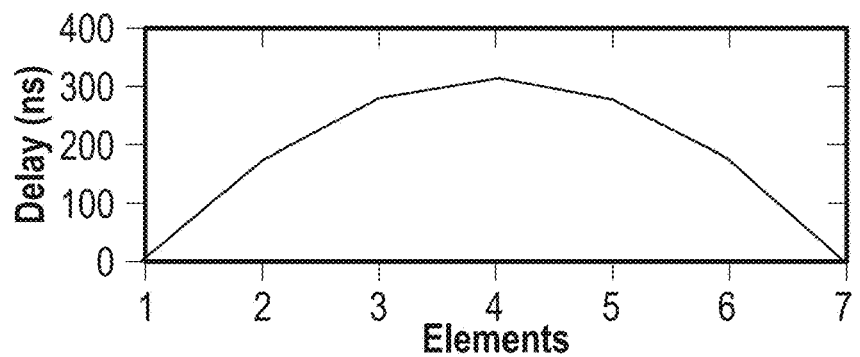
FIG. 26B shows the delay time applied to each transducer element in the ultrasonic transducer array.

The measured XY cross-sectional beam pattern with the overlay of the array is shown in FIG. 26A. The applied delay for each transducer in the array (element) is shown in FIG. 26B. The ~6 dB beamwidth at the focal point is 3.2 mm~3λ. The flexibility of the ASIC allows for both wide and granular programming of the delays. The peak pressure level of the array at 50 mm before and after beamforming is ~6 kPa and ~20 kPa, respectively. The 3× in the transmitted output pressure wave after beamforming matches the simulation.

Figure 26C:
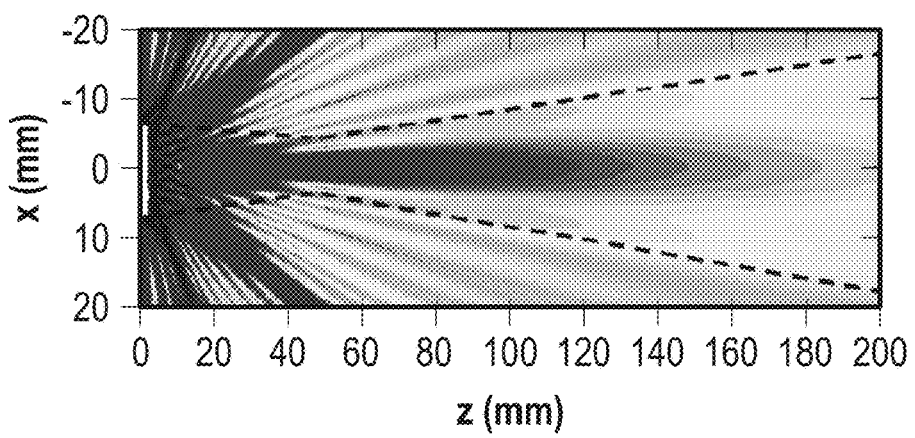
FIG. 26C shows a simulated 2D XZ cross-sectional beam pattern.

The simulation also verifies that the Rayleigh distance of the array is at 50 mm as shown in FIG. 26C.

Figure 27A:
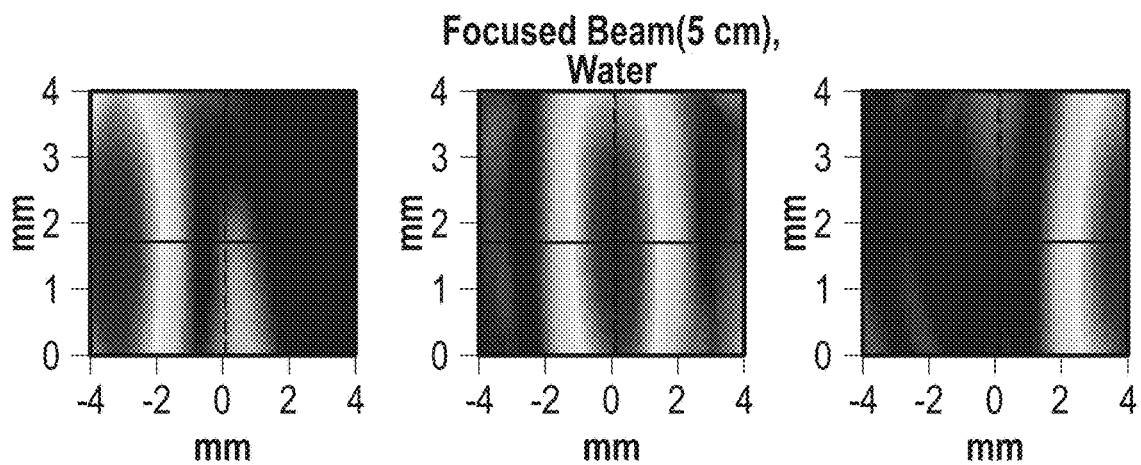
FIG. 27A shows beam steering of an ultrasonic wave beam transmitted from a transducer array. Underneath each beam pattern is the delay for each transducer in the array to obtain the measured beam pattern, as shown in FIG. 27B.
Figure 27B:
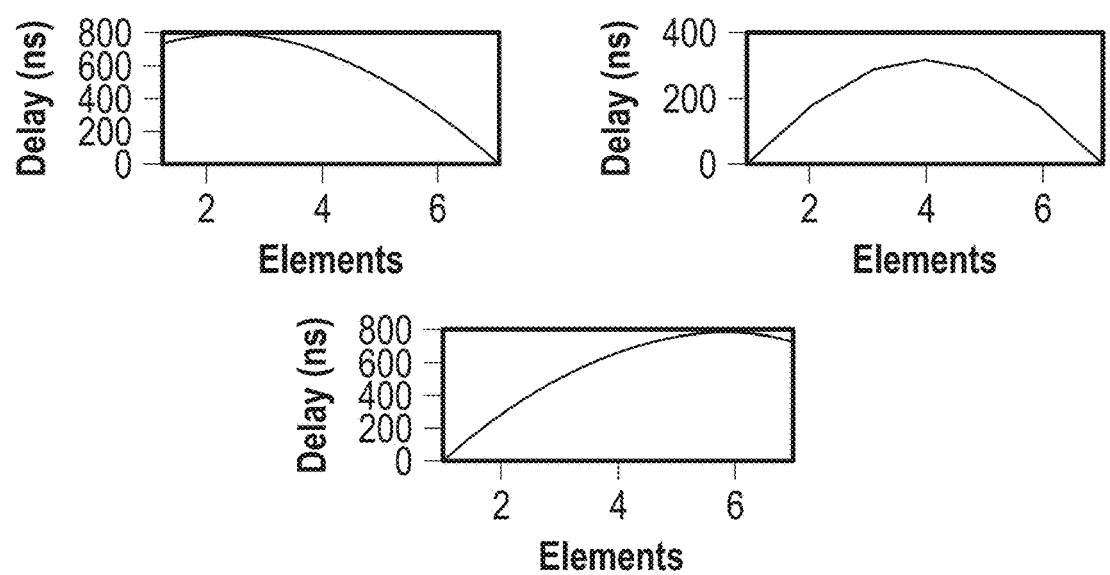
FIG. 27C shows the 1D beam pattern in the X-axis for each beam pattern shown in FIG. 27A. The measured beam pattern closely approximates the simulated beam pattern.
Figure 27C:
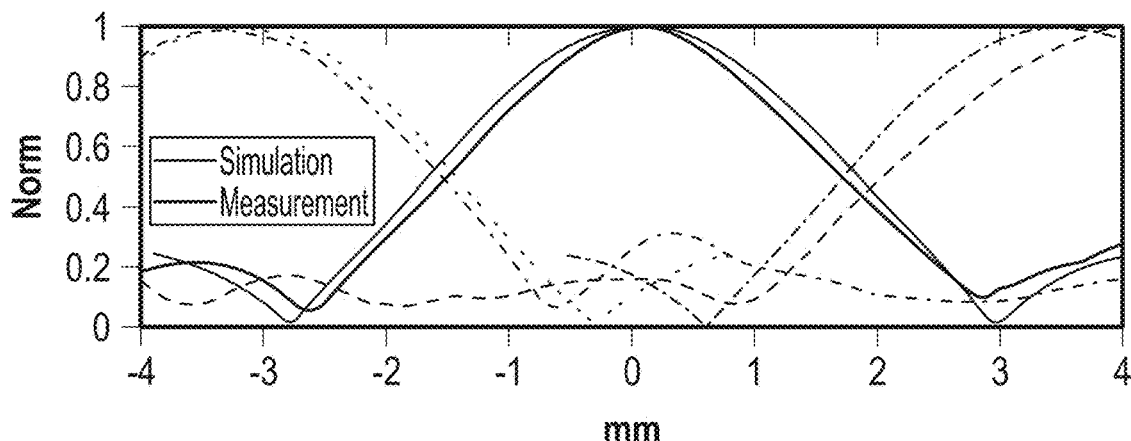

Additionally, in order to verify the capability to interrogate multiple implantable devices, it was verified the beam steering capability of the array as shown in FIG. 27A (showing beam steering at three different positions in the XY-plane), with the time delay for each beam position shown underneath in FIG. 27B. The 1D beam steering matches very closely with the simulation, as shown in FIG. 27C. Note that the beam steering range is limited to ±4 mm due to the mechanical construct of the array, rather than the electronic capability.

The hydrophone is replaced with an implantable device (with a 800 µm×800 µm×800 µm bulk piezoelectric transducer) and placed at the transmission distance of 50 mm to verify the power link. The open-circuit peak-to-peak voltage measured at the mote is 65 mV, for a transmit pulse-duration of 2.56 µs. The spatial peak average acoustic power integrated over the −6 dB beamwidth at the focal point is 750 µW, which is 0.005% of the FDA safety limit. The maximum harvestable power at the mote is 0.9 µW, resulting in the measured acoustic-to-electrical conversion efficiency of 0.12%. The measured result is in agreement with the link model (see Seo et al., *Model validation of untethered ultrasonic neural dust motes for cortical recording*, J. Neurosci. Methods, vol. 244, pp. 114-122 (2015)). The system delivers 26.3% of the power from the 1.8V power supply to the transducer drive output (defined as driving efficiency) and consumes 0.75 µJ in each transmit phase.

The ultrasonic backscatter communication capability of the system is verified by measuring the difference in the backscattered voltage level as the input to the backscatter circuit (see Seo et al., *Model validation of untethered ultrasonic neural dust motes for cortical recording*, J. Neurosci. Methods, vol. 244, pp. 114-122 (2015)), and is adjusted with a DC power supply. The transmit time and the period of the system are 3 µs and 80 µs, leaving a ~77 µs window for reception. A 2×1 element in the center of the array is used for receiving the backscatter. The output of the receive crystals is amplified and digitized for processing. The measured backscatter sensitivity is ~0.5% per volt applied to the input of the backscatter circuit, which is in agreement with the simulation. The overall performance of the system is summarized in Table 5.

TABLE 5

Summary of System Performance

| | |
|---|---|
| Supply voltage | 1.8 V |
| Output voltage | 32 V |
| Number of channels | 7 |
| Operating frequency | 1.6 MHz |
| Charge pump + level shifter efficiency | 26.3% |
| Acoustic-to-Electrical efficiency | 0.12% |
| Backscatter change | 0.5%/V |
| Energy per transmit phase | 0.75 µJ |

Our measurements with the ultrasonic beamforming system suggest that transmit beamforming alone can provide sufficient signal-to-noise ratio (SNR) to enable multiple sensors interrogation in the neural dust platform. The decrease in the SNR with the miniaturization of the dust mote can be largely mitigated by implementing receive beamform. Furthermore, in order to increase the rate of interrogation, one could explore an alternative means of multiplexing, such as spatial multiplexing where multiple motes are interrogated simultaneously with the same transmit beam. However, it is important to consider the system design tradeoff between processing/communication burden to power consumption. Additionally, sufficient suppression of interferences from nearby dust motes is necessary to achieve the required SNR.

The acoustic-to-electrical efficiency at 0.12% currently dominates the efficiency $$\left(\frac{P_{harvested}}{P_{1.8\,V\,supply}}\right)$$

of the overall system. Despite such low efficiency of the power link, if ~1% of the FDA safety regulation (spatial peak average of 1.9 W/cm$^2$) can be outputted, it is possible harvest up to 0.92V peak-to-peak voltage and 180 µW at the 800 µm ultrasonic transducer 50 mm away in water.

Furthermore, the low efficiency of the power link in this demonstration is attributed to such large transmission distance, as determined by the array aperture and the element size. For peripheral nerve intervention, for example, the desired transmission distance is approximately 5 mm, which includes the thickness of skin, tissue, etc. In order to be at the far field of the array, the aperture should be ~4.4 mm. Further scaling of each element can reduce the overall dimensions of the array aperture and the transmission distance down to the desired 5 mm. Simulation indicates that acoustic-to-electrical efficiency up to 1% can be achieved in water with a 100 µm receive ultrasonic transducer.

For transmission in tissue, assuming 3 dB/cm/MHz loss in tissue, FIG. 28 shows the scaling of both link efficiency and received power level given operation at 1% of the FDA safety limit. Despite this rather conservative loss, at 100 µm, the simulation indicates that it is possible to harvest up to 0.6V peak-to-peak voltage and 75 µW. Therefore, wireless power transfer in tissue using this platform is feasible. Furthermore, this power level is sufficient to operate highly efficient, low-power energy harvesting circuits and charge pumps, similar to the ASIC presented here, to output voltages that are suitable for electrically stimulating nearby neurons and detecting physiological conditions using sensors.

Example 6—Wireless Recording in the Peripheral Nervous System with Ultrasonic Neural Dust The following example demonstrates implantable device systems for recording neural signals. The example shows that ultrasound is effective at delivering power to mm scale devices in tissue; likewise, passive, battery-less communication using backscatter enables high-fidelity transmission of electromyogram (EMG) and electroneurogram (ENG) signals from anesthetized rats. These results highlight the potential for an ultrasound-based neural interface system for advancing future bioelectronics-based therapies. The example further provides methods for determining the location and movement of the implantable device.

Figure 29C:
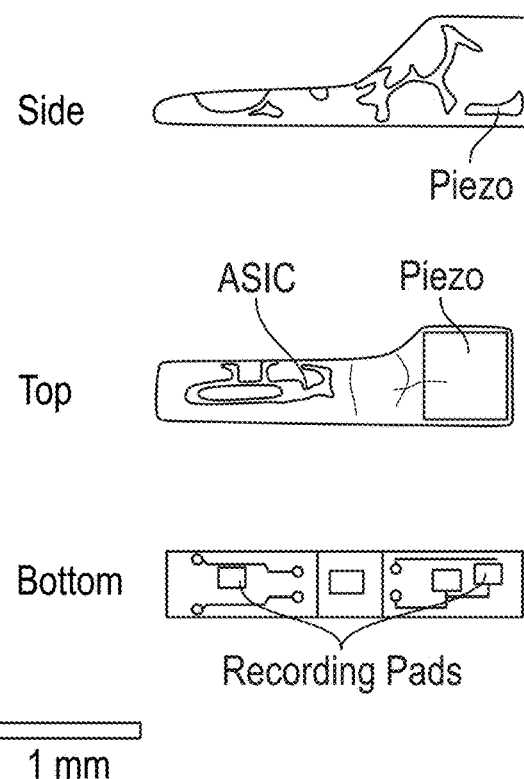
Figure 29D:
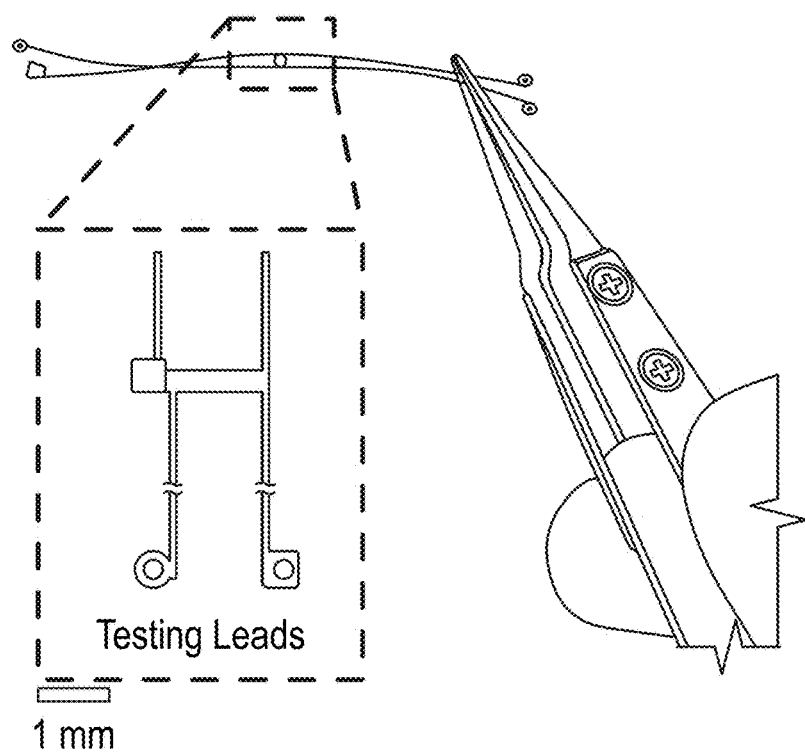
Figure 30:
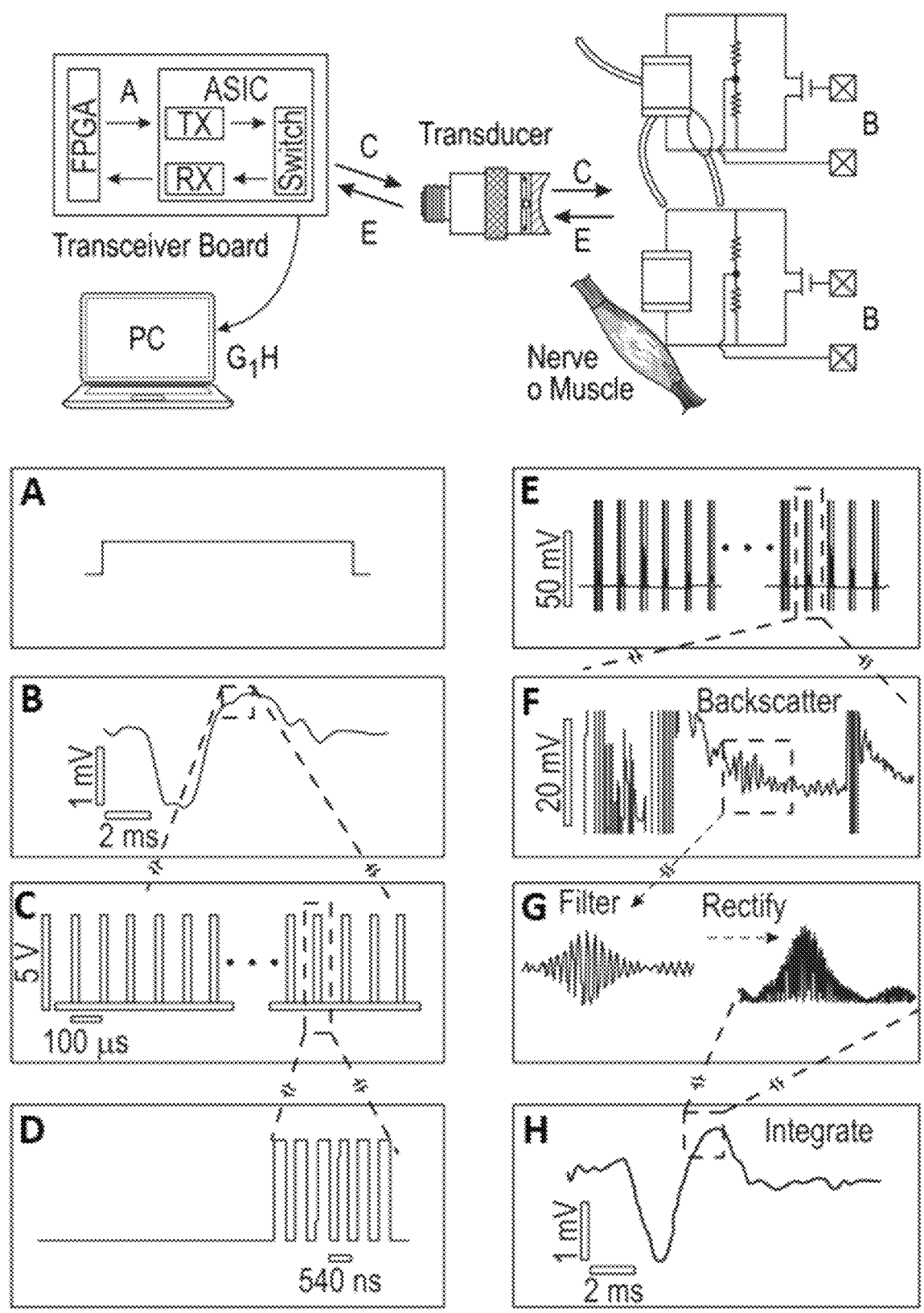
FIG. 30, panels A-H, illustrates communication between an exemplary interrogator and an implantable device. The top of FIG. 30 is a schematic of the flow of information. Panels A-H at the bottom of FIG. 30 represents time traces of signals at each step referenced in the diagram shown at the top of the figure. At A in the schematic, the FPGA from the interrogator generates a trigger signal (panel A) to initiate recording. Panel B shows an extracellular, electrophysiological potential presented to the recording electrodes (B in the schematic) on an implantable device. Panel C shows that upon receiving the trigger from the FPGA (see C in schematic), the transceiver board generates a series of transmit pulses. At the end of the transmit cycle, the switch on the ASIC of the interrogator disconnects the transmit module and connects the receive module. Panel D shows zoomed-in transmit pulse sequence, showing 6 pulses at 1.85 MHz. Panel E shows backscatter from the implantable device (E in schematic), which reaches the transducer at approximately $2t_{Rayleigh}$. Panel F shows zoomed-in backscatter waveforms. The backscatter waveform includes a large saturating signal which overlaps with the transmitted pulses is electrical feedthrough and is ignored. When returning, backscattered pulses can be seen subsequent to the transmission window. Panel G shows the backscattered waveforms being filtered, rectified, and the area under the curve is computed in order to produce reconstructed waveforms. Panel H shows the reconstructed waveform sampled at 10 kHz. Each point of the reconstructed waveform is computed by calculating the area under the curve of the appropriate reflected pulses, received every 100 μs.

The implantable device system was used in vivo to report electroneurogram (ENG) recordings from the sciatic nerve in a peripheral nervous system, and an electromyogram (EMG) recording from a gastrocnemius muscle of a subject rat. The system included an external ultrasonic transceiver board which powers and communicates with ma millimeter-scale sensor implanted not either a nerve or muscle. See FIG. 29A. The implantable device included a piezoelectric crystal, a single custom transistor, and a pair of recording electrodes. See FIGS. 29B, 29C, and 29D.

During operation, the external transducer alternates between a) emitting a series of six 540 ns pulses every 100 µs and b) listening for any reflected pulses. The entire sequence of transmit, receive and reconstruction events are detailed in FIG. 30A-H; this sequence is repeated every 100 µs during operation. Briefly, pulses of ultrasonic energy emitted by the external transducer impinge on the piezocrystal and are, in part, reflected back towards the external transducer. In addition, some of the ultrasonic energy causes the piezocrystal to vibrate; as this occurs, the piezocrystal converts the mechanical power of the ultrasound wave into electrical power, which is supplied to the transistor. Any extracellular voltage change across the two recording electrodes modulates the transistor's gate, changing the amount of current flowing between the terminals of the crystal. These changes in current, in turn, alter the vibration of the crystal and the intensity of the reflected ultrasonic energy. Thus, the shape of the reflected ultrasonic pulses encodes the electrophysiological voltage signal seen by the implanted electrodes and this electrophysiological signal can be reconstructed externally. The performance specifications of neural dust in comparison to other state-of-the-art systems are summarized in Table 6.

An implantable device was manufactured with on a 50 µm thick polyimide flexible printed circuit board (PCB) with an ultrasonic transducer piezocrystal (0.75 mm×0.75 mm×0.75 mm) and a custom transistor (0.5 mm×0.45 mm) attached to the topside of the board with a conductive silver paste. Electrical connections between the components are made using aluminum wirebonds and conductive gold traces. Exposed gold recording pads on the bottom of the board (0.2 mm×0.2 mm) are separated by 1.8 mm and make contact on the nerve or muscle to record electrophysiological signals. Recorded signals are sent to the transistor's input through micro-vias. Additionally, some implants were equipped with 0.35 mm-wide, 25 mm-long, flexible, compliant leads with test points for simultaneous measurement of both the voltage across the piezocrystal and direct wired measurement of the extracellular potential across the electrode pair used by the ultrasonic transducer (this direct, wired recording of extracellular potential as the ground truth measurement is referred to below, which is used as a control for the ultrasonically reconstructed data). The entire implant is encapsulated in a medical grade UV-curable epoxy to protect wirebonds and provide insulation. A single implantable device measures roughly 0.8 mm×3 mm×1 mm. The size of the implants is limited only by our use of commercial polyimide backplane technology, which is commercially accessible to anyone; relying on more aggressive assembly techniques with in-house polymer patterning would produce implants not much larger than the piezocrystal dimensions (yielding a ~1 mm$^3$ implant).

Further details on implantable device assembly. Lead zirconate titanate (PZT) sheets (841, APC Int., Mackeyvile, Pa.) with ~12 µm of fired on silver were diced to desired dimensions using a dicing saw (DAD3240, Disco, Santa Clara, Calif.) with a ceramic blade (PN CX-010-270-080-H). The diced PZT coupon, along with the custom transistor, were attached to a 50 µm thick polyimide flexible PCB with immersion gold (Altaflex, Santa Clara, Calif.) using a thin layer of two-part silver epoxy with 1:1 mix ratio (H20E, Epotek, Billerica, Mass.). The board was cured at 150° C., which is far below the melting temperature of polyimide and the Curie temperature of the PZT, for 10 minutes. The custom transistor was wirebonded using an aluminum ultrasonic wirebonder (7400B, West Bond, Scotts Valley, Calif.) to pre-patterned targets. In order to prevent charge build-up on the PZT from the wedge contact, top and bottom contacts of the PZT were discharged to a thin metal sheet prior to wirebonding the top contact of the PZT to close the circuits. Medical-grade, UV-curable epoxy (OG116-31, Epotek) was used to protect the wirebond and provide insulation. The platform was then cured in UV chamber (Flash, Asiga, Anaheim Hills, Calif.) with 92 mW/cm$^2$ @ 365 nm for 3 minutes.

A custom integrated circuit operates the external transceiver board and enables low-noise interrogation. An external, ultrasonic transceiver board interfaces with the implantable device by both supplying power (transmit (TX) mode) and receiving reflected signals (receive (RX) mode). This system is a low-power, programmable, and portable transceiver board that drives a commercially available external ultrasonic transducer (V323-SU, Olympus, Waltham, Mass.). The transceiver board exhibited a de-rated pressure focus at ~8.9 mm (FIG. 31A). The XY cross-sectional beam-pattern clearly demonstrated the transition from the near-field to far-field propagation of the beam, with the narrowest beam at the Rayleigh distance (FIG. 31B). The

TABLE 6

|  | Ref. 1 | Ref. 2 | Ref. 3 | Ref 4 | Ref. 5 | This Example |
|---|---|---|---|---|---|---|
| Power Source | Wireless (RF) | Wireless (RF) | Wireless (RF) | Wireless (RF) | Wireless (US) | Wireless (US) |
| Gain | 46 dB | 30 d | — | — | — | N/A |
| Bandwidth | 10 kHz | 0.5 kHz | 3 kHz | 5 kHz | — | >30 kHz |
| TX Frequency | 1.5 GHz | 300 MHz | 2.2-2.45 GHz | 2.4 MHz | 1 MHz | 1.85 MHz |
| Resolution | 10 bits | 15 bits | — | — | — | 8 bits (digitizer) |
| Noise Floor | 6.5 µV$_{rms}$ | 1.2 µV$_{rms}$ | 500 µV$_{rms}$ | 63 µV$_{rms}$ | — | 180 µV$_{rms}$* |
| # Channels | 4 | 64 | 1 | 1 | 1 | 1 |
| Total TX Power | 50 mW | 12 mW | 47 mW | 40 mW | 0.36 mW | 0.12 mW |
| Avg. Power (per ch) | 2.63 µW | 3.52 µW | 0 µW | 0 µW | 85 µW | 0 µW |
| Wireless Data Rate | 1 Mbps | 1 Mbps | — | — | — | 0.5 Mbps |
| Range in Tissue | 0.6 mm | 10 mm | 15 mm | 13 mm | 30 mm | 8.8 mm |
| Volume (per ch) | — | — | 24 mm$^3$ | 360 mm$^3$ | 45 mm$^3$ | 2.4 mm$^3$ |

*In a stationary, water tank setup transducer was driven with a 5 V peak-to-peak voltage signal at 1.85 MHz. The measured de-rated peak rarefaction pressure was 14 kPa, resulting in a mechanical index (MI) of 0.01. De-rated spatial pulse peak average ($I_{SPPA}$) and spatial peak time average ($I_{SPTA}$) of 6.37 mW/cm$^2$ and 0.21 mW/cm$^2$ at 10 kHz pulse repetition were 0.0034% and 0.03% of the FDA regulatory limit, respectively. The transceiver board was capable of outputting up to 32 V peak-to-peak and the output pressure increased linearly with the input voltage (FIG. 31C).

Reflections from non-piezocrystal interfaces provide a built in-reference for movement artifacts and temperature drift. The entire system was submerged and characterized in a custom-built water tank with manual 6 degrees-of-freedom (DOF) linear translational and rotational stages (Thorlabs Inc., Newton, N.J.). Distilled water was used as a propagation medium, which exhibits similar acoustic impedance as tissue, at 1.5 MRayls. For initial calibration of the system, a current source (2400-LV, Keithley, Cleveland, Ohio) was used to mimic extracellular signals by forcing electrical current at varying current densities through 0.127 mm thick platinum wires (773000, A-M Systems, Sequim, Wash.) immersed in the tank. The implantable device was submerged in the current path between the electrodes. As current was applied between the wires, a potential difference arose across the implant electrodes. This potential difference was used to mimic extracellular electrophysiological signals during tank testing.

Further details on electrical and ultrasonic characterization of the assembly in water. The custom transistor was electrically tested with a precision current meter (2400-LV, Keithley) and a DC-power supply (3631A, Agilent, Santa Clara, Calif.). To characterize the piezocrystal prior to assembly, an impedance plot was obtained with an impedance analyzer (4285A, Agilent) using two-terminal measurements with open/short/load calibration scheme. The impedance of exposed gold recording pads (0.2 mm×0.2 mm), separated by 1.8 mm on the bottom of the PCB, was measured in Phosphate Buffered Solution (PBS 1×) with an electrochemical impedance spectroscopy (nanoZ, White Matter LLC, Mercer Island, Wash.). The device formed the active electrode and a silver wire formed the reference electrode. Ultrasonic characterization of the transducer was performed in a custom-built water tank. A capsule hydrophone (HGL-0400, Onda Corp., Sunnyvale, Calif.) with 20 dB preamplification (AH-2020, Onda Corp.) was mounted on a computer-controlled 2D translating stage (XSlide, VelMex Inc., Bloomfield, N.Y.) and was used to calibrate the output pressure and characterize beam patterns of a 2.25 MHz single element transducer (V323-SU, Olympus). Verification of ultrasonic power transfer and communication sensitivity was performed in a smaller water-tank with the transducer mounted on manual translational and rotational stages (Thorlabs Inc.). The outline of the implantable device was patterned on an extruded acrylic piece with UV-laser and the implantable device was clamped to the acrylic stage with nylon screws. The position and angle of the transducer with relative to the mote were manually adjusted until the maximum voltage was measured across the piezocrystal. Cable capacitances and parasitics were carefully calibrated by adjusting the series capacitance in the high-impedance probes (N2863B, Agilent). An electric field in the water tank was generated with a current source (2400-LV, Keithley) forcing electrical current at varying current densities through two 0.127 mm thick platinum wires (773000, A-M systems) immersed in the tank. The transceiver board consisted of a custom integrated circuit (IC) in a QFN-64 package that achieved an on-chip 1.8V to 32V charge pump efficiency of 33% and system latency of 20 ns and consumed 16.5 µJ per each transmit cycle (Tang et al., 2015). During the receive mode, the high voltage switch was closed and the signal was amplified by 28 dB; both operations were performed on-chip. The output signal from the chip was digitized by an off-chip 10-bit, 100 MHz analog-to-digital converter (ADC) (LTC2261-12, Linear Technology, Milpitas, Calif.). The outputs of the ADC were fed back into the field-programmable gate array (FPGA) and USB 3.0 integration module (XEM6310-LX45, Opal Kelly, Portland, Oreg.) and transferred to the laptop. The FPGA-USB module was also used to serially program the IC.

Figure 31F:
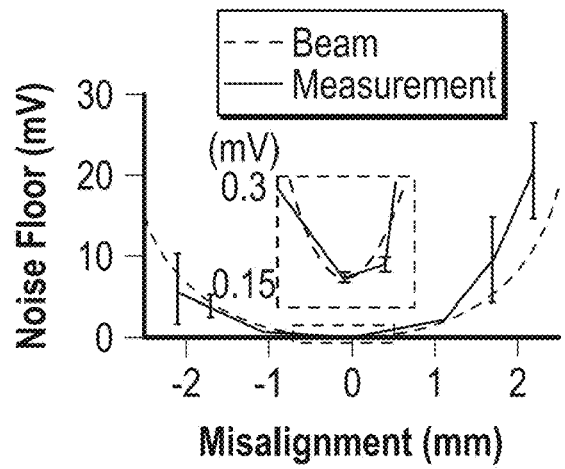
FIG. 31F shows the effect of noise floor as a function of lateral misalignment followed the beampattern power fall-off.
Figure 31G:
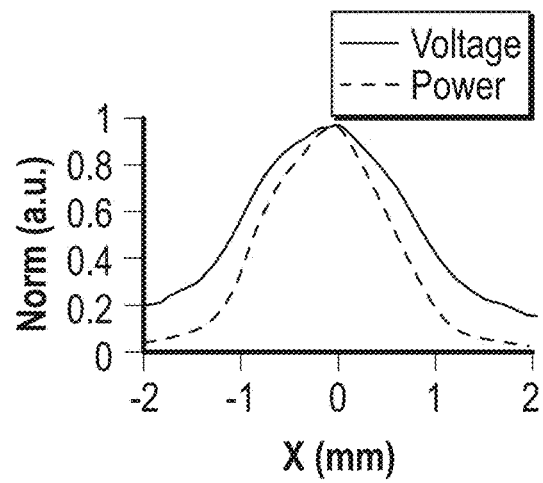
FIG. 31G shows a 1-D plot of the transducer's off-axis voltage and power drop-off at y=0 at Rayleigh distance.
Figure 31H:
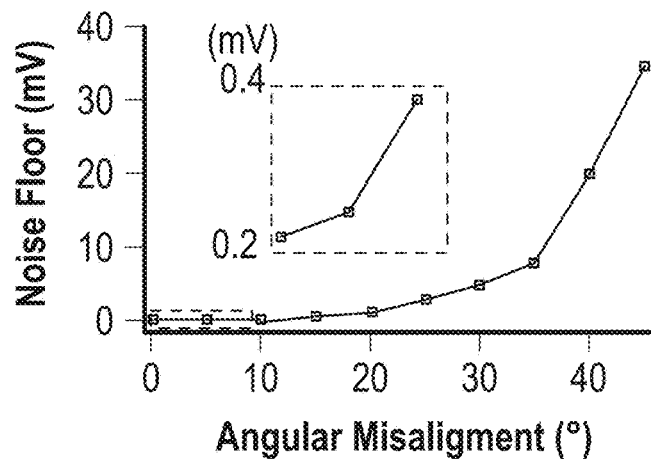
FIG. 31H shows a plot of the drop in the effective noise floor as a function of angular misalignment. Angular misalignment results in a skewed beam pattern: ellipsoidal as opposed to circular. This increases the radius of focal spot (spreading energy out over a larger area); the distortion of the focal spot relaxes the constraint on misalignment.

To interrogate the implantable device, six 540 ns pulses every 100 µs were emitted by the external transducer. See FIG. 30. These emitted pulses reflect off the neural dust mote and produce backscatter pulses back towards the external transducer. Reflected backscatter pulses were recorded by the same transceiver board. The received backscatter waveform exhibits four regions of interest; these are pulses reflecting from four distinct interfaces (FIG. 31D): 1) the water-polymer encapsulation boundary, 2) the top surface of the piezoelectric crystal, 3) the piezo-PCB boundary, and 4) the back of the PCB. As expected, the backscatter amplitude of the signals reflected from the piezoelectric crystal (second region) changed as a function of changes in potential at the recording electrodes. Reflected pulses from other interfaces did not respond to changes in potential at the recording electrodes. Importantly, pulses from the other non-responsive regions were used as a signal level reference, making the system robust to motion or heat-induced artifacts (since pulses reflected from all interfaces change with physical or thermal disturbances of the neural dust mote but only pulses from the second region change as a function of electrophysiological signals). In a water tank, the system showed a linear response to changes in recording electrode potential and a noise floor of ~0.18 mVrms (FIG. 31E). The overall dynamic range of the system is limited by the input range of the transistor and is greater than >500 mV (i.e., there is only an incremental change in the current once the transistor is fully on (input exceeds its threshold voltage) or fully off). The noise floor increased with the measured power drop-off of the beam; 0.7 mm of misalignment degraded it by a factor of two (N=5 devices, FIG. 31F). This lateral mis-alignment-induced increase in the noise floor constitutes the most significant challenge to neural recordings without a beam-steering system (that is, without the use of an external transducer array that can keep the ultrasonic beam focused on the implanted dust mote and, thus, on-axis). On axis, the implantable device converted incident acoustic power to electrical power across the load resistance of the piezo with ~25% efficiency. FIG. 31G plots the off-axis drop-off of voltage and power at one Rayleigh distance for the transducer used in this example. Likewise, FIG. 31H plots the change in effective noise floor as a function of angular misalignment.

Figure 32A:
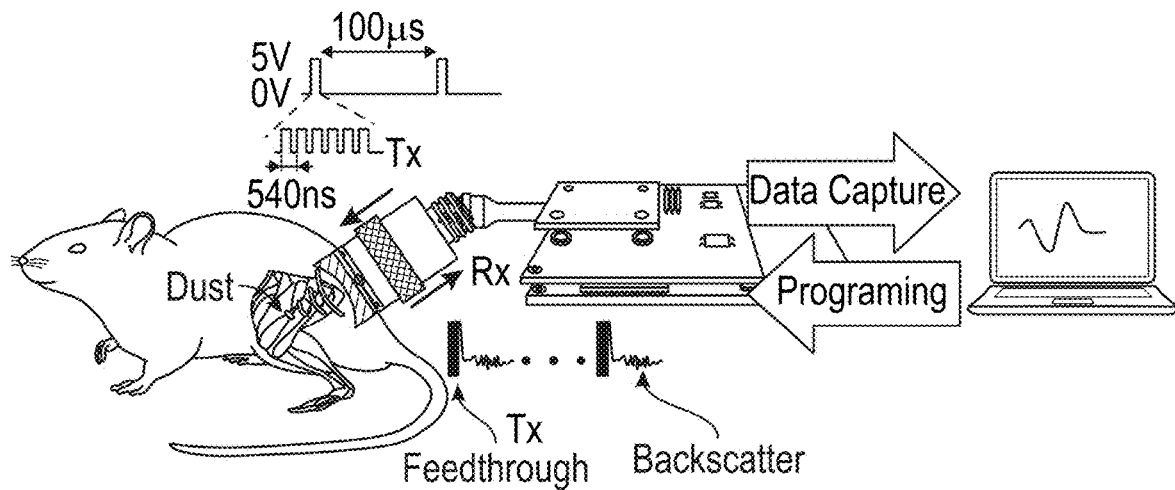
FIG. 32A shows a in-vivo experimental setup for EMG recording from gastrocnemius muscle in rats. The implantable device was placed on the exposed muscle surface and the wound was closed with surgical suture. The external transducer couples ultrasound to the implantable device and the wireless data is recorded and displayed on the computer system (e.g., laptop).
Figure 32B:
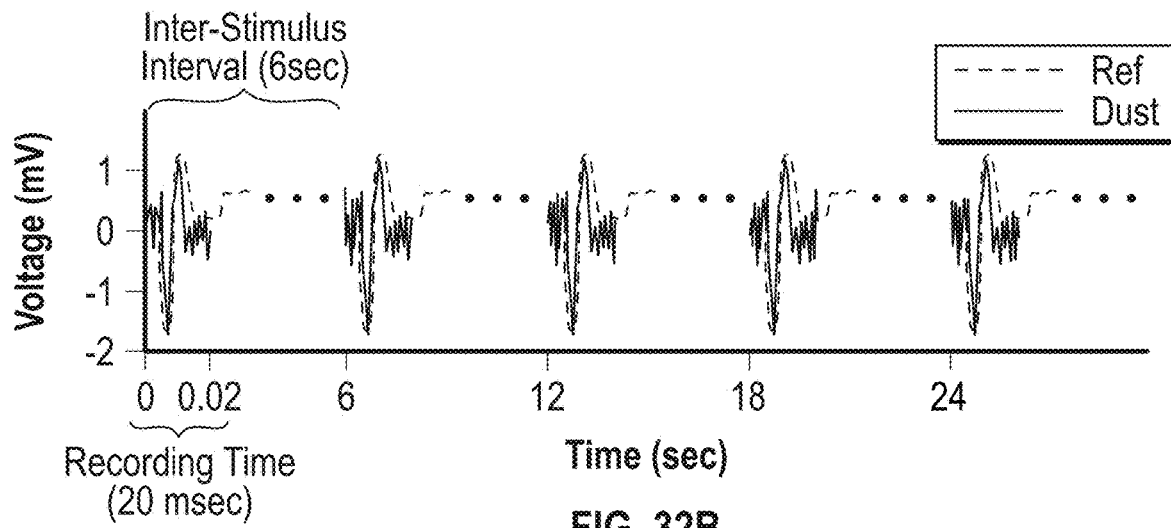
FIG. 32B shows a comparison between ground truth measurement and the reconstructed EMG signals over a number of trials. 20 msec samples were recorded and the inter-stimulus interval was 6 sec.
Figure 32C:
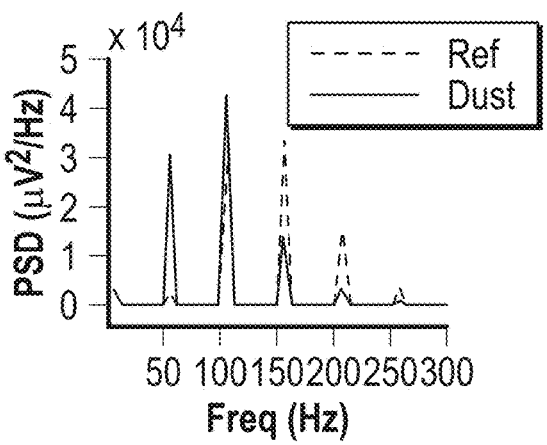
FIG. 32C shows a power spectral density (PSD) of the recorded EMG signal, which showed 4.29e4 µV2/Hz and 3.11e4 µV2/Hz at 107 Hz for ground truth and the reconstructed dust data, respectively, and several harmonics due to edges in the waveform.
Figure 32D:
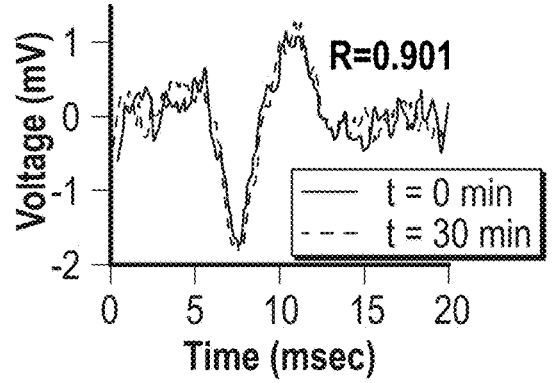
FIG. 32D shows the wireless backscatter data recorded at t=0 min and t=30 min matched with R=0.901.

EMG and ENG can be recorded tetherlessly in-vivo in rodents. EMG responses from the gastrocnemius muscle of adult Long-Evans rats under anesthesia were recorded using the implantable device system. The implantable device ("dust") was placed on the exposed muscle surface, the skin and surrounding connective tissue were then replaced, and the wound was closed with surgical suture (FIG. 32A). The ultrasonic transducer was positioned 8.9 mm away from the implant (one Rayleigh distance of the external transducer) and commercial ultrasound gel (Aquasonic 100, Parker Labs, Fairfield, N.J.) was used to enhance coupling. The system was aligned using a manual manipulator by maximizing the harvested voltage on the piezocrystal measured from the flexible leads. Ag/AgCl wire hook electrodes were placed approximately 2 cm distally on the trunk of the sciatic nerve for the bulk stimulation of muscle fiber responses. Stimulation pulses of 200 µs duration were applied every 6 seconds and data was recorded for 20 ms around the stimulation window (FIG. 32B). The power spectral density (PSD) of the reconstructed data with several harmonics due to edges in the waveform is shown in FIG. 32C. This process could be continued indefinitely, within the limit of the anesthesia protocol; a comparison of data taken after 30 minutes of continuous recording showed no appreciable degradation in recording quality (FIG. 32D).

Figure 33A:
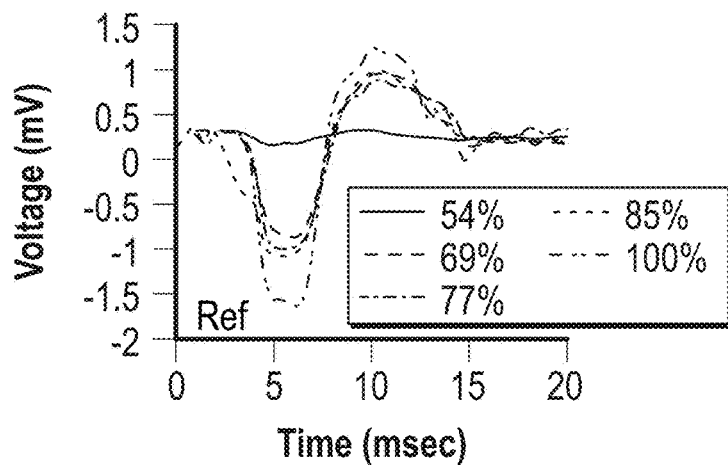
FIG. 33A shows different intensities of EMG signals were recorded in-vivo with the electrodes on the PCB with varying stimulation intensities.
Figure 33B:
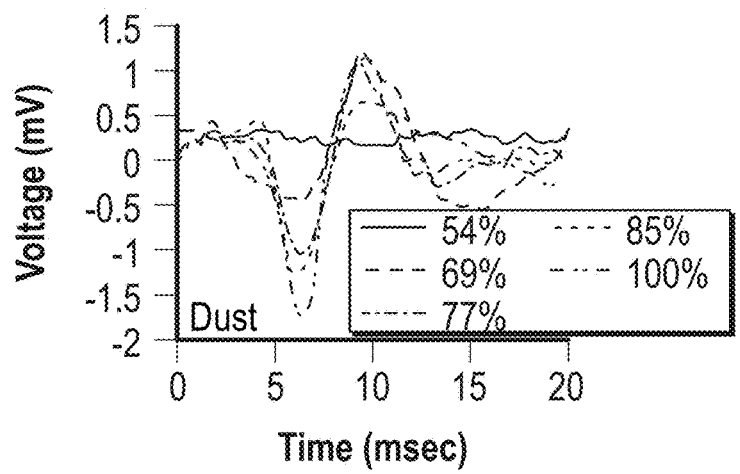
FIG. 33B shows similar gradient EMG responses were recorded wirelessly with the implantable device.
Figure 33C:
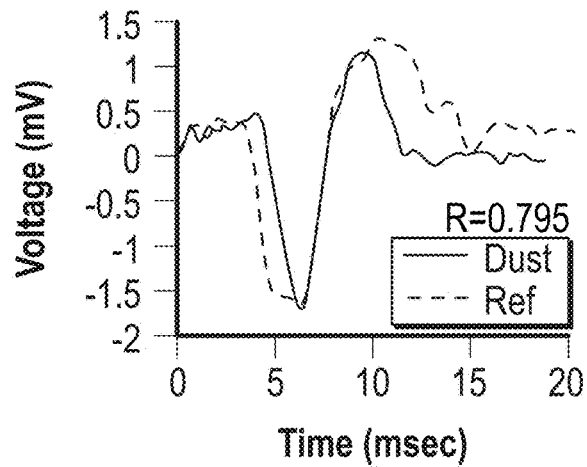
FIG. 33C shows ground truth and reconstruction of EMG signal from the wireless backscatter data at response-saturating stimulation amplitude (100%) matched with R=0.795 (R=0.60, 0.64, 0.67, 0.92 for 54%, 69%, 77%, 89%, respectively).
Figure 33D:
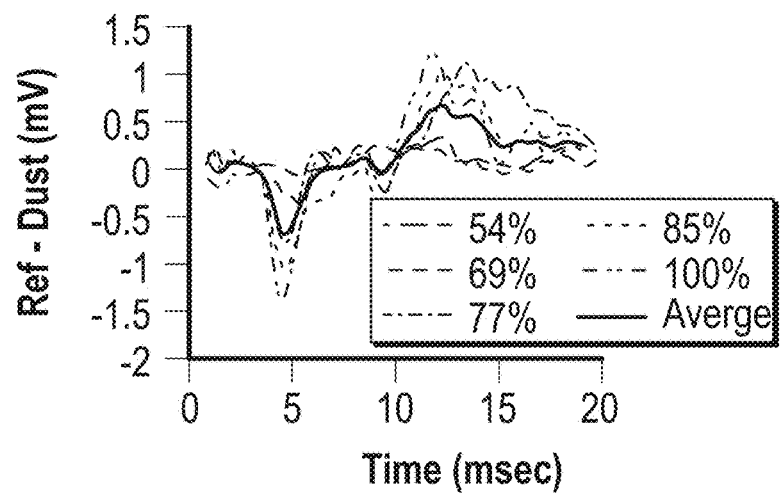
In FIG. 33D, a quantitative comparison showed <0.4 mV match of the salient feature.
Figure 33E:
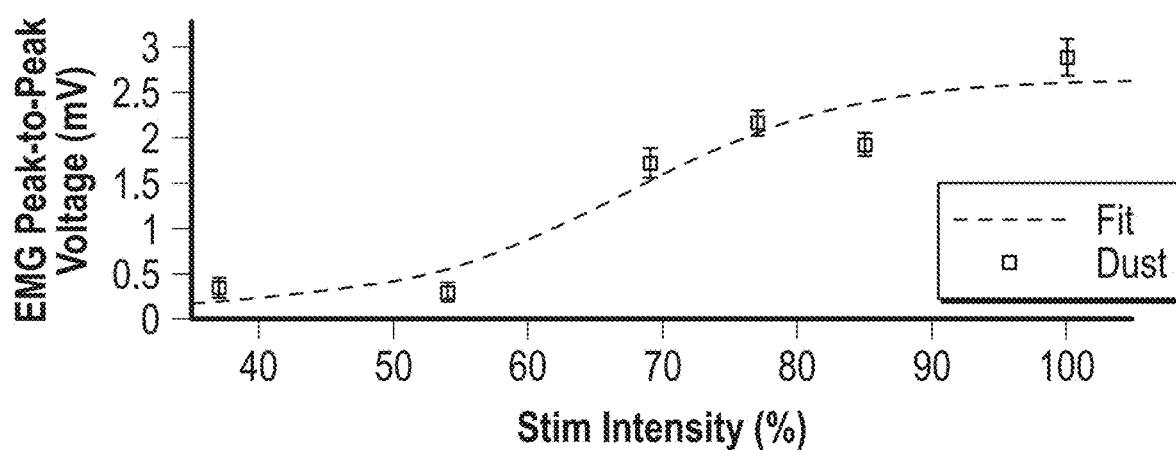
In FIG. 33E, EMG peak-to-peak voltage showed an expected sigmoidal relationship with the stimulation intensity.

EMG recruitment curves were obtained with both ground truth and wireless dust backscatter by varying stimulation amplitude (FIGS. 33A and 33B). Reconstruction of the EMG signal from the wireless backscatter data was sampled at 10 kHz, while the wired, ground truth measurement was sampled at 100 kHz with a noise floor of 0.02 mV. The two signals at response-saturating stimulation amplitude (100%) matched with R=0.795 (FIG. 33C). The difference between the wireless and wired data was within ±0.4 mV (FIG. 33D). The salient feature of the implantable device EMG response was approximately 1 ms narrower than the ground truth, which caused the largest error in the difference plot (FIGS. 33C and 33D). The responses from skeletal muscle fibers occurred 5 ms post-stimulation and persisted for 5 ms. The peak-to-peak voltage of the EMG shows a sigmoidal response as a function of stimulation intensity (FIG. 33E). The error bars indicate the measurement uncertainties from two rats and 10 samples each per stimulation amplitude. The minimum signal detected by the implantable device is approximately 0.25 mV, which is in good agreement with the noise floor measurement made in a water tank.

Figure 34A:
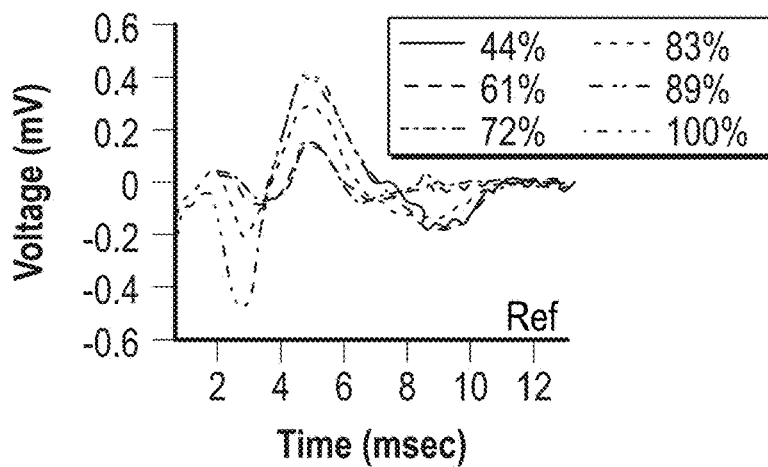
FIG. 34A shows different intensities of ENG signals that were recorded in-vivo with the electrodes on the PCB with varying stimulation intensities.
Figure 34B:
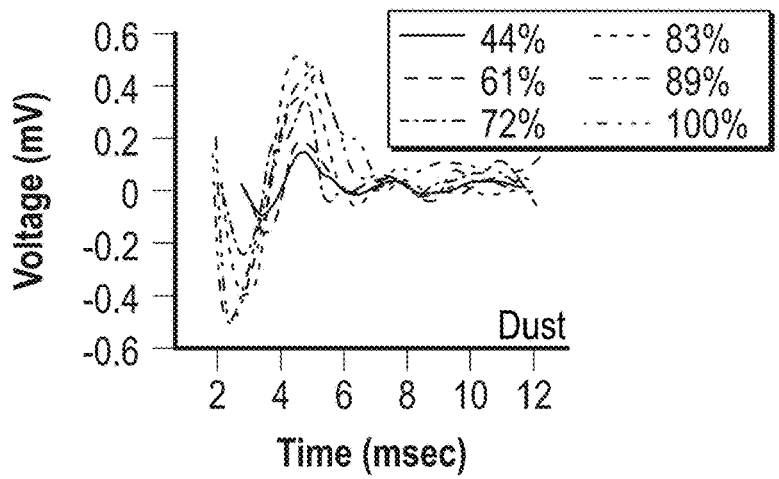
FIG. 34B shows similar gradient ENG responses were recorded wirelessly with the mote.
Figure 34C:
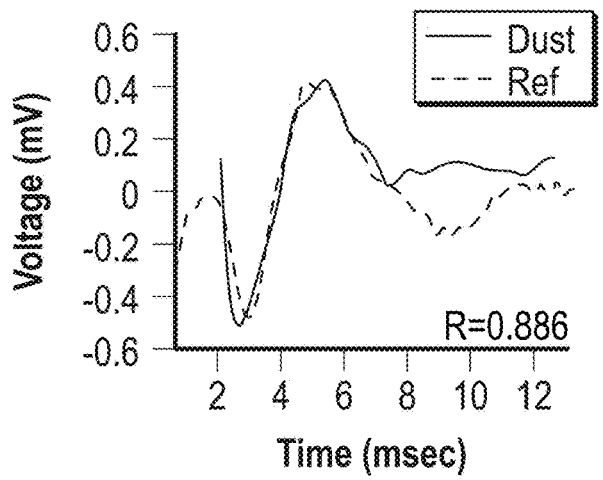
FIG. 34C shows ground truth and reconstruction of ENG signal from the wireless backscatter data at response-saturating stimulation amplitude (100%) matched with R=0.886 (R=0.822, 0.821, 0.69, 0.918, 0.87 for 44%, 61%, 72%, 83%, 89%, respectively).
Figure 34D:
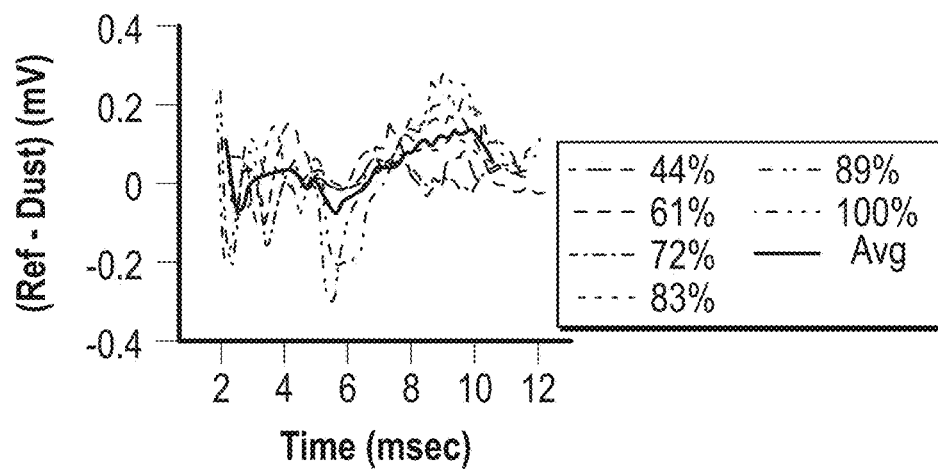
In FIG. 34D, quantitative comparison showed <0.2 mV match of the salient feature.
Figure 34E:
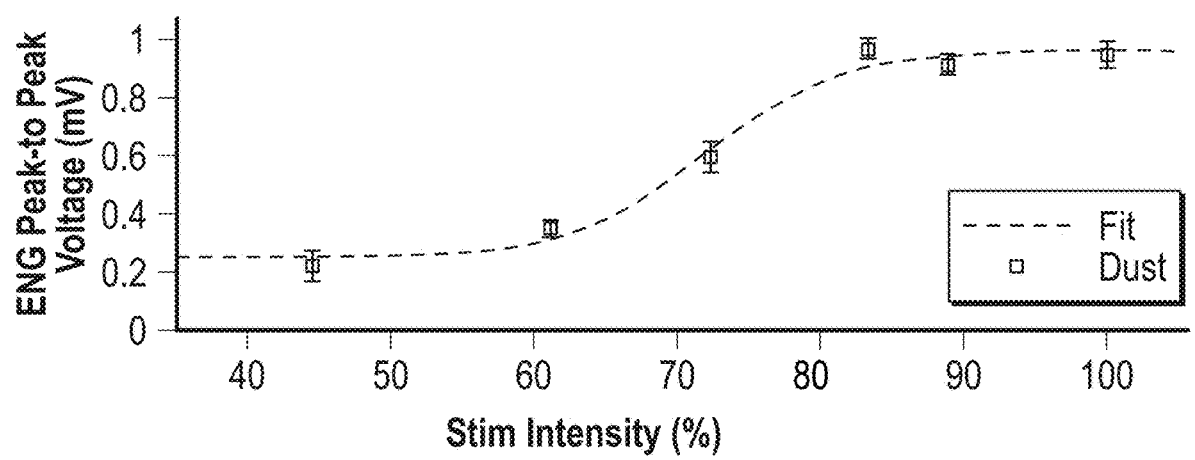
In FIG. 34E, ENG peak-to-peak voltage showed an expected sigmoidal relationship with the stimulation intensity.

A similar setup was prepared to measure the electroneurogram (ENG) response from the main branch of the sciatic nerve in anesthetized rats. The sciatic nerve was exposed by separating the hamstring muscles and the neural dust mote was placed and sutured to the nerve, with the recording electrodes making contact with the epineurium. A similar graded response was measured on both ground truth and wireless backscatter from the implantable device by varying stimulation current amplitude delivered to bipolar stainless steel electrodes placed in the foot (FIGS. 34A and 34B). The two signals at response-saturating stimulation amplitude (100%) matched with R=0.886 (FIG. 34C); the average error was within ±0.2 mV (FIG. 34D). The peak-to-peak ENG voltage showed a sigmoidal response with the error bars indicating uncertainties from two rats and 10 samples each per stimulation amplitude. The minimum signal detected by the implantable device was again at 0.25 mV (FIG. 34E).

Further details on experiment setup and surgical procedures. All animal procedures were performed in accordance with University of California Berkeley Animal Care and Use Committee regulations. Adult male Long-Evans rats were used for all experiments. Prior to the start of surgery, animals were anesthetized with a mixture of ketamine (50 mg/kg) and xylazine (5 mg/kg) IP. The fur surrounding the surgical site was shaved and cleaned. For EMG recordings, a patch of gastrocnemius muscle roughly 10 mm×5 mm in size was exposed by removing the overlying skin and fascia. The implantable device was then placed on the exposed muscle, and the skin and fascia were replaced and the wound was closed with 5/0 surgical suture. For ENG recordings, the sciatic nerve was exposed by making an incision from the sciatic notch to the knee, and separating the hamstring muscles. The implantable device was then placed in contact with the epineurium of the main branch of the sciatic nerve bundle, and sutured to the nerve using 10/0 microsurgical suture. Animals were euthanized at the conclusion of the experiments. Constant-current stimulation was delivered using an isolated pulse stimulator (2100, A-M Systems). Single biphasic pulses with a 2 ms pulse width were used to deliver stimulation at various current amplitudes. For each experiment, electrophysiological responses from 10 stimulations (i.e., samples) were recorded. The FPGA-USB module generated a trigger for the stimulator every 6 seconds. For EMG experiments, bipolar Ag—AgCl hook electrodes placed around the trunk of the sciatic nerve were used for stimulation. To evoke ENG activity, 28G stainless steel needle electrodes were placed in the foot with an inter-electrode distance of approximately 5 mm. The wired signals were amplified (100×) by a battery-powered differential amplifier with a built-in bandpass filter (DAM50, WPI, Sarasota, Fla.) set at 10 Hz-1 kHz. The ground reference for the amplifier was a 28G stainless steel needle electrode placed in the contralateral foot relative to the recording setup. The output of the amplifier was connected to a multi-channel digitizer, sampled at 100 kHz, and recorded on computer. The implantable device was placed one Rayleigh distance from the transducer (8.9 mm), which corresponded to 5.9 µs transit time, assuming an acoustic velocity of 1500 m/s in water. 6-cycles of square waves at 1.85 MHz with peak voltage of 5 V were launched every 100 µs (pulse repetition frequency (PRF) of 10 kHz). The total transmit pulse width was approximately, 3.3 µs, which was sufficiently small to prevent any overlaps with the first harvested voltage measurement at 5.9 µs. Given that the first reflection back to the transducer (e.g., backscatter) occurred at approximately 11.8 µs (twice the transit time) and persisted until for 3.3 µs, the maximum PRF (e.g., in this context, the sampling rate) was ~66 kHz. Given that the bulk peripheral nerve responses occurred below 1 kHz, a PRF of 10 kHz was chosen to sufficiently capture the dynamics. In order to sample the backscatter waveform at 1.85 MHz without losing signal fidelity, the off-chip ADC on the transceiver board was heavily oversampled at 50 MHz. This resulted in ~8 Mbits of data in a 10 ms neural recording, which was stored in a 128 MByte, 16-bit wide, synchronous DDR2 DRAM (MT47H64M16HR-3, Micron Technology, Boise, Id.). The raw waveforms were transferred to the laptop via the USB interface post-recording. The raw waveforms were simultaneously recorded using an 8-bit digitizer (USB-5133, National Instruments, Santa Clara, Calif.) for comparison. Raw backscatter waveforms, sampled at 50 MHz, from each experiment were sliced and time-aligned to be averaged over samples. The averaged signals were bandpass-filtered with a symmetric 4th order Butterworth filter from 10 Hz to 1 kHz. The distinct characteristics of the backscatter waveform (FIG. 31D) were used as a template to locate the region of interest. The signals were then rectified and the integral of the region was computed to estimate the input voltage signal, which exhibited a linear response (FIG. 31E). Multiplication factor for the signal was extracted from the ground truth measurement.

In-vivo ultrasonic transmission. A 2.25 MHz single element transducer (V323-SU, Olympus NDT, Waltham, Mass.) was used to generate 6 pulses at 1.85 MHz. The transducer had a measured half-power bandwidth (HPBW) of more than 2.5 MHz. In order to measure the transmission loss through the tissue, various thicknesses of skin found near the gastrocnemius muscle of a male Long-Evans rat was placed in between the transducer and the implantable device. The harvested voltage on the piezocrystal with and without tissue was obtained and the 8.9 mm of tissue resulted in 10 dB of tissue attenuation.

Figure 35A:
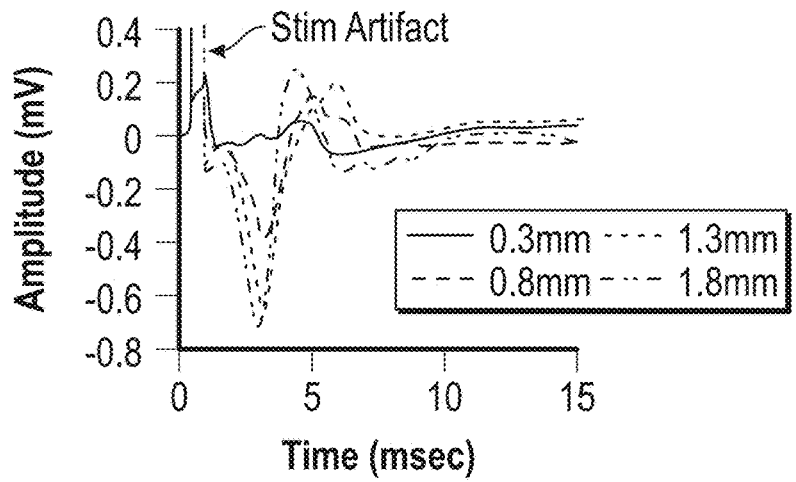
FIG. 35A shows recorded time-domain ENG responses for different electrode spacing.
Figure 35B:
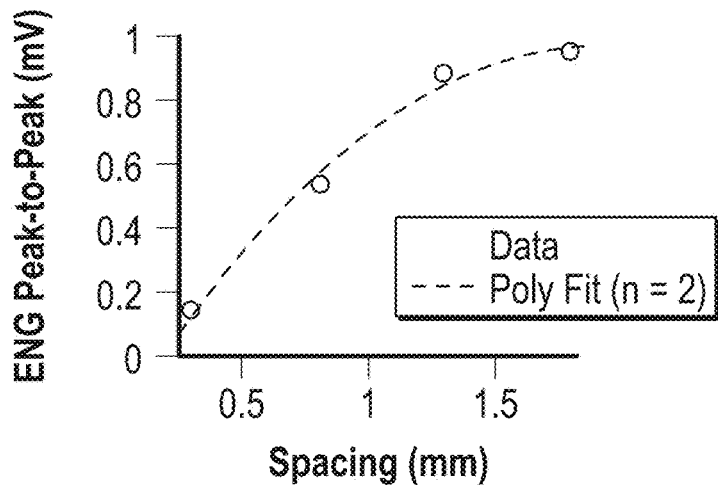
FIG. 35B shows peak-to-peak ENG with varying electrode spacing.

ENG recording with different electrode spacing. Recording electrodes with various spacing were fabricated on a 50 μm thick polyimide flexible printed circuit board (PCB). There were a total of 5 electrodes, each measuring 0.2 mm×0.2 mm, and one of them was used as the reference electrode. Other electrodes were spaced 0.3 mm, 0.8 mm, 1.3 mm, and 1.8 mm, respectively, apart from the reference electrode. The spacing board was placed in contact with the epineurium of the main branch of the sciatic nerve bundle (distal) and sutured to the nerve. Bipolar Ag—AgCl hook electrodes placed around the trunk of the sciatic nerve (proximal) were used for stimulation. Constant-current simulation of a single biphasic pulse with a duration of 0.5 ms every 1 second was delivered using an isolated pulse stimulator (2100, A-M Systems, Sequim, Wash.). The recorded signals with various spacing between the electrodes were amplified (100×) by a battery-powered differential amplifier with a built-in bandpass filter (DAM50, WPI, Sarasota, Fla.) set at 10 Hz-1 kHz (FIG. 35A). As expected, the peak-to-peak voltage recorded on the electrode increased with the spacing at least quadratically. The amplitude saturated after the spacing of 1.3 mm, confirming that the electrode spacing of 1.8 mm on the recording sensor was sufficient to capture the maximum, saturated ENG response (FIG. 35B).

Calculation of acoustic intensity. Several parameters are established by the American Institute for Ultrasound in Medicine and National Electronics Manufacturers Administration (NEMA) to assess the safety of an ultrasonic system. The acoustic power output of diagnostic ultrasonic system is limited by the de-rated values of spatial-peak pulse-average intensity (ISPPA), spatial-peak temporal average intensity (ISPTA), and mechanical index (MI). These de-rated values are computed by multiplying the measured values in water by an attenuation factor of 0.3 dB/cm/MHz to simulate the effects on tissue. A capsule hydrophone (HGL-0400, Onda Corp) with 20 dB preamplification (AH-2020, Onda Corp., Sunnyvale, Calif.) was mounted on a computer-controlled 2D translating stage (XSlide, VelMex Inc., Newton, N.J.) and immersed in a custom-built water tank to calibrate the output pressure of a 2.25 MHz single element transducer (V323-SU, Olympus NDT). 6-cycles of square waves at 1.85 MHz with peak input voltage of 5 V were launched every 1 ms (pulse repetition frequency (PRF) of 10 kHz) to the transducer. The hydrophone was placed one Rayleigh distance from the transducer (8.9 mm). The pulse intensity integral (PII) is defined as:

$$PII = \int \frac{p^2(t)}{z_o} dt$$

where p is the instantaneous peak pressure, and $z_o$ is the characteristic acoustic impedance of the medium. In the case of water, $z_o$ is estimated to be 1.5 MRayl. The $I_{SPPA}$ is defined as:

$$I_{SPPA} = \frac{PII}{PD},$$

where PD is the pulse duration defined as (t)(0.9×PII−0.1×PII)×1.25, as outlined by the standards established by NEMA. The $I_{SPPA}$ is defined as: $I_{SPPA}$=PII×PRF, where PRF is the pulse repetition frequency. The MI is defined as:

$$MI = \frac{p_r}{\sqrt{f}},$$

where $p_r$ is the peak rarefaction pressure and f is the acoustic frequency.

or in-vivo, acute recordings in a stationary, anaesthetized rat model were used to collect compound action potentials from the main branch of the sciatic nerve as well as evoked EMG from the gastrocnemius muscle. The performance of the system was equivalent to conventional electrophysiological recordings employing microelectrodes and cabled electronics. One of the principal strengths of the demonstrated technology is that, unlike conventional radio frequency technology, ultrasound-based systems appear scalable down to <100 μm size, opening the door to a new technological path in implantable electronics. Physics limits how small a good radio frequency receiver can be due to the long wavelengths of radio frequency energy (millimeters to centimeters) and the high degree of absorption of radio frequency energy into tissue (which heats up the tissue and limits the total power than can be sent to an implant). Ultrasonic systems fare much better in both areas, allowing for the design of extremely small receiver devices. In addition, the extreme miniaturization of lower power electronics allows for useful recording electronics to be incorporated into such small packages. Flat, low-profile piezo-transducer with proper impedance matching would enable a wearable transceiver board small enough for awake, behaving rodent neurophysiology. Additionally, wearable, battery-powered multi-element arrays would allow for beam-steering of the ultrasonic beam, with several advantages: 1) the implantable devices could be maintained on-axis even in the face of relative motion between the implantable device and external transducer; 2) multiple implantable devices could be interrogated by sweeping the focused beam electronically; and 3) post-surgical tuning of the implantable device location would be made easier. Additional de-noising of the transceiver drive electronics should also help decrease the noise floor. In addition, the calculated scaling predictions suggest that <500 μm scale implantable devices are feasible. To do this, a number of material and microfabrication challenges exist, including the use of microfabricated backplanes, solder microbumping assembly of components (instead of the conventional wirebonding approach used here) and the use of thin film encapsulants (instead of medical grade epoxy) such as parylene. Transitioning away from PZT piezocrystals to biocompatible BaTiO3 single crystal transducers is also contemplated; taken together, these developments would open the way for chronic studies of neural and muscular tissue recording.

Example 7—Digital Communication Link Between Implantable Device and Interrogator A system including an implantable device and an interrogator having a transducer array is validated with a benchtop setup mimicking an in-vivo environment. Ultrasound coupling gel serves as a tissue phantom due to its acoustic impedance which is similar to that of target biological tissues (approximately 1.5 MRayl). An implantable device with a bulk piezoelectric transducer with direct connections to the two electrodes contacting the transducer is placed in the tissue phantom, and the interrogator transducer array is coupled to the gel. Both elements are attached to precision controlled stages for accurate positioning. The transducer array is placed 14 mm away from the dust mote, which corresponds to a 18.6 μs round-trip time of flight assuming an acoustic velocity of 1,540 m/s in ultrasound coupling gel. The transducer array is excited with six 1.8 MHz, 0-32 V rectangular pulses, and the backscatter signal is digitized with 2000 samples at 17 Msps and 12-bits of resolution. For time-domain backscatter inspection, complete backscatter waveforms are filtered in real time on the device and sent to the client through a wired, serial connection. In normal operation, the complete modulation extraction algorithm is applied to the backscatter data on the device in real-time, compressing the backscatter signal to four bytes. The processed data is transmitted through Bluetooth's SSP protocol to a remote client and streamed through the GUI in real-time.

Figure 36A:
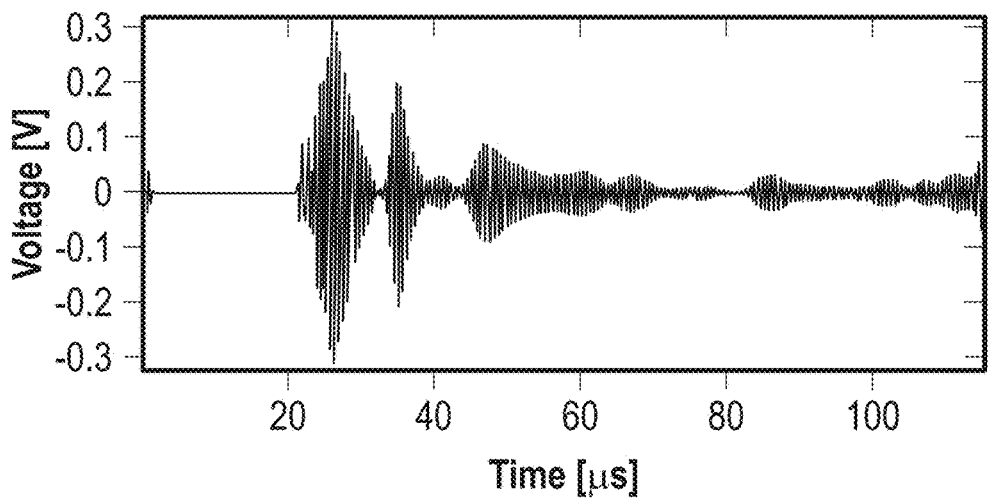
FIG. 36A shows ultrasonic backscatter from an implantable device, with the implantable device implanted inn ultrasound coupling gel used to mimic tissue. The backscatter includes a transmit feedthrough and ring-down centered at 26 microseconds, and the miniaturized ultrasonic transducer backscatter centered around 47 microseconds.
Figure 36B:
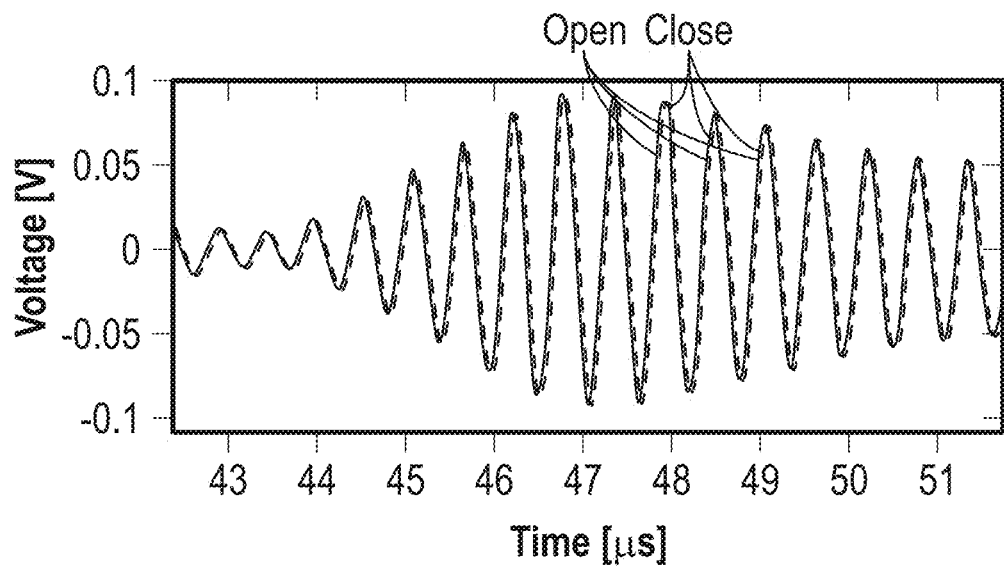
FIG. 36B shows a close-up on the backscatter region from the miniaturized ultrasonic transducer (the responsive region), which shows amplitude modulation as a result of a signal input to the implantable device.

FIG. 36A shows the filtered backscatter signals collected with the described experimental setup. Signals are collected while the dust mote piezocrystal electrodes are in the shorted and opened configurations. The change in impedance due to the switch activity results in a backscatter peak amplitude that is 11.5 mV greater in the open switch configuration, a modulation depth of 6.45%. (FIG. 36B). The long duration of the echo from the mote indicates transducer ringing despite a damping backing layer. While the under-damped transducer system response does spread out the backscatter signal in the time-domain, demodulation is successful as long as the backscatter from the implanted device is captured within the ROI.

Figure 37:
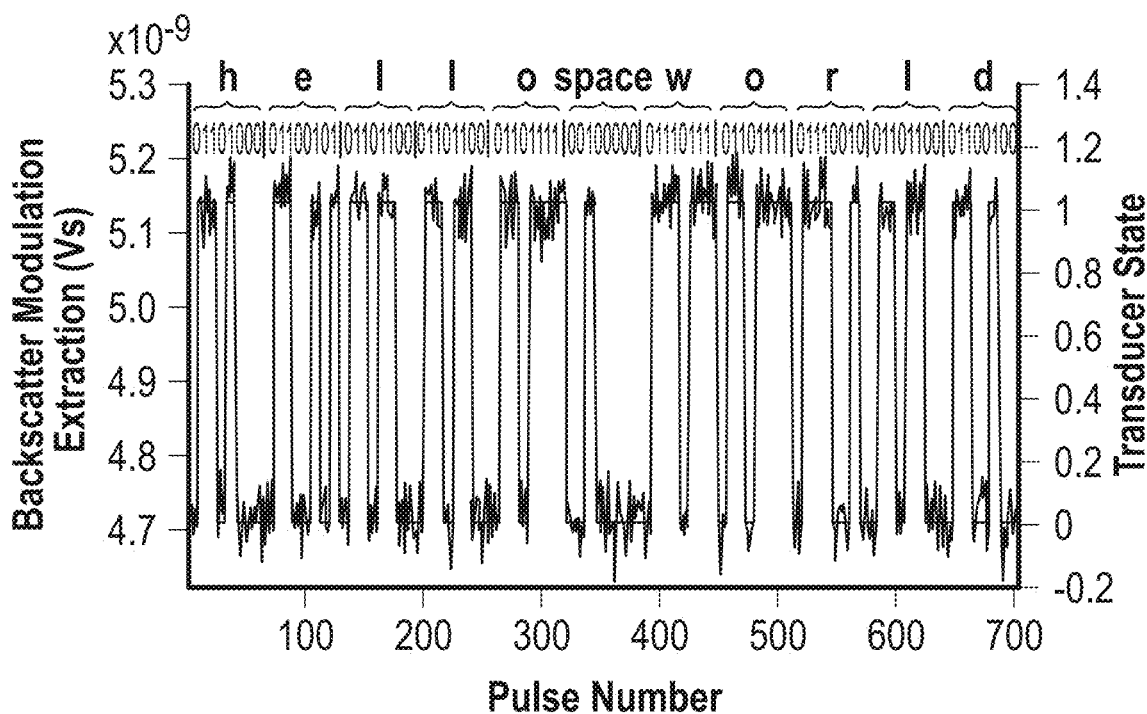
FIG. 37 shows digital data corresponding to ASCII characters 'hello world' wirelessly ready from the implantable device through pulse amplitude backscatter modulation with unipolar encoding.

Using pulse-amplitude-modulated non-return to zero level coding, a backscatter sensor mote is modulated to send a predetermined 11-character ASCII message ("hello world"). The modulation of the device's acoustic impedance is achieved by shunting the piezoelectric transducer across a digitally controlled switch where a high level corresponds to the open configuration and a low level corresponds to the closed configuration. FIG. 37 shows the modulated values on the transducer and the corresponding extracted modulation values of the interrogator. The absolute value and noise margin of the extracted signal values depend on a variety of factors such as mote distance, orientation, and size; however, the extracted waveform remains representative of the modulated signal on the dust mote, varying by a linear scaling factor.

Wirelessly transmitting the extracted backscatter value of the implantable device modulated by "hello world" demonstrates the device's real time communication link with implanted devices. Interrogation of a two state backscatter system provides a robust demonstration of the system's wireless communication link with both an implantable sensor and a remote client. This wireless communication link invites developments toward closed-loop neuromodulation systems to connect the brain with external devices.

The invention claimed is:

1. A closed-loop system, comprising:
   (a) a first implantable device configured to detect a signal comprising:
      a sensor configured to detect the signal in a first tissue;
      an integrated circuit comprising a modulation circuit configured to modulate a current based on the detected signal, and
      a first ultrasonic transducer configured to emit an ultrasonic backscatter encoding information related to the detected physiological signal based on the modulated current;
   (b) an interrogator comprising one or more ultrasonic transducers configured to receive the ultrasonic backscatter encoding the information related to the detected physiological signal, and emit ultrasonic waves encoding a trigger signal; and
   (c) a second implantable device configured to emit an electrical pulse to a second tissue in response to the trigger signal, comprising:
      an ultrasonic transducer configured to receive ultrasonic waves, wherein the received ultrasonic waves power the second device and encode the trigger signal;
      a first electrode and a second electrode configured to be in electrical communication with the second tissue and emit an electrical pulse to the second tissue in response to the trigger signal; and
      an integrated circuit comprising an energy storage circuit.

2. The system of claim 1, wherein the first tissue and the second tissue are the same tissue.

3. The system of claim 1, wherein the first tissue and the second tissue are different tissues.

4. The system of claim 1, wherein the sensor comprises a first electrode and a second electrode configured to be in electrical communication with the first tissue.

5. The system of claim 1, wherein the signal is a physiological signal.

6. The system of claim 1, wherein the signal comprises an electrophysiological signal.

7. The system of claim 1, wherein the signal comprises a temperature, a pH, a pressure, a strain, or a bioimpedance.

8. The system of claim 1, wherein the integrated circuit of the second implantable device comprises a digital circuit.

9. The system of claim 1, wherein the integrated circuit of the second implantable device comprises a mixed-signal integrated circuit configured to operate the first electrode and the second electrode.

10. The system of claim 1, wherein the tissue comprises muscle tissue or an organ.

11. The system of claim 1, wherein the tissue comprises nervous tissue.

12. The system of claim 1, wherein the first implantable device and second implantable device are implantable in a human subject.

13. The system of claim 1, wherein the interrogator is wearable by a subject.

14. A method of stimulating a tissue, comprising:
   receiving ultrasonic waves at a first implantable device configured to detect a physiological signal;
   converting, at the first implantable device, energy from the ultrasonic waves into an electrical current that flows through a modulation circuit;
   detecting, at the first implantable device, the physiological signal;
   producing, at the first implantable device, a modulated electrical current based on the detected physiological signal;
   transducing, at the first implantable device, the modulated electrical current into an ultrasonic backscatter that encodes information related to the detected physiological signal; and
   emitting, from the first implantable device, the ultrasonic backscatter that encodes the information related to the detected physiological signal;

receiving, at an interrogator comprising one or more ultrasonic transducers, the ultrasonic backscatter that encodes the information related to the detected physiological signal;

emitting, from the interrogator, ultrasonic waves configured to power a second implantable device;

receiving, at the second implantable device, the ultrasonic waves configured to power the second implantable device;

converting, at the second implantable device, energy from the ultrasonic waves configured to power the second implantable device into an electrical current that charges an energy storage circuit of the second implantable device;

emitting, from the interrogator, ultrasonic waves encoding a trigger signal;

receiving, at the second implantable device, the ultrasonic waves encoding the trigger signal; and emitting, from the second implantable device, an electrical pulse that stimulates the tissue in response to the trigger signal.

15. The method of claim 14, wherein the physiological signal comprises an electrophysiological signal, a temperature, an analyte concentration, a pH, pressure, strain, or bioimpedance.

16. The method of claim 14, wherein the tissue comprises muscle tissue, an organ, or nervous tissue.

* * * * *